US012742022B2

(12) United States Patent
Garcia-Martinez et al.

(10) Patent No.: US 12,742,022 B2
(45) Date of Patent: Sep. 22, 2026

(54) BINDING MOLECULES FOR THE TREATMENT OF CANCER

(71) Applicant: Boehringer Ingelheim International GmbH, Ingelheim am Rhein (DE)

(72) Inventors: Juan Manuel Garcia-Martinez, Vienna (AT); Stephan Glaser, Vienna (AT); Gale Lee Hansen, Sandy Hook, CT (US); Srinath Kasturirangan, Brookfield, CT (US); Klaus-Peter Kuenkele, Voesendorf (AT); Vladimir H. Voynov, Danbury, CT (US); Andreas Wernitznig, Vienna (AT); Chao Zheng, Briarcliff Manor, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 497 days.

(21) Appl. No.: 18/351,515

(22) Filed: Jul. 13, 2023

(65) Prior Publication Data

US 2024/0052065 A1 Feb. 15, 2024

(30) Foreign Application Priority Data

Jul. 15, 2022 (EP) .................................... 22185100

(51) Int. Cl.
*C07K 16/46* (2006.01)
*A61P 35/00* (2006.01)
*C12N 15/63* (2006.01)

(52) U.S. Cl.
CPC ............ *C07K 16/468* (2013.01); *A61P 35/00* (2018.01); *C12N 15/63* (2013.01); *C07K 2317/14* (2013.01); *C07K 2317/31* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 4,676,980 | A | 6/1987 | Segal et al. |
| 5,731,168 | A | 3/1998 | Carter et al. |
| 2014/0221620 | A1 | 8/2014 | Zhang et al. |

FOREIGN PATENT DOCUMENTS

| | | | |
|---|---|---|---|
| EP | 0307434 | A1 | 3/1989 |
| WO | 1988001649 | A1 | 3/1988 |
| WO | 1990005144 | A1 | 5/1990 |
| WO | 1991017271 | A1 | 11/1991 |
| WO | 1993008829 | A1 | 5/1993 |
| WO | 1994004678 | A1 | 3/1994 |
| WO | 1994013804 | A1 | 6/1994 |
| WO | 1994029348 | A2 | 12/1994 |
| WO | 1998025971 | A1 | 6/1998 |
| WO | 1998048837 | A1 | 11/1998 |
| WO | 1998049185 | A1 | 11/1998 |
| WO | 2001079258 | A1 | 10/2001 |
| WO | 2002056910 | A1 | 7/2002 |
| WO | 2003050531 | A2 | 6/2003 |
| WO | 2003054216 | A2 | 7/2003 |
| WO | 2004003019 | A2 | 1/2004 |
| WO | 2004041865 | A2 | 5/2004 |
| WO | 2006040153 | A2 | 4/2006 |
| WO | 2007042309 | A2 | 4/2007 |
| WO | 2009089004 | A1 | 7/2009 |
| WO | 2011039126 | A1 | 4/2011 |
| WO | 2011098520 | A1 | 8/2011 |
| WO | 2012057328 | A1 | 5/2012 |
| WO | 2012176765 | A1 | 12/2012 |
| WO | 2016075670 | A1 | 5/2016 |
| WO | 2017198741 | A1 | 11/2017 |
| WO | 2018115231 | A2 | 6/2018 |

OTHER PUBLICATIONS

Vieira, Andre F. and Paredes, Joana, P-Cadherin and the Journey to Cancer Metastasis, Oct. 6, 2015, Molecular Cancer, 14:178 (Year: 2015).*

Garcia-Martinez, J.M et al. "Selective Tumor Cell Apoptosis and Tumor Regression in CDH17-Positive Colorectal Cancer Models using BI 905711, a Novel Liver-Sparing TRAILR2 Agonist", (2021) Molecular Cancer Therapeutics, vol. 20, No. 1, 96-108.

Root, Adam et al.; "Development of PF-06671008, a Highly Potent Anti-P-cadherin/Anti-CD3 Bispecific DART Molecule with Extended Half-Life for the Treatment of Cancer", (2016) Antibodies, vol. 5, No. 1, 1-30.

International Search Report for PCT/EP2023/069513 mailed Oct. 18, 2023. 12 pgs.

Altshuler E.P., et al., "Obtaining Recombinant Antibodies and Methods to Increase Their Affinity," Advances in Biological Chemistry, 2010, vol. 50, pp. 203-258 (13 Pages).

Darling R.J., et al., "Kinetic Exclusion Assay Technology: Characterization of Molecular Interactions," Assay and Drug Development Technologies, 2004, vol. 2, No. 6, pp. 647-657 (14 Pages), XP055396049.

(Continued)

*Primary Examiner* — Laura B Goddard
*Assistant Examiner* — Lindsay Dunn
(74) *Attorney, Agent, or Firm* — Mary Breen Smith

(57) ABSTRACT

The present invention relates to novel binding molecules. The invention specifically relates to binding molecules that bind to TNF-related apoptosis-inducing ligand receptor 2 (TRAILR2) and cadherin-3 (CDH3). The invention also relates to nucleic acids encoding such binding molecules; to methods for preparing such binding molecules; to host cells expressing or capable of expressing such binding molecules; to compositions comprising such binding molecules; and to uses of such binding molecules or such compositions, in particular for therapeutic purposes in the field of cancer diseases.

14 Claims, 19 Drawing Sheets

Specification includes a Sequence Listing.

(56) References Cited

OTHER PUBLICATIONS

Malmqvist M., "Surface Plasmon Resonance for Detection and Measurement of Antibody-antigen Affinity and Kinetics," Current Opinion in Immunology, 1993, vol. 5, pp. 282-286, XP023942016.

Norderhaug L., et al., "Versatile Vectors for Transient and Stable Expression of Recombinant Antibody Molecules in Mammalian Cells, "Journal of Immunological Methods, 1997, vol. 204, No. 1, pp. 77-87 (11 Pages).

Riechmann L., et al., "Reshaping Human Antibodies for Therapy," Nature, Mar. 24, 1988, vol. 332, pp. 323-327.

* cited by examiner

Fig. 1

Amino acid sequence of CDH3 (SEQ ID NO:98) (EC1 domain bold and underlined; EC2 domain underlined)

MGLPRGPLAS LLLLQVCWLQ CAASEPCRAV FREAEVTLEA GGAEQEPGQA LGKVFMGCPG
QEPALFSTDN DDFTVRNGET VQERRSLKER NPLKIFPSKR ILRRHKRDWV VAPISVPENG
KGPFPQRLNQ LKSNKDRDTK IFYSITGPGA DSPPEGVFAV EKETGWLLLN KPLDREEIAK
YELFGHAVSE NGASVEDPMN ISIIVTDQND HKPKFTQDTF RGSVLEGVLP GTSVMQVTAT
DEDDAIYTYN GVVAYSIHSQ EPKDPHDLMF TIHRSTGTIS VISSGLDREK VPEYTLTIQA
TDMDGDGSTT TAVAVVEILD ANDNAPMFDP QKYEAHVPEN AVGHEVQRLT VTDLDAPNSP
AWRATYLIMG GDDGDHFTIT THPESNQGIL TTRKGLDFEA KNQHTLYVEV TNEAPFVLKL
PTSTATIVVH VEDVNEAPVF VPPSKVVEVQ EGIPTGEPVC VYTAEDPDKE NQKISYRILR
DPAGWLAMDP DSGQVTAVGT LDREDEQFVR NNIYEVMVLA MDNGSPPTTG TGTLLLTLID
VNDHGPVPEP RQITICNQSP VRQVLNITDK DLSPHTSPFQ AQLTDDSDIY WTAEVNEEGD
TVVLSLKKFL KQDTYDVHLS LSDHGNKEQL TVIRATVCDC HGHVETCPGP WKGGFILPVL
GAVLALLFLL LVLLLLVRKK RKIKEPLLLP EDDTRDNVFY YGEEGGGEED QDYDITQLHR
GLEARPEVVL RNDVAPTIIP TPMYRPRPAN PDEIGNFIIE NLKAANTDPT APPYDTLLVF
DYEGSGSDAA SLSSLTSSAS DQDQDYDYLN EWGSRFKKLA DMYGGGEDD

Amino acid sequence of the EC1 domain of CDH3 (SEQ ID NO:99)

NQLKSNKDRDTKIFYSITGPGADSPPEGVFAVEKETGWLLLNKPLDREEIAKYELFGHAVSENGAS
VEDPMNISIIVTDQNDHKP

Amino acid sequence of the EC2 domain of CDH3 (SEQ ID NO:100)

QVTATDEDDAIYTYNGVVAYSIHSQEPKDPHDLMFTIHRSTGTISVISSGLDREKVPEYTLTIQAT
DMDGDGSTTTAVAVVEILDANDNAP

SEQUENCE LISTING

```
Sequence total quantity: 232
SEQ ID NO: 1           moltype = AA  length = 702
FEATURE                Location/Qualifiers
source                 1..702
                       mol_type = protein
                       organism = synthetic construct
SEQUENCE: 1
QVQLQESGPG LVKPSETLSL TCTVSGGSIS SYYWSWIRQP PGKGLDWIGY IYYSRTTNYN  60
PSLKSRVTIS VDTSKNQFSL KLSSVTAADT AVYYCARARN GIDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGGGS GGSSSELTQD PAVSVALGQT VRITCQGDSL  480
RSYYASWYQQ KPGQAPVLVI YGKNNRPSGI PDRFSGSSSG NTASLTITGA QAEDEADYYC  540
NSRDSSGNHV VFGGGTKLTV LGGGGSGGGG SGGGGSGGGG SEVQLVQSGG GVERPGGSLR  600
LSCAASGFTF DDYGMSWVRQ APGKGLEWVS GINWNGGSTG YADSVKGRVT ISRDNAKNSL  660
YLQMNSLRAE DTAVYYCAKI LGAGRGWYFD LWGKGTTVTV SS                    702

SEQ ID NO: 2           moltype = AA  length = 118
FEATURE                Location/Qualifiers
source                 1..118
                       mol_type = protein
                       organism = synthetic construct
SEQUENCE: 2
QVQLQESGPG LVKPSETLSL TCTVSGGSIS SYYWSWIRQP PGKGLDWIGY IYYSRTTNYN  60
PSLKSRVTIS VDTSKNQFSL KLSSVTAADT AVYYCARARN GIDAFDIWGQ GTMVTVSS    118

SEQ ID NO: 3           moltype = AA  length = 5
FEATURE                Location/Qualifiers
source                 1..5
                       mol_type = protein
                       organism = synthetic construct
```

```
SEQUENCE: 3
SYYWS                                                         5

SEQ ID NO: 4            moltype = AA  length = 16
FEATURE                 Location/Qualifiers
source                  1..16
                        mol_type = protein
                        organism = synthetic construct
SEQUENCE: 4
YIYYSRTTNY NPSLKS                                             16

SEQ ID NO: 5            moltype = AA  length = 10
FEATURE                 Location/Qualifiers
source                  1..10
                        mol_type = protein
                        organism = synthetic construct
SEQUENCE: 5
ARNGIDAFDI                                                    10

SEQ ID NO: 6            moltype = AA  length = 112
FEATURE                 Location/Qualifiers
source                  1..112
                        mol_type = protein
                        organism = synthetic construct
SEQUENCE: 6
DIVMTQSPLS LPVTPGEPAS ISCRSSQSLL HSYGYNYLDW YLQKPGQSPQ LLIYLGSNRA  60
SGVPDRFSGS GSGTDFTLKI SRVEAADVGV YYCMQALQTP LTFGGGTKVE IK         112

SEQ ID NO: 7            moltype = AA  length = 16
FEATURE                 Location/Qualifiers
source                  1..16
                        mol_type = protein
                        organism = synthetic construct
SEQUENCE: 7
RSSQSLLHSY GYNYLD                                             16

SEQ ID NO: 8            moltype = AA  length = 7
FEATURE                 Location/Qualifiers
source                  1..7
                        mol_type = protein
                        organism = synthetic construct
SEQUENCE: 8
LGSNRAS                                                       7

SEQ ID NO: 9            moltype = AA  length = 9
FEATURE                 Location/Qualifiers
source                  1..9
                        mol_type = protein
                        organism = synthetic construct
SEQUENCE: 9
MQALQTPLT                                                     9

SEQ ID NO: 10           moltype =   length =
SEQUENCE: 10
000

SEQ ID NO: 11           moltype = AA  length = 699
FEATURE                 Location/Qualifiers
source                  1..699
                        mol_type = protein
                        organism = synthetic construct
SEQUENCE: 11
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARHS FFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSREEMTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGGGSGGS SSELTQDPAV SVALGQTVRI TCQGDSLRSY  480
YASWYQQKPG QAPVLVIYGK NNRPSGIPDR FSGSSSGNTA SLTITGAQAE DEADYYCNSR  540
DSSGNHVVFG GGTKLTVLGG GGSGGGGSGG GGSGGGGSEV QLVQSGGGVE RPGGSLRLSC  600
AASGFTFDDY GMSWVRQAPG KGLEWVSGIN WNGGSTGYAD SVKGRVTISR DNAKNSLYLQ  660
MNSLRAEDTA VYYCAKILGA GRGWYFDLWG KGTTVTVSS                    699

SEQ ID NO: 12           moltype = AA  length = 115
FEATURE                 Location/Qualifiers
source                  1..115
                        mol_type = protein
```

```
                        organism = synthetic construct
SEQUENCE: 12
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARHS FFDYWGQGTL VTVSS       115

SEQ ID NO: 13           moltype = AA  length = 5
FEATURE                 Location/Qualifiers
source                  1..5
                        mol_type = protein
                        organism = synthetic construct
SEQUENCE: 13
SYWIG                                                              5

SEQ ID NO: 14           moltype = AA  length = 17
FEATURE                 Location/Qualifiers
source                  1..17
                        mol_type = protein
                        organism = synthetic construct
SEQUENCE: 14
IIYPGDSDTR YSPSFQG                                                 17

SEQ ID NO: 15           moltype = AA  length = 6
FEATURE                 Location/Qualifiers
source                  1..6
                        mol_type = protein
                        organism = synthetic construct
SEQUENCE: 15
HSFFDY                                                             6

SEQ ID NO: 16           moltype = AA  length = 108
FEATURE                 Location/Qualifiers
source                  1..108
                        mol_type = protein
                        organism = synthetic construct
SEQUENCE: 16
EIVLTQSPGT LSLSPGERAT LSCRASQSVS SIYLAWYQQK PGQAPRLLIY GASSRATGIP  60
DRFSGSGSGT DFTLTISRLE PEDFAVYYCQ QYSSSPRTFG QGTKVEIK               108

SEQ ID NO: 17           moltype = AA  length = 12
FEATURE                 Location/Qualifiers
source                  1..12
                        mol_type = protein
                        organism = synthetic construct
SEQUENCE: 17
RASQSVSSIY LA                                                      12

SEQ ID NO: 18           moltype = AA  length = 7
FEATURE                 Location/Qualifiers
source                  1..7
                        mol_type = protein
                        organism = synthetic construct
SEQUENCE: 18
GASSRAT                                                            7

SEQ ID NO: 19           moltype = AA  length = 9
FEATURE                 Location/Qualifiers
source                  1..9
                        mol_type = protein
                        organism = synthetic construct
SEQUENCE: 19
QQYSSSPRT                                                          9

SEQ ID NO: 20           moltype =   length =
SEQUENCE: 20
000

SEQ ID NO: 21           moltype = AA  length = 702
FEATURE                 Location/Qualifiers
source                  1..702
                        mol_type = protein
                        organism = synthetic construct
SEQUENCE: 21
QVQLQESGPG LVKPSETLSL TCTVSGGSIS NYYWSWIRQP PGKGLEWIGY MYYSGITNYN  60
PSLKSRVTIS VDTSKNQFSL KLNSVTTADT AVYYCARERN GIDGMDVWGQ GTTVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
```

```
GNVFSCSVMH EALHNHYTQK SLSLSPGGGS GGSSSELTQD PAVSVALGQT VRITCQGDSL  480
RSYYASWYQQ KPGQAPVLVI YGKNNRPSGI PDRFSGSSSG NTASLTITGA QAEDEADYYC  540
NSRDSSGNHV VFGGGTKLTV LGGGGSGGGG SGGGGSGGGG SEVQLVQSGG GVERPGGSLR  600
LSCAASGFTF DDYGMSWVRQ APGKGLEWVS GINWNGGSTG YADSVKGRVT ISRDNAKNSL  660
YLQMNSLRAE DTAVYYCAKI LGAGRGWYFD LWGKGTTVTV SS                     702

SEQ ID NO: 22          moltype = AA  length = 118
FEATURE                Location/Qualifiers
source                 1..118
                       mol_type = protein
                       organism = synthetic construct
SEQUENCE: 22
QVQLQESGPG LVKPSETLSL TCTVSGGSIS NYYWSWIRQP PGKGLEWIGY MYYSGITNYN  60
PSLKSRVTIS VDTSKNQFSL KLNSVTTADT AVYYCARERN GIDGMDVWGQ GTTVTVSS    118

SEQ ID NO: 23          moltype = AA  length = 5
FEATURE                Location/Qualifiers
source                 1..5
                       mol_type = protein
                       organism = synthetic construct
SEQUENCE: 23
NYYWS                                                              5

SEQ ID NO: 24          moltype = AA  length = 16
FEATURE                Location/Qualifiers
source                 1..16
                       mol_type = protein
                       organism = synthetic construct
SEQUENCE: 24
YMYYSGITNY NPSLKS                                                  16

SEQ ID NO: 25          moltype = AA  length = 10
FEATURE                Location/Qualifiers
source                 1..10
                       mol_type = protein
                       organism = synthetic construct
SEQUENCE: 25
ERNGIDGMDV                                                         10

SEQ ID NO: 26          moltype = AA  length = 112
FEATURE                Location/Qualifiers
source                 1..112
                       mol_type = protein
                       organism = synthetic construct
SEQUENCE: 26
DIVMTQSPLS LPVTPGEPAS ISCRSSQSLL HSYGYNYLDW YLQKPGQSPQ LLIYLGSNRA  60
SGVPDRFSGS GSGTDFTLKI SRVEAEDFGI YYCMQALQTP ITFGQGTRLE IK          112

SEQ ID NO: 27          moltype = AA  length = 16
FEATURE                Location/Qualifiers
source                 1..16
                       mol_type = protein
                       organism = synthetic construct
SEQUENCE: 27
RSSQSLLHSY GYNYLD                                                  16

SEQ ID NO: 28          moltype = AA  length = 7
FEATURE                Location/Qualifiers
source                 1..7
                       mol_type = protein
                       organism = synthetic construct
SEQUENCE: 28
LGSNRAS                                                            7

SEQ ID NO: 29          moltype = AA  length = 9
FEATURE                Location/Qualifiers
source                 1..9
                       mol_type = protein
                       organism = synthetic construct
SEQUENCE: 29
MQALQTPIT                                                          9

SEQ ID NO: 30          moltype =   length =
SEQUENCE: 30
000

SEQ ID NO: 31          moltype = AA  length = 703
FEATURE                Location/Qualifiers
source                 1..703
```

```
                      mol_type = protein
                      organism = synthetic construct
SEQUENCE: 31
QVQLQESGPG LVKPSETLSL TCTVSGGSIS GYYWSWIRQS PGKGLEWIGY IYYSANTNYN  60
PSLKSRVTIS VDTSKNQFSL KLSSVTAADT AVYYCSRGGS GSYWAFDIWG QGTMVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGGG SGGSSSELTQ DPAVSVALGQ TVRITCQGDS  480
LRSYYASWYQ QKPGQAPVLV IYGKNNRPSG IPDRFSGSSS GNTASLTITG AQAEDEADYY  540
CNSRDSSGNH VVFGGGTKLT VLGGGGSGGG GSGGGGSGGG GSEVQLVQSG GGVERPGGSL  600
RLSCAASGFT FDDYGMSWVR QAPGKGLEWV SGINWNGGST GYADSVKGRV TISRDNAKNS  660
LYLQMNSLRA EDTAVYYCAK ILGAGRGWYF DLWGKGTTVT VSS                   703

SEQ ID NO: 32         moltype = AA  length = 119
FEATURE               Location/Qualifiers
source                1..119
                      mol_type = protein
                      organism = synthetic construct
SEQUENCE: 32
QVQLQESGPG LVKPSETLSL TCTVSGGSIS GYYWSWIRQS PGKGLEWIGY IYYSANTNYN  60
PSLKSRVTIS VDTSKNQFSL KLSSVTAADT AVYYCSRGGS GSYWAFDIWG QGTMVTVSS   119

SEQ ID NO: 33         moltype = AA  length = 5
FEATURE               Location/Qualifiers
source                1..5
                      mol_type = protein
                      organism = synthetic construct
SEQUENCE: 33
GYYWS                                                             5

SEQ ID NO: 34         moltype = AA  length = 16
FEATURE               Location/Qualifiers
source                1..16
                      mol_type = protein
                      organism = synthetic construct
SEQUENCE: 34
YIYYSANTNY NPSLKS                                                 16

SEQ ID NO: 35         moltype = AA  length = 11
FEATURE               Location/Qualifiers
source                1..11
                      mol_type = protein
                      organism = synthetic construct
SEQUENCE: 35
GGSGSYWAFD I                                                      11

SEQ ID NO: 36         moltype = AA  length = 112
FEATURE               Location/Qualifiers
source                1..112
                      mol_type = protein
                      organism = synthetic construct
SEQUENCE: 36
DIVMTQSPLS LPVTPGEPAS ISCRSSQSLM YSYGYNYLDW YLQKPGQSPQ LLIYLGSNRA  60
SGVPDRFSGS GSGTDFTLKI SRVEAEDVGI YYCMQALQTP PTFGQGTKVE IK         112

SEQ ID NO: 37         moltype = AA  length = 16
FEATURE               Location/Qualifiers
source                1..16
                      mol_type = protein
                      organism = synthetic construct
SEQUENCE: 37
RSSQSLMYSY GYNYLD                                                 16

SEQ ID NO: 38         moltype = AA  length = 7
FEATURE               Location/Qualifiers
source                1..7
                      mol_type = protein
                      organism = synthetic construct
SEQUENCE: 38
LGSNRAS                                                           7

SEQ ID NO: 39         moltype = AA  length = 9
FEATURE               Location/Qualifiers
source                1..9
                      mol_type = protein
                      organism = synthetic construct
```

```
SEQUENCE: 39
MQALQTPPT                                                               9

SEQ ID NO: 40          moltype =   length =
SEQUENCE: 40
000

SEQ ID NO: 41          moltype = AA  length = 702
FEATURE                Location/Qualifiers
source                 1..702
                       mol_type = protein
                       organism = synthetic construct
SEQUENCE: 41
QVQLQESGPG LVKPSETLSL TCTVSGGSIS GYYWSWIRQP AGKGLEWIGR IYTSGNTIYN  60
PSLKSRVTMS VDTSKNQFSL RLTSVTAADT AVYYCARGNP LATYFGYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGGGS GGSSSELTQD PAVSVALGQT VRITCQGDSL  480
RSYYASWYQQ KPGQAPVLVI YGKNNRPSGI PDRFSGSSSG NTASLTITGA QAEDEADYYC  540
NSRDSSGNHV VFGGGTKLTV LGGGGSGGGG SGGGGSGGGG SEVQLVQSGG GVERPGGSLR  600
LSCAASGFTF DDYGMSWVRQ APGKGLEWVS GINWNGGSTG YADSVKGRVT ISRDNAKNSL  660
YLQMNSLRAE DTAVYYCAKI LGAGRGWYFD LWGKGTTVTV SS                      702

SEQ ID NO: 42          moltype = AA  length = 118
FEATURE                Location/Qualifiers
source                 1..118
                       mol_type = protein
                       organism = synthetic construct
SEQUENCE: 42
QVQLQESGPG LVKPSETLSL TCTVSGGSIS GYYWSWIRQP AGKGLEWIGR IYTSGNTIYN  60
PSLKSRVTMS VDTSKNQFSL RLTSVTAADT AVYYCARGNP LATYFGYWGQ GTLVTVSS    118

SEQ ID NO: 43          moltype = AA  length = 5
FEATURE                Location/Qualifiers
source                 1..5
                       mol_type = protein
                       organism = synthetic construct
SEQUENCE: 43
GYYWS                                                                   5

SEQ ID NO: 44          moltype = AA  length = 16
FEATURE                Location/Qualifiers
source                 1..16
                       mol_type = protein
                       organism = synthetic construct
SEQUENCE: 44
RIYTSGNTIY NPSLKS                                                       16

SEQ ID NO: 45          moltype = AA  length = 10
FEATURE                Location/Qualifiers
source                 1..10
                       mol_type = protein
                       organism = synthetic construct
SEQUENCE: 45
GNPLATYFGY                                                              10

SEQ ID NO: 46          moltype = AA  length = 113
FEATURE                Location/Qualifiers
source                 1..113
                       mol_type = protein
                       organism = synthetic construct
SEQUENCE: 46
DIEMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST MYTFGQGTKL EIK         113

SEQ ID NO: 47          moltype = AA  length = 17
FEATURE                Location/Qualifiers
source                 1..17
                       mol_type = protein
                       organism = synthetic construct
SEQUENCE: 47
KSSQSVLYSS NNKNYLA                                                      17

SEQ ID NO: 48          moltype = AA  length = 7
FEATURE                Location/Qualifiers
source                 1..7
```

```
                          mol_type = protein
                          organism = synthetic construct
SEQUENCE: 48
WASTRES                                                                7

SEQ ID NO: 49             moltype = AA  length = 9
FEATURE                   Location/Qualifiers
source                    1..9
                          mol_type = protein
                          organism = synthetic construct
SEQUENCE: 49
QQYYSTMYT                                                              9

SEQ ID NO: 50             moltype =   length =
SEQUENCE: 50
000

SEQ ID NO: 51             moltype = AA  length = 702
FEATURE                   Location/Qualifiers
source                    1..702
                          mol_type = protein
                          organism = synthetic construct
SEQUENCE: 51
QVQLQESGPG LVKPSETLSL TCTVSGGSIS SYYWSWFRQP AGKGLEWIGR IYSSGSTNYN  60
PSLKSRVTMS VDTSKNQFSL KLSSVTAADT AVYYCARGMG VTGLFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGGGS GGSSSELTQD PAVSVALGQT VRITCQGDSL  480
RSYYASWYQQ KPGQAPVLVI YGKNNRPSGI PDRFSGSSSG NTASLTITGA QAEDEADYYC  540
NSRDSSGNHV VFGGGTKLTV LGGGGSGGGG SGGGGSGGGG SEVQLVQSGG GVERPGGSLR  600
LSCAASGFTF DDYGMSWVRQ APGKGLEWVS GINWNGGSTG YADSVKGRVT ISRDNAKNSL  660
YLQMNSLRAE DTAVYYCAKI LGAGRGWYFD LWGKGTTVTV SS                     702

SEQ ID NO: 52             moltype = AA  length = 118
FEATURE                   Location/Qualifiers
source                    1..118
                          mol_type = protein
                          organism = synthetic construct
SEQUENCE: 52
QVQLQESGPG LVKPSETLSL TCTVSGGSIS SYYWSWFRQP AGKGLEWIGR IYSSGSTNYN  60
PSLKSRVTMS VDTSKNQFSL KLSSVTAADT AVYYCARGMG VTGLFDYWGQ GTLVTVSS    118

SEQ ID NO: 53             moltype = AA  length = 5
FEATURE                   Location/Qualifiers
source                    1..5
                          mol_type = protein
                          organism = synthetic construct
SEQUENCE: 53
SYYWS                                                                  5

SEQ ID NO: 54             moltype = AA  length = 16
FEATURE                   Location/Qualifiers
source                    1..16
                          mol_type = protein
                          organism = synthetic construct
SEQUENCE: 54
RIYSSGSTNY NPSLKS                                                      16

SEQ ID NO: 55             moltype = AA  length = 10
FEATURE                   Location/Qualifiers
source                    1..10
                          mol_type = protein
                          organism = synthetic construct
SEQUENCE: 55
GMGVTGLFDY                                                             10

SEQ ID NO: 56             moltype = AA  length = 113
FEATURE                   Location/Qualifiers
source                    1..113
                          mol_type = protein
                          organism = synthetic construct
SEQUENCE: 56
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST MYTFGQGTKL EIK          113

SEQ ID NO: 57             moltype = AA  length = 17
```

```
FEATURE                 Location/Qualifiers
source                  1..17
                        mol_type = protein
                        organism = synthetic construct
SEQUENCE: 57
KSSQSVLYSS NNKNYLA                                              17

SEQ ID NO: 58           moltype = AA  length = 7
FEATURE                 Location/Qualifiers
source                  1..7
                        mol_type = protein
                        organism = synthetic construct
SEQUENCE: 58
WASTRES                                                         7

SEQ ID NO: 59           moltype = AA  length = 9
FEATURE                 Location/Qualifiers
source                  1..9
                        mol_type = protein
                        organism = synthetic construct
SEQUENCE: 59
QQYYSTMYT                                                       9

SEQ ID NO: 60           moltype =   length =
SEQUENCE: 60
000

SEQ ID NO: 61           moltype = AA  length = 704
FEATURE                 Location/Qualifiers
source                  1..704
                        mol_type = protein
                        organism = synthetic construct
SEQUENCE: 61
QVQLQESGPG LVKPSETLSL TCTVSGGSIN NYYWTWIRQP AGKGLEWIGR IYSSGSTNYT  60
PSLKSRVTMS VDTSKNQFSL KLSSVTAADT AVYFCAREGY NDGYGYFDHW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGG GSGGSSSELT QDPAVSVALG QTVRITCQGD  480
SLRSYYASWY QQKPGQAPVL VIYGKNNRPS GIPDRFSGSS SGNTASLTIT GAQAEDEADY  540
YCNSRDSSGN HVVFGGGTKL TVLGGGGSGG GGSGGGGSGG GGSEVQLVQS GGGVERPGGS  600
LRLSCAASGF TFDDYGMSWV RQAPGKGLEW VSGINWNGGS TGYADSVKGR VTISRDNAKN  660
SLYLQMNSLR AEDTAVYYCA KILGAGRGWY FDLWGKGTTV TVSS                  704

SEQ ID NO: 62           moltype = AA  length = 120
FEATURE                 Location/Qualifiers
source                  1..120
                        mol_type = protein
                        organism = synthetic construct
SEQUENCE: 62
QVQLQESGPG LVKPSETLSL TCTVSGGSIN NYYWTWIRQP AGKGLEWIGR IYSSGSTNYT  60
PSLKSRVTMS VDTSKNQFSL KLSSVTAADT AVYFCAREGY NDGYGYFDHW GQGTLVTVSS  120

SEQ ID NO: 63           moltype = AA  length = 5
FEATURE                 Location/Qualifiers
source                  1..5
                        mol_type = protein
                        organism = synthetic construct
SEQUENCE: 63
NYYWT                                                           5

SEQ ID NO: 64           moltype = AA  length = 16
FEATURE                 Location/Qualifiers
source                  1..16
                        mol_type = protein
                        organism = synthetic construct
SEQUENCE: 64
RIYSSGSTNY TPSLKS                                               16

SEQ ID NO: 65           moltype = AA  length = 12
FEATURE                 Location/Qualifiers
source                  1..12
                        mol_type = protein
                        organism = synthetic construct
SEQUENCE: 65
EGYNDGYGYF DH                                                   12
```

```
SEQ ID NO: 66           moltype = AA  length = 113
FEATURE                 Location/Qualifiers
source                  1..113
                        mol_type = protein
                        organism = synthetic construct
SEQUENCE: 66
DIVMTQSPDS LAVSLGERAT INCKSSQSVL YSSKNKNYLA WYQQKPGQPP KLLIYWASTR  60
ESGVPDRFSG SGSGTDFTLT ISSLQAEDVA VYYCQQYYST FRTFGQGTKV EIK         113

SEQ ID NO: 67           moltype = AA  length = 17
FEATURE                 Location/Qualifiers
source                  1..17
                        mol_type = protein
                        organism = synthetic construct
SEQUENCE: 67
KSSQSVLYSS KNKNYLA                                                 17

SEQ ID NO: 68           moltype = AA  length = 7
FEATURE                 Location/Qualifiers
source                  1..7
                        mol_type = protein
                        organism = synthetic construct
SEQUENCE: 68
WASTRES                                                            7

SEQ ID NO: 69           moltype = AA  length = 9
FEATURE                 Location/Qualifiers
source                  1..9
                        mol_type = protein
                        organism = synthetic construct
SEQUENCE: 69
QQYYSTFRT                                                          9

SEQ ID NO: 70           moltype =   length =
SEQUENCE: 70
000

SEQ ID NO: 71           moltype = AA  length = 249
FEATURE                 Location/Qualifiers
source                  1..249
                        mol_type = protein
                        organism = synthetic construct
SEQUENCE: 71
SSELTQDPAV SVALGQTVRI TCQGDSLRSY YASWYQQKPG QAPVLVIYGK NNRPSGIPDR  60
FSGSSSGNTA SLTITGAQAE DEADYYCNSR DSSGNHVVFG GGTKLTVLGG GGSGGGGSGG  120
GGSGGGGSEV QLVQSGGGVE RPGGSLRLSC AASGFTFDDY GMSWVRQAPG KGLEWVSGIN  180
WNGGSTGYAD SVKGRVTISR DNAKNSLYLQ MNSLRAEDTA VYYCAKILGA GRGWYFDLWG  240
KGTTVTVSS                                                          249

SEQ ID NO: 72           moltype = AA  length = 121
FEATURE                 Location/Qualifiers
source                  1..121
                        mol_type = protein
                        organism = synthetic construct
SEQUENCE: 72
EVQLVQSGGG VERPGGSLRL SCAASGFTFD DYGMSWVRQA PGKGLEWVSG INWNGGSTGY  60
ADSVKGRVTI SRDNAKNSLY LQMNSLRAED TAVYYCAKIL GAGRGWYFDL WGKGTTVTVS  120
S                                                                  121

SEQ ID NO: 73           moltype = AA  length = 5
FEATURE                 Location/Qualifiers
source                  1..5
                        mol_type = protein
                        organism = synthetic construct
SEQUENCE: 73
DYGMS                                                              5

SEQ ID NO: 74           moltype = AA  length = 17
FEATURE                 Location/Qualifiers
source                  1..17
                        mol_type = protein
                        organism = synthetic construct
SEQUENCE: 74
GINWNGGSTG YADSVKG                                                 17

SEQ ID NO: 75           moltype = AA  length = 12
FEATURE                 Location/Qualifiers
source                  1..12
                        mol_type = protein
```

```
                        organism = synthetic construct
SEQUENCE: 75
ILGAGRGWYF DL                                                    12

SEQ ID NO: 76           moltype = AA  length = 108
FEATURE                 Location/Qualifiers
source                  1..108
                        mol_type = protein
                        organism = synthetic construct
SEQUENCE: 76
SSELTQDPAV SVALGQTVRI TCQGDSLRSY YASWYQQKPG QAPVLVIYGK NNRPSGIPDR  60
FSGSSSGNTA SLTITGAQAE DEADYYCNSR DSSGNHVVFG GGTKLTVL               108

SEQ ID NO: 77           moltype = AA  length = 11
FEATURE                 Location/Qualifiers
source                  1..11
                        mol_type = protein
                        organism = synthetic construct
SEQUENCE: 77
QGDSLRSYYA S                                                     11

SEQ ID NO: 78           moltype = AA  length = 7
FEATURE                 Location/Qualifiers
source                  1..7
                        mol_type = protein
                        organism = synthetic construct
SEQUENCE: 78
GKNNRPS                                                          7

SEQ ID NO: 79           moltype = AA  length = 11
FEATURE                 Location/Qualifiers
source                  1..11
                        mol_type = protein
                        organism = synthetic construct
SEQUENCE: 79
NSRDSSGNHV V                                                     11

SEQ ID NO: 80           moltype = AA  length = 447
FEATURE                 Location/Qualifiers
source                  1..447
                        mol_type = protein
                        organism = synthetic construct
SEQUENCE: 80
QVQLQESGPG LVKPSETLSL TCTVSGGSIS SYYWSWIRQP PGKGLDWIGY IYYSRTTNYN  60
PSLKSRVTIS VDTSKNQFSL KLSSVTAADT AVYYCARARN GIDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 81           moltype = AA  length = 219
FEATURE                 Location/Qualifiers
source                  1..219
                        mol_type = protein
                        organism = synthetic construct
SEQUENCE: 81
DIVMTQSPLS LPVTPGEPAS ISCRSSQSLL HSYGYNYLDW YLQKPGQSPQ LLIYLGSNRA  60
SGVPDRFSGS GSGTDFTLKI SRVEAADVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                       219

SEQ ID NO: 82           moltype = AA  length = 444
FEATURE                 Location/Qualifiers
source                  1..444
                        mol_type = protein
                        organism = synthetic construct
SEQUENCE: 82
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARHS FFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSREEMTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                       444

SEQ ID NO: 83           moltype = AA  length = 215
```

```
FEATURE                Location/Qualifiers
source                 1..215
                       mol_type = protein
                       organism = synthetic construct
SEQUENCE: 83
EIVLTQSPGT LSLSPGERAT LSCRASQSVS SIYLAWYQQK PGQAPRLLIY GASSRATGIP  60
DRFSGSGSGT DFTLTISRLE PEDFAVYYCQ QYSSSPRTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 84          moltype = AA  length = 447
FEATURE                Location/Qualifiers
source                 1..447
                       mol_type = protein
                       organism = synthetic construct
SEQUENCE: 84
QVQLQESGPG LVKPSETLSL TCTVSGGSIS NYYWSWIRQP PGKGLEWIGY MYYSGITNYN  60
PSLKSRVTIS VDTSKNQFSL KLNSVTTADT AVYYCARERN GIDGMDVWGQ GTTVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 85          moltype = AA  length = 219
FEATURE                Location/Qualifiers
source                 1..219
                       mol_type = protein
                       organism = synthetic construct
SEQUENCE: 85
DIVMTQSPLS LPVTPGEPAS ISCRSSQSLL HSYGYNYLDW YLQKPGQSPQ LLIYLGSNRA  60
SGVPDRFSGS GSGTDFTLKI SRVEAEDFGI YYCMQALQTP ITFGQGTRLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 86          moltype = AA  length = 448
FEATURE                Location/Qualifiers
source                 1..448
                       mol_type = protein
                       organism = synthetic construct
SEQUENCE: 86
QVQLQESGPG LVKPSETLSL TCTVSGGSIS GYYWSWIRQS PGKGLEWIGY IYYSANTNYN  60
PSLKSRVTIS VDTSKNQFSL KLSSVTAADT AVYYCSRGGS GSYWAFDIWG QGTMVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 87          moltype = AA  length = 219
FEATURE                Location/Qualifiers
source                 1..219
                       mol_type = protein
                       organism = synthetic construct
SEQUENCE: 87
DIVMTQSPLS LPVTPGEPAS ISCRSSQSLM YSYGYNYLDW YLQKPGQSPQ LLIYLGSNRA  60
SGVPDRFSGS GSGTDFTLKI SRVEAEDVGI YYCMQALQTP PTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 88          moltype = AA  length = 447
FEATURE                Location/Qualifiers
source                 1..447
                       mol_type = protein
                       organism = synthetic construct
SEQUENCE: 88
QVQLQESGPG LVKPSETLSL TCTVSGGSIS GYYWSWIRQP AGKGLEWIGR IYTSGNTIYN  60
PSLKSRVTMS VDTSKNQFSL RLTSVTAADT AVYYCARGNP LATYFGYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 89          moltype = AA  length = 220
FEATURE                Location/Qualifiers
```

```
source                  1..220
                        mol_type = protein
                        organism = synthetic construct
SEQUENCE: 89
DIEMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST MYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 90           moltype = AA  length = 447
FEATURE                 Location/Qualifiers
source                  1..447
                        mol_type = protein
                        organism = synthetic construct
SEQUENCE: 90
QVQLQESGPG LVKPSETLSL TCTVSGGSIS SYYWSWFRQP AGKGLEWIGR IYSSGSTNYN  60
PSLKSRVTMS VDTSKNQFSL KLSSVTAADT AVYYCARGMG VTGLFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 91           moltype = AA  length = 220
FEATURE                 Location/Qualifiers
source                  1..220
                        mol_type = protein
                        organism = synthetic construct
SEQUENCE: 91
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST MYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 92           moltype = AA  length = 449
FEATURE                 Location/Qualifiers
source                  1..449
                        mol_type = protein
                        organism = synthetic construct
SEQUENCE: 92
QVQLQESGPG LVKPSETLSL TCTVSGGSIN NYYWTWIRQP AGKGLEWIGR IYSSGSTNYT  60
PSLKSRVTMS VDTSKNQFSL KLSSVTAADT AVYFCAREGY NDGYGYFDHW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 93           moltype = AA  length = 220
FEATURE                 Location/Qualifiers
source                  1..220
                        mol_type = protein
                        organism = synthetic construct
SEQUENCE: 93
DIVMTQSPDS LAVSLGERAT INCKSSQSVL YSSKNKNYLA WYQQKPGQPP KLLIYWASTR  60
ESGVPDRFSG SGSGTDFTLT ISSLQAEDVA VYYCQQYYST FRTFGQGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 94           moltype = AA  length = 6
FEATURE                 Location/Qualifiers
source                  1..6
                        mol_type = protein
                        organism = synthetic construct
SEQUENCE: 94
GGSGGS                                                             6

SEQ ID NO: 95           moltype = AA  length = 4
FEATURE                 Location/Qualifiers
source                  1..4
                        mol_type = protein
                        organism = synthetic construct
SEQUENCE: 95
GGGS                                                               4

SEQ ID NO: 96           moltype =   length =
SEQUENCE: 96
```

```
000

SEQ ID NO: 97           moltype =   length =
SEQUENCE: 97
000

SEQ ID NO: 98           moltype = AA  length = 829
FEATURE                 Location/Qualifiers
source                  1..829
                        mol_type = protein
                        organism = Homo sapiens
SEQUENCE: 98
MGLPRGPLAS LLLLQVCWLQ CAASEPCRAV FREAEVTLEA GGAEQEPGQA LGKVFMGCPG  60
QEPALFSTDN DDFTVRNGET VQERRSLKER NPLKIFPSKR ILRRHKRDWV VAPISVPENG  120
KGPFPQRLNQ LKSNKDRDTK IFYSITGPGA DSPPEGVFAV EKETGWLLLN KPLDREEIAK  180
YELFGHAVSE NGASVEDPMN ISIIVTDQND HKPKFTQDTF RGSVLEGVLP GTSVMQVTAT  240
DEDDAIYTYN GVVAYSIHSQ EPKDPHDLMF TIHRSTGTIS VISSGLDREK VPEYTLTIQA  300
TDMDGDGSTT TAVAVVEILD ANDNAPMFDP QKYEAHVPEN AVGHEVQRLT VTDLDAPNSP  360
AWRATYLIMG GDDGDHFTIT THPESNQGIL TTRKGLDFEA KNQHTLYVEV TNEAPFVLKL  420
PTSTATIVVH VEDVNEAPVF VPPSKVVEVQ EGIPTGEPVC VYTAEDPDKE NQKISYRILR  480
DPAGWLAMDP DSGQVTAVGT LDREDEQFVR NNIYEVMVLA MDNGSPPTTG TGTLLLTLID  540
VNDHGPVPEP RQITICNQSP VRQVLNITDK DLSPHTSPFQ AQLTDDSDIY WTAEVNEEGD  600
TVVLSLKKFL KQDTYDVHLS LSDHGNKEQL TVIRATVCDC HGHVETCPGP WKGGFILPVL  660
GAVLALLFLL LVLLLLVRKK RKIKEPLLLP EDDTRDNVFY YGEEGGGEED QDYDITQLHR  720
GLEARPEVVL RNDVAPTIIP TPMYRPRPAN PDEIGNFIIE NLKAANTDPT APPYDTLLVF  780
DYEGSGSDAA SLSSLTSSAS DQDQDYDYLN EWGSRFKKLA DMYGGGEDD             829

SEQ ID NO: 99           moltype = AA  length = 85
FEATURE                 Location/Qualifiers
source                  1..85
                        mol_type = protein
                        organism = Homo sapiens
SEQUENCE: 99
NQLKSNKDRD TKIFYSITGP GADSPPEGVF AVEKETGWLL LNKPLDREEI AKYELFGHAV  60
SENGASVEDP MNISIIVTDQ NDHKP                                       85

SEQ ID NO: 100          moltype = AA  length = 91
FEATURE                 Location/Qualifiers
source                  1..91
                        mol_type = protein
                        organism = Homo sapiens
SEQUENCE: 100
QVTATDEDDA IYTYNGVVAY SIHSQEPKDP HDLMFTIHRS TGTISVISSG LDREKVPEYT  60
LTIQATDMDG DGSTTTAVAV VEILDANDNA P                                91

SEQ ID NO: 101          moltype = AA  length = 7
FEATURE                 Location/Qualifiers
source                  1..7
                        mol_type = protein
                        organism = synthetic construct
SEQUENCE: 101
GGSISSY                                                           7

SEQ ID NO: 102          moltype = AA  length = 8
FEATURE                 Location/Qualifiers
source                  1..8
                        mol_type = protein
                        organism = synthetic construct
SEQUENCE: 102
GGSISSYY                                                          8

SEQ ID NO: 103          moltype = AA  length = 10
FEATURE                 Location/Qualifiers
source                  1..10
                        mol_type = protein
                        organism = synthetic construct
SEQUENCE: 103
GGSISSYYWS                                                        10

SEQ ID NO: 104          moltype = AA  length = 13
FEATURE                 Location/Qualifiers
source                  1..13
                        mol_type = protein
                        organism = synthetic construct
SEQUENCE: 104
TVSGGSISSY YWS                                                    13

SEQ ID NO: 105          moltype = AA  length = 5
FEATURE                 Location/Qualifiers
```

```
source                1..5
                      mol_type = protein
                      organism = synthetic construct
SEQUENCE: 105
YYSRT                                                                   5

SEQ ID NO: 106        moltype = AA  length = 7
FEATURE               Location/Qualifiers
source                1..7
                      mol_type = protein
                      organism = synthetic construct
SEQUENCE: 106
IYYSRTT                                                                 7

SEQ ID NO: 107        moltype = AA  length = 16
FEATURE               Location/Qualifiers
source                1..16
                      mol_type = protein
                      organism = synthetic construct
SEQUENCE: 107
YIYYSRTTNY NPSLKS                                                       16

SEQ ID NO: 108        moltype = AA  length = 9
FEATURE               Location/Qualifiers
source                1..9
                      mol_type = protein
                      organism = synthetic construct
SEQUENCE: 108
YIYYSRTTN                                                               9

SEQ ID NO: 109        moltype = AA  length = 10
FEATURE               Location/Qualifiers
source                1..10
                      mol_type = protein
                      organism = synthetic construct
SEQUENCE: 109
ARNGIDAFDI                                                              10

SEQ ID NO: 110        moltype = AA  length = 12
FEATURE               Location/Qualifiers
source                1..12
                      mol_type = protein
                      organism = synthetic construct
SEQUENCE: 110
ARARNGIDAF DI                                                           12

SEQ ID NO: 111        moltype = AA  length = 10
FEATURE               Location/Qualifiers
source                1..10
                      mol_type = protein
                      organism = synthetic construct
SEQUENCE: 111
ARNGIDAFDI                                                              10

SEQ ID NO: 112        moltype = AA  length = 12
FEATURE               Location/Qualifiers
source                1..12
                      mol_type = protein
                      organism = synthetic construct
SEQUENCE: 112
ARARNGIDAF DI                                                           12

SEQ ID NO: 113        moltype = AA  length = 16
FEATURE               Location/Qualifiers
source                1..16
                      mol_type = protein
                      organism = synthetic construct
SEQUENCE: 113
RSSQSLLHSY GYNYLD                                                       16

SEQ ID NO: 114        moltype = AA  length = 11
FEATURE               Location/Qualifiers
source                1..11
                      mol_type = protein
                      organism = synthetic construct
SEQUENCE: 114
QSLLHSYGYN Y                                                            11

SEQ ID NO: 115        moltype = AA  length = 16
```

```
FEATURE                 Location/Qualifiers
source                  1..16
                        mol_type = protein
                        organism = synthetic construct
SEQUENCE: 115
RSSQSLLHSY GYNYLD                                                       16

SEQ ID NO: 116          moltype = AA  length = 16
FEATURE                 Location/Qualifiers
source                  1..16
                        mol_type = protein
                        organism = synthetic construct
SEQUENCE: 116
RSSQSLLHSY GYNYLD                                                       16

SEQ ID NO: 117          moltype = AA  length = 7
FEATURE                 Location/Qualifiers
source                  1..7
                        mol_type = protein
                        organism = synthetic construct
SEQUENCE: 117
LGSNRAS                                                                 7

SEQ ID NO: 118          moltype =   length =
SEQUENCE: 118
000

SEQ ID NO: 119          moltype = AA  length = 7
FEATURE                 Location/Qualifiers
source                  1..7
                        mol_type = protein
                        organism = synthetic construct
SEQUENCE: 119
LGSNRAS                                                                 7

SEQ ID NO: 120          moltype = AA  length = 8
FEATURE                 Location/Qualifiers
source                  1..8
                        mol_type = protein
                        organism = synthetic construct
SEQUENCE: 120
YLGSNRAS                                                                8

SEQ ID NO: 121          moltype = AA  length = 9
FEATURE                 Location/Qualifiers
source                  1..9
                        mol_type = protein
                        organism = synthetic construct
SEQUENCE: 121
MQALQTPLT                                                               9

SEQ ID NO: 122          moltype = AA  length = 9
FEATURE                 Location/Qualifiers
source                  1..9
                        mol_type = protein
                        organism = synthetic construct
SEQUENCE: 122
MQALQTPLT                                                               9

SEQ ID NO: 123          moltype = AA  length = 9
FEATURE                 Location/Qualifiers
source                  1..9
                        mol_type = protein
                        organism = synthetic construct
SEQUENCE: 123
MQALQTPLT                                                               9

SEQ ID NO: 124          moltype = AA  length = 9
FEATURE                 Location/Qualifiers
source                  1..9
                        mol_type = protein
                        organism = synthetic construct
SEQUENCE: 124
MQALQTPLT                                                               9

SEQ ID NO: 125          moltype = AA  length = 7
FEATURE                 Location/Qualifiers
source                  1..7
                        mol_type = protein
```

```
                        organism = synthetic construct
SEQUENCE: 125
GYSFTSY                                                                   7

SEQ ID NO: 126          moltype = AA  length = 8
FEATURE                 Location/Qualifiers
source                  1..8
                        mol_type = protein
                        organism = synthetic construct
SEQUENCE: 126
GYSFTSYW                                                                  8

SEQ ID NO: 127          moltype = AA  length = 10
FEATURE                 Location/Qualifiers
source                  1..10
                        mol_type = protein
                        organism = synthetic construct
SEQUENCE: 127
GYSFTSYWIG                                                                10

SEQ ID NO: 128          moltype = AA  length = 13
FEATURE                 Location/Qualifiers
source                  1..13
                        mol_type = protein
                        organism = synthetic construct
SEQUENCE: 128
KGSGYSFTSY WIG                                                            13

SEQ ID NO: 129          moltype = AA  length = 6
FEATURE                 Location/Qualifiers
source                  1..6
                        mol_type = protein
                        organism = synthetic construct
SEQUENCE: 129
YPGDSD                                                                    6

SEQ ID NO: 130          moltype = AA  length = 8
FEATURE                 Location/Qualifiers
source                  1..8
                        mol_type = protein
                        organism = synthetic construct
SEQUENCE: 130
IYPGDSDT                                                                  8

SEQ ID NO: 131          moltype = AA  length = 17
FEATURE                 Location/Qualifiers
source                  1..17
                        mol_type = protein
                        organism = synthetic construct
SEQUENCE: 131
IIYPGDSDTR YSPSFQG                                                        17

SEQ ID NO: 132          moltype = AA  length = 10
FEATURE                 Location/Qualifiers
source                  1..10
                        mol_type = protein
                        organism = synthetic construct
SEQUENCE: 132
IIYPGDSDTR                                                                10

SEQ ID NO: 133          moltype = AA  length = 6
FEATURE                 Location/Qualifiers
source                  1..6
                        mol_type = protein
                        organism = synthetic construct
SEQUENCE: 133
HSFFDY                                                                    6

SEQ ID NO: 134          moltype = AA  length = 8
FEATURE                 Location/Qualifiers
source                  1..8
                        mol_type = protein
                        organism = synthetic construct
SEQUENCE: 134
ARHSFFDY                                                                  8

SEQ ID NO: 135          moltype = AA  length = 6
FEATURE                 Location/Qualifiers
source                  1..6
```

```
                        mol_type = protein
                        organism = synthetic construct
SEQUENCE: 135
HSFFDY                                                          6

SEQ ID NO: 136          moltype = AA  length = 8
FEATURE                 Location/Qualifiers
source                  1..8
                        mol_type = protein
                        organism = synthetic construct
SEQUENCE: 136
ARHSFFDY                                                        8

SEQ ID NO: 137          moltype = AA  length = 12
FEATURE                 Location/Qualifiers
source                  1..12
                        mol_type = protein
                        organism = synthetic construct
SEQUENCE: 137
RASQSVSSIY LA                                                   12

SEQ ID NO: 138          moltype = AA  length = 7
FEATURE                 Location/Qualifiers
source                  1..7
                        mol_type = protein
                        organism = synthetic construct
SEQUENCE: 138
QSVSSIY                                                         7

SEQ ID NO: 139          moltype = AA  length = 12
FEATURE                 Location/Qualifiers
source                  1..12
                        mol_type = protein
                        organism = synthetic construct
SEQUENCE: 139
RASQSVSSIY LA                                                   12

SEQ ID NO: 140          moltype = AA  length = 12
FEATURE                 Location/Qualifiers
source                  1..12
                        mol_type = protein
                        organism = synthetic construct
SEQUENCE: 140
RASQSVSSIY LA                                                   12

SEQ ID NO: 141          moltype = AA  length = 7
FEATURE                 Location/Qualifiers
source                  1..7
                        mol_type = protein
                        organism = synthetic construct
SEQUENCE: 141
GASSRAT                                                         7

SEQ ID NO: 142          moltype =   length =
SEQUENCE: 142
000

SEQ ID NO: 143          moltype = AA  length = 7
FEATURE                 Location/Qualifiers
source                  1..7
                        mol_type = protein
                        organism = synthetic construct
SEQUENCE: 143
GASSRAT                                                         7

SEQ ID NO: 144          moltype = AA  length = 8
FEATURE                 Location/Qualifiers
source                  1..8
                        mol_type = protein
                        organism = synthetic construct
SEQUENCE: 144
YGASSRAT                                                        8

SEQ ID NO: 145          moltype = AA  length = 9
FEATURE                 Location/Qualifiers
source                  1..9
                        mol_type = protein
                        organism = synthetic construct
SEQUENCE: 145
```

```
QQYSSSPRT                                                   9

SEQ ID NO: 146          moltype = AA  length = 9
FEATURE                 Location/Qualifiers
source                  1..9
                        mol_type = protein
                        organism = synthetic construct
SEQUENCE: 146
QQYSSSPRT                                                   9

SEQ ID NO: 147          moltype = AA  length = 9
FEATURE                 Location/Qualifiers
source                  1..9
                        mol_type = protein
                        organism = synthetic construct
SEQUENCE: 147
QQYSSSPRT                                                   9

SEQ ID NO: 148          moltype = AA  length = 9
FEATURE                 Location/Qualifiers
source                  1..9
                        mol_type = protein
                        organism = synthetic construct
SEQUENCE: 148
QQYSSSPRT                                                   9

SEQ ID NO: 149          moltype = AA  length = 7
FEATURE                 Location/Qualifiers
source                  1..7
                        mol_type = protein
                        organism = synthetic construct
SEQUENCE: 149
GGSISNY                                                     7

SEQ ID NO: 150          moltype = AA  length = 8
FEATURE                 Location/Qualifiers
source                  1..8
                        mol_type = protein
                        organism = synthetic construct
SEQUENCE: 150
GGSISNYY                                                    8

SEQ ID NO: 151          moltype = AA  length = 10
FEATURE                 Location/Qualifiers
source                  1..10
                        mol_type = protein
                        organism = synthetic construct
SEQUENCE: 151
GGSISNYYWS                                                  10

SEQ ID NO: 152          moltype = AA  length = 13
FEATURE                 Location/Qualifiers
source                  1..13
                        mol_type = protein
                        organism = synthetic construct
SEQUENCE: 152
TVSGGSISNY YWS                                              13

SEQ ID NO: 153          moltype = AA  length = 5
FEATURE                 Location/Qualifiers
source                  1..5
                        mol_type = protein
                        organism = synthetic construct
SEQUENCE: 153
YYSGI                                                       5

SEQ ID NO: 154          moltype = AA  length = 7
FEATURE                 Location/Qualifiers
source                  1..7
                        mol_type = protein
                        organism = synthetic construct
SEQUENCE: 154
MYYSGIT                                                     7

SEQ ID NO: 155          moltype = AA  length = 16
FEATURE                 Location/Qualifiers
source                  1..16
                        mol_type = protein
                        organism = synthetic construct
```

```
SEQUENCE: 155
YMYYSGITNY NPSLKS                                              16

SEQ ID NO: 156          moltype = AA  length = 9
FEATURE                 Location/Qualifiers
source                  1..9
                        mol_type = protein
                        organism = synthetic construct
SEQUENCE: 156
YMYYSGITN                                                      9

SEQ ID NO: 157          moltype = AA  length = 10
FEATURE                 Location/Qualifiers
source                  1..10
                        mol_type = protein
                        organism = synthetic construct
SEQUENCE: 157
ERNGIDGMDV                                                     10

SEQ ID NO: 158          moltype = AA  length = 12
FEATURE                 Location/Qualifiers
source                  1..12
                        mol_type = protein
                        organism = synthetic construct
SEQUENCE: 158
ARERNGIDGM DV                                                  12

SEQ ID NO: 159          moltype = AA  length = 10
FEATURE                 Location/Qualifiers
source                  1..10
                        mol_type = protein
                        organism = synthetic construct
SEQUENCE: 159
ERNGIDGMDV                                                     10

SEQ ID NO: 160          moltype = AA  length = 12
FEATURE                 Location/Qualifiers
source                  1..12
                        mol_type = protein
                        organism = synthetic construct
SEQUENCE: 160
ARERNGIDGM DV                                                  12

SEQ ID NO: 161          moltype = AA  length = 16
FEATURE                 Location/Qualifiers
source                  1..16
                        mol_type = protein
                        organism = synthetic construct
SEQUENCE: 161
RSSQSLLHSY GYNYLD                                              16

SEQ ID NO: 162          moltype = AA  length = 11
FEATURE                 Location/Qualifiers
source                  1..11
                        mol_type = protein
                        organism = synthetic construct
SEQUENCE: 162
QSLLHSYGYN Y                                                   11

SEQ ID NO: 163          moltype = AA  length = 16
FEATURE                 Location/Qualifiers
source                  1..16
                        mol_type = protein
                        organism = synthetic construct
SEQUENCE: 163
RSSQSLLHSY GYNYLD                                              16

SEQ ID NO: 164          moltype = AA  length = 16
FEATURE                 Location/Qualifiers
source                  1..16
                        mol_type = protein
                        organism = synthetic construct
SEQUENCE: 164
RSSQSLLHSY GYNYLD                                              16

SEQ ID NO: 165          moltype = AA  length = 7
FEATURE                 Location/Qualifiers
source                  1..7
                        mol_type = protein
```

```
                        organism = synthetic construct
SEQUENCE: 165
LGSNRAS                                                                   7

SEQ ID NO: 166          moltype =   length =
SEQUENCE: 166
000

SEQ ID NO: 167          moltype = AA  length = 7
FEATURE                 Location/Qualifiers
source                  1..7
                        mol_type = protein
                        organism = synthetic construct
SEQUENCE: 167
LGSNRAS                                                                   7

SEQ ID NO: 168          moltype = AA  length = 8
FEATURE                 Location/Qualifiers
source                  1..8
                        mol_type = protein
                        organism = synthetic construct
SEQUENCE: 168
YLGSNRAS                                                                  8

SEQ ID NO: 169          moltype = AA  length = 9
FEATURE                 Location/Qualifiers
source                  1..9
                        mol_type = protein
                        organism = synthetic construct
SEQUENCE: 169
MQALQTPIT                                                                 9

SEQ ID NO: 170          moltype = AA  length = 9
FEATURE                 Location/Qualifiers
source                  1..9
                        mol_type = protein
                        organism = synthetic construct
SEQUENCE: 170
MQALQTPIT                                                                 9

SEQ ID NO: 171          moltype = AA  length = 9
FEATURE                 Location/Qualifiers
source                  1..9
                        mol_type = protein
                        organism = synthetic construct
SEQUENCE: 171
MQALQTPIT                                                                 9

SEQ ID NO: 172          moltype = AA  length = 9
FEATURE                 Location/Qualifiers
source                  1..9
                        mol_type = protein
                        organism = synthetic construct
SEQUENCE: 172
MQALQTPIT                                                                 9

SEQ ID NO: 173          moltype = AA  length = 7
FEATURE                 Location/Qualifiers
source                  1..7
                        mol_type = protein
                        organism = synthetic construct
SEQUENCE: 173
GGSISGY                                                                   7

SEQ ID NO: 174          moltype = AA  length = 8
FEATURE                 Location/Qualifiers
source                  1..8
                        mol_type = protein
                        organism = synthetic construct
SEQUENCE: 174
GGSISGYY                                                                  8

SEQ ID NO: 175          moltype = AA  length = 10
FEATURE                 Location/Qualifiers
source                  1..10
                        mol_type = protein
                        organism = synthetic construct
SEQUENCE: 175
GGSISGYYWS                                                                10
```

```
SEQ ID NO: 176          moltype = AA  length = 13
FEATURE                 Location/Qualifiers
source                  1..13
                        mol_type = protein
                        organism = synthetic construct
SEQUENCE: 176
TVSGGSISGY YWS                                                      13

SEQ ID NO: 177          moltype = AA  length = 5
FEATURE                 Location/Qualifiers
source                  1..5
                        mol_type = protein
                        organism = synthetic construct
SEQUENCE: 177
YYSAN                                                               5

SEQ ID NO: 178          moltype = AA  length = 7
FEATURE                 Location/Qualifiers
source                  1..7
                        mol_type = protein
                        organism = synthetic construct
SEQUENCE: 178
IYYSANT                                                             7

SEQ ID NO: 179          moltype = AA  length = 16
FEATURE                 Location/Qualifiers
source                  1..16
                        mol_type = protein
                        organism = synthetic construct
SEQUENCE: 179
YIYYSANTNY NPSLKS                                                   16

SEQ ID NO: 180          moltype = AA  length = 9
FEATURE                 Location/Qualifiers
source                  1..9
                        mol_type = protein
                        organism = synthetic construct
SEQUENCE: 180
YIYYSANTN                                                           9

SEQ ID NO: 181          moltype = AA  length = 11
FEATURE                 Location/Qualifiers
source                  1..11
                        mol_type = protein
                        organism = synthetic construct
SEQUENCE: 181
GGSGSYWAFD I                                                        11

SEQ ID NO: 182          moltype = AA  length = 13
FEATURE                 Location/Qualifiers
source                  1..13
                        mol_type = protein
                        organism = synthetic construct
SEQUENCE: 182
SRGGSGSYWA FDI                                                      13

SEQ ID NO: 183          moltype = AA  length = 11
FEATURE                 Location/Qualifiers
source                  1..11
                        mol_type = protein
                        organism = synthetic construct
SEQUENCE: 183
GGSGSYWAFD I                                                        11

SEQ ID NO: 184          moltype = AA  length = 13
FEATURE                 Location/Qualifiers
source                  1..13
                        mol_type = protein
                        organism = synthetic construct
SEQUENCE: 184
SRGGSGSYWA FDI                                                      13

SEQ ID NO: 185          moltype = AA  length = 16
FEATURE                 Location/Qualifiers
source                  1..16
                        mol_type = protein
                        organism = synthetic construct
SEQUENCE: 185
```

```
RSSQSLMYSY GYNYLD                                                16

SEQ ID NO: 186          moltype = AA  length = 11
FEATURE                 Location/Qualifiers
source                  1..11
                        mol_type = protein
                        organism = synthetic construct
SEQUENCE: 186
QSLMYSYGYN Y                                                     11

SEQ ID NO: 187          moltype = AA  length = 16
FEATURE                 Location/Qualifiers
source                  1..16
                        mol_type = protein
                        organism = synthetic construct
SEQUENCE: 187
RSSQSLMYSY GYNYLD                                                16

SEQ ID NO: 188          moltype = AA  length = 16
FEATURE                 Location/Qualifiers
source                  1..16
                        mol_type = protein
                        organism = synthetic construct
SEQUENCE: 188
RSSQSLMYSY GYNYLD                                                16

SEQ ID NO: 189          moltype = AA  length = 7
FEATURE                 Location/Qualifiers
source                  1..7
                        mol_type = protein
                        organism = synthetic construct
SEQUENCE: 189
LGSNRAS                                                          7

SEQ ID NO: 190          moltype =   length =
SEQUENCE: 190
000

SEQ ID NO: 191          moltype = AA  length = 7
FEATURE                 Location/Qualifiers
source                  1..7
                        mol_type = protein
                        organism = synthetic construct
SEQUENCE: 191
LGSNRAS                                                          7

SEQ ID NO: 192          moltype = AA  length = 8
FEATURE                 Location/Qualifiers
source                  1..8
                        mol_type = protein
                        organism = synthetic construct
SEQUENCE: 192
YLGSNRAS                                                         8

SEQ ID NO: 193          moltype = AA  length = 9
FEATURE                 Location/Qualifiers
source                  1..9
                        mol_type = protein
                        organism = synthetic construct
SEQUENCE: 193
MQALQTPPT                                                        9

SEQ ID NO: 194          moltype = AA  length = 9
FEATURE                 Location/Qualifiers
source                  1..9
                        mol_type = protein
                        organism = synthetic construct
SEQUENCE: 194
MQALQTPPT                                                        9

SEQ ID NO: 195          moltype = AA  length = 9
FEATURE                 Location/Qualifiers
source                  1..9
                        mol_type = protein
                        organism = synthetic construct
SEQUENCE: 195
MQALQTPPT                                                        9

SEQ ID NO: 196          moltype = AA  length = 9
```

```
FEATURE                Location/Qualifiers
source                 1..9
                       mol_type = protein
                       organism = synthetic construct
SEQUENCE: 196
MQALQTPPT                                                    9

SEQ ID NO: 197         moltype = AA  length = 7
FEATURE                Location/Qualifiers
source                 1..7
                       mol_type = protein
                       organism = synthetic construct
SEQUENCE: 197
GFTFDDY                                                      7

SEQ ID NO: 198         moltype = AA  length = 8
FEATURE                Location/Qualifiers
source                 1..8
                       mol_type = protein
                       organism = synthetic construct
SEQUENCE: 198
GFTFDDYG                                                     8

SEQ ID NO: 199         moltype = AA  length = 10
FEATURE                Location/Qualifiers
source                 1..10
                       mol_type = protein
                       organism = synthetic construct
SEQUENCE: 199
GFTFDDYGMS                                                   10

SEQ ID NO: 200         moltype = AA  length = 13
FEATURE                Location/Qualifiers
source                 1..13
                       mol_type = protein
                       organism = synthetic construct
SEQUENCE: 200
AASGFTFDDY GMS                                               13

SEQ ID NO: 201         moltype = AA  length = 6
FEATURE                Location/Qualifiers
source                 1..6
                       mol_type = protein
                       organism = synthetic construct
SEQUENCE: 201
NWNGGS                                                       6

SEQ ID NO: 202         moltype = AA  length = 8
FEATURE                Location/Qualifiers
source                 1..8
                       mol_type = protein
                       organism = synthetic construct
SEQUENCE: 202
INWNGGST                                                     8

SEQ ID NO: 203         moltype = AA  length = 17
FEATURE                Location/Qualifiers
source                 1..17
                       mol_type = protein
                       organism = synthetic construct
SEQUENCE: 203
GINWNGGSTG YADSVKG                                           17

SEQ ID NO: 204         moltype = AA  length = 10
FEATURE                Location/Qualifiers
source                 1..10
                       mol_type = protein
                       organism = synthetic construct
SEQUENCE: 204
GINWNGGSTG                                                   10

SEQ ID NO: 205         moltype = AA  length = 12
FEATURE                Location/Qualifiers
source                 1..12
                       mol_type = protein
                       organism = synthetic construct
SEQUENCE: 205
ILGAGRGWYF DL                                                12
```

```
SEQ ID NO: 206          moltype = AA  length = 14
FEATURE                 Location/Qualifiers
source                  1..14
                        mol_type = protein
                        organism = synthetic construct
SEQUENCE: 206
AKILGAGRGW YFDL                                                    14

SEQ ID NO: 207          moltype = AA  length = 12
FEATURE                 Location/Qualifiers
source                  1..12
                        mol_type = protein
                        organism = synthetic construct
SEQUENCE: 207
ILGAGRGWYF DL                                                      12

SEQ ID NO: 208          moltype = AA  length = 14
FEATURE                 Location/Qualifiers
source                  1..14
                        mol_type = protein
                        organism = synthetic construct
SEQUENCE: 208
AKILGAGRGW YFDL                                                    14

SEQ ID NO: 209          moltype = AA  length = 11
FEATURE                 Location/Qualifiers
source                  1..11
                        mol_type = protein
                        organism = synthetic construct
SEQUENCE: 209
QGDSLRSYYA S                                                       11

SEQ ID NO: 210          moltype = AA  length = 6
FEATURE                 Location/Qualifiers
source                  1..6
                        mol_type = protein
                        organism = synthetic construct
SEQUENCE: 210
SLRSYY                                                             6

SEQ ID NO: 211          moltype = AA  length = 11
FEATURE                 Location/Qualifiers
source                  1..11
                        mol_type = protein
                        organism = synthetic construct
SEQUENCE: 211
QGDSLRSYYA S                                                       11

SEQ ID NO: 212          moltype = AA  length = 11
FEATURE                 Location/Qualifiers
source                  1..11
                        mol_type = protein
                        organism = synthetic construct
SEQUENCE: 212
QGDSLRSYYA S                                                       11

SEQ ID NO: 213          moltype = AA  length = 7
FEATURE                 Location/Qualifiers
source                  1..7
                        mol_type = protein
                        organism = synthetic construct
SEQUENCE: 213
GKNNRPS                                                            7

SEQ ID NO: 214          moltype =   length =
SEQUENCE: 214
000

SEQ ID NO: 215          moltype = AA  length = 7
FEATURE                 Location/Qualifiers
source                  1..7
                        mol_type = protein
                        organism = synthetic construct
SEQUENCE: 215
GKNNRPS                                                            7

SEQ ID NO: 216          moltype = AA  length = 8
FEATURE                 Location/Qualifiers
source                  1..8
```

```
                        mol_type = protein
                        organism = synthetic construct
SEQUENCE: 216
YGKNNRPS                                                   8

SEQ ID NO: 217          moltype = AA  length = 11
FEATURE                 Location/Qualifiers
source                  1..11
                        mol_type = protein
                        organism = synthetic construct
SEQUENCE: 217
NSRDSSGNHV V                                               11

SEQ ID NO: 218          moltype = AA  length = 11
FEATURE                 Location/Qualifiers
source                  1..11
                        mol_type = protein
                        organism = synthetic construct
SEQUENCE: 218
NSRDSSGNHV V                                               11

SEQ ID NO: 219          moltype = AA  length = 11
FEATURE                 Location/Qualifiers
source                  1..11
                        mol_type = protein
                        organism = synthetic construct
SEQUENCE: 219
NSRDSSGNHV V                                               11

SEQ ID NO: 220          moltype = AA  length = 11
FEATURE                 Location/Qualifiers
source                  1..11
                        mol_type = protein
                        organism = synthetic construct
SEQUENCE: 220
NSRDSSGNHV V                                               11

SEQ ID NO: 221          moltype = AA  length = 7
FEATURE                 Location/Qualifiers
source                  1..7
                        mol_type = protein
                        organism = synthetic construct
SEQUENCE: 221
GGGSGGS                                                    7

SEQ ID NO: 222          moltype = AA  length = 5
FEATURE                 Location/Qualifiers
source                  1..5
                        mol_type = protein
                        organism = synthetic construct
SEQUENCE: 222
GGGGS                                                      5

SEQ ID NO: 223          moltype = AA  length = 7
FEATURE                 Location/Qualifiers
source                  1..7
                        mol_type = protein
                        organism = synthetic construct
SEQUENCE: 223
SGGSGGS                                                    7

SEQ ID NO: 224          moltype = AA  length = 9
FEATURE                 Location/Qualifiers
source                  1..9
                        mol_type = protein
                        organism = synthetic construct
SEQUENCE: 224
GGGGCGGGS                                                  9

SEQ ID NO: 225          moltype = AA  length = 9
FEATURE                 Location/Qualifiers
source                  1..9
                        mol_type = protein
                        organism = synthetic construct
SEQUENCE: 225
GGGGSGGGS                                                  9

SEQ ID NO: 226          moltype = AA  length = 10
FEATURE                 Location/Qualifiers
```

-continued

```
source                  1..10
                        mol_type = protein
                        organism = synthetic construct
SEQUENCE: 226
GGGGSGGGGS                                                     10

SEQ ID NO: 227          moltype = AA  length = 15
FEATURE                 Location/Qualifiers
source                  1..15
                        mol_type = protein
                        organism = synthetic construct
SEQUENCE: 227
GGGGSGGGGS GGGGS                                               15

SEQ ID NO: 228          moltype = AA  length = 18
FEATURE                 Location/Qualifiers
source                  1..18
                        mol_type = protein
                        organism = synthetic construct
SEQUENCE: 228
GGGGSGGGGS GGGGGGGS                                            18

SEQ ID NO: 229          moltype = AA  length = 25
FEATURE                 Location/Qualifiers
source                  1..25
                        mol_type = protein
                        organism = synthetic construct
SEQUENCE: 229
GGGGSGGGGS GGGGSGGGGS GGGGS                                    25

SEQ ID NO: 230          moltype = AA  length = 30
FEATURE                 Location/Qualifiers
source                  1..30
                        mol_type = protein
                        organism = synthetic construct
SEQUENCE: 230
GGGGSGGGGS GGGGSGGGGS GGGGSGGGGS                               30

SEQ ID NO: 231          moltype = AA  length = 35
FEATURE                 Location/Qualifiers
source                  1..35
                        mol_type = protein
                        organism = synthetic construct
SEQUENCE: 231
GGGGSGGGGS GGGGSGGGGS GGGGSGGGGS GGGGS                         35

SEQ ID NO: 232          moltype = AA  length = 20
FEATURE                 Location/Qualifiers
source                  1..20
                        mol_type = protein
                        organism = synthetic construct
SEQUENCE: 232
GGGGSGGGGS GGGGSGGGGS                                          20
```

BINDING MOLECULES FOR THE TREATMENT OF CANCER

RELATED APPLICATION DISCLOSURE

This application claims priority to EP Application Serial No. 22185100.9 filed Jul. 15, 2022, which is hereby incorporated by reference in its entirety.

SEQUENCE DISCLOSURE

This application includes, as part of its disclosure, a "Sequence Listing XML" pursuant to 37 C.F.R. § 1.831(a) which is submitted in XML file format via the USPTO patent electronic filing system in a file named "12-0487-US-1_2023-07-13-Sequence-Listing.xml", created on Jun. 26, 2023, and having a size of 205,082 bytes, which is hereby incorporated by reference herein in its entirety.

FIELD OF THE INVENTION

The present invention relates to novel binding molecules. The invention specifically relates to novel binding molecules that bind to TNF-related apoptosis-inducing ligand receptor 2 (TRAILR2) and cadherin-3 (CDH3). The invention also relates to nucleic acids encoding such binding molecules; to methods for preparing such binding molecules; to host cells expressing or capable of expressing such binding molecules; to compositions comprising such binding molecules; and to uses of such binding molecules or such compositions, in particular for therapeutic purposes in the field of cancer diseases.

BACKGROUND OF THE INVENTION

Cancer is a disease characterised by abnormal localised cell growth with the potential to spread throughout the body. It is a serious disease and the second most common cause of death in the developed world.

In the past, the most frequent means of treating tumorous cancers are through surgery, radiation treatment, and the use of chemotherapeutic drugs or immunotherapy. Although in recent years there have been advances in the treatment of certain cancers, there remains still a need for improvements in the treatment of this disease.

Antibody-based biological molecules offer the potential to be powerful therapeutic agents for the treatment of cancer. Antibodies are designed to recognize and bind to specific proteins on the surface of cells (their target antigens), and such proteins may be present only on the surface of specific cancer cells or on immune cells. This binding can provoke a number of different biological responses, depending on the function of their target antigen protein and also the structure of the antibody itself and its binding site. For example, some antibodies trigger the immune system to attack and kill cancer cells, either by attracting immune cells to the cancer cells or by directly influencing the activity of the immune system itself. Other types of antibodies have drugs or radioactive particles attached to them and hence deliver these therapeutics to the cancer cell. A further type of antibodies that bind to cancer cells either activates or inhibits specific mechanisms that can reduce cell division or even kill tumor cells.

Apoptosis (or programmed cell death) is a controlled cellular mechanism, where the organism maintains cellular homeostasis in normal tissue compartments and eliminates disordered cells.

There are two major signalling pathways leading to apoptosis in mammalian cells: the intrinsic pathway and the extrinsic pathway. The intrinsic pathway is initiated at the mitochondrial level and plays a substantial role in chemo-therapy- or irradiation-induced cell death. By contrast, the extrinsic death pathway is initiated through death receptor-mediated signals on the cell surface.

Cell death induced through the extrinsic pathway has been studied extensively following signals mediated by various members of tumor necrosis factor (TNF) receptor superfamily. The TNF superfamily is characterized by a sequence of two to five cysteine-rich extracellular repeats. The death receptors belonging to the TNF superfamily share a homologous, intracellular death domain of about 80 amino acids, which is essential for the transduction of apoptotic signals. TNF-related apoptosis-inducing ligand (TRAIL) is a natural protein ligand which interacts with two types of receptors: death receptors triggering- and decoy receptors inhibiting-TRAIL-induced apoptosis. To date, four human receptors specific for TRAIL have been identified: the death receptors, DR4 (DR4/TRAIL receptor 1/TRAILR1) and DR5 (TRAIL receptor 2/TRAIL-R2/KILLER), and the decoy receptors, DcR1/TRAILR3/TRID and DcR2/TRAILR4. TRAIL can also bind to osteoprotegerin (OPG), a soluble decoy receptor, at low affinity.

Targeting the TRAIL receptors has been considered a useful approach in developing cancer therapies, since if an antibody-based molecule can bind to and activate the TRAIL-receptor, i.e. a TRAIL-receptor agonist molecule, then it can induce apoptosis in cancer cells. As shown in many preclinical studies, TRAIL-signalling efficiently induces apoptosis in numerous tumor cell lines but not in the majority of normal cells. However, normal tissues especially hepatocytes in the liver are also reported to be susceptible to this mechanism of apoptosis induction. Hence, if a molecule is used which too efficiently activates the pathway, severe side effects can be induced due to apoptosis induction in non-cancerous cells. On the other hand, weakly-activating molecules have been shown to have poor anticancer activity, although they are well tolerated.

One approach is to combine targeting of the TRAIL receptor with a cancer cell-specific marker, i.e. a protein that is not or little expressed by non-cancerous cells.

A number of different anchor targets have been proposed as being suitable combination partners for TRAIL receptor binding molecules.

FAP (Fibroblast activation protein) has also been proposed as an anchor target. However, FAP is only expressed on activated fibroblast cells which are located within the tumor stroma. FAP is not expressed in epithelial cancer cells. Hence a FAP bispecific molecule will only function to promote apoptosis in those cancer cells which are in close physical contact with an activated fibroblast (Brunker et al., *Molecular Cancer Therapeutics* (2016), 15(5):946-957). Tumor cells that are not in direct contact with an activated fibroblast will not be affected by this treatment and will continue to proliferate. Hence there are clear disadvantages with using FAP as an anchor target to mediate TRAIL receptor-induced apoptosis in cancer cells. In addition, since activated fibroblast cells are also found in sites of tissue remodeling including liver fibrosis, lung fibrosis, artherio-sclerosis, and arthritis, a bispecific molecule targeting FAP and TRAIL receptor could potentially anchor onto the surface of activated fibroblasts and induce apoptosis on neighbouring normal TRAIL-sensitive cells in the liver or other organs.

Similarly, MCSP (melanoma-associated chondroitin sulfate proteoglycan) and ROBO4 (roundabout homolog 4) have been proposed as anchor targets (He Yuan et al., *The Journal of Investigative Dermatology* (2016), 136(2):541-544; WO2011039126A1). Apart from its expression on the cell surface of melanomas, MCSP is mainly expressed on neovasculature. ROBO4 is specifically expressed in endothelial cells. Both are described at sites of angiogenesis in different tumors types. Hence, as with FAP, and with the only exception of MSCP-expressing melanomas, to be effective a bispecific molecule targeting MCSP or ROBO4 and a TRAIL receptor will only function to promote apoptosis in cancer cells if they are in close physical contact with endothelial cells. This will not always be possible as a tumor rapidly outgrows its blood supply as it grows. Therefore, again, there are disadvantages to using these molecules as anchor targets.

Furthermore, a bispecific antibody targeting TRAILR2 and LTβR (lymphotoxin-beta Receptor) has been reported to be active in inhibiting tumor growth in murine tumor xenograft models at levels comparable to or greater than the combination of the respective parental antibodies (Michaelson et al., *mAbs* (2009), 1(2):128-141). LTβR signalling in mice has been shown to be critical for liver regeneration, where LTβR is expressed on mature hepatocytes (Anders R. A. et al. *J Immunol* (2005), 175(2):1295-1300). Similar to FAP, LTβR signalling is broadly activated during chronic liver inflammation in patients with viral and non-viral hepatitis, cholangitis and HCC. In particular, its expression in hepatocytes has been described (Haybaeck J. et al. *Cancer Cell* (2009), 16(4): 295-308). Targeting LTβR and TRAIL receptor could potentially anchor onto the surface of LTβR-expressing hepatocytes which are sensitive to TRAILR2 activation, and thus may potentially cause liver toxicity.

Finally, TENASCIN C has also been suggested to be a useful anchor target. TENASCIN C is a secreted protein and hence is not anchored to the cell membrane. This represents another example of an indirect mechanism to induce apoptosis in cancer cells. As with MCSP or ROBO4 anchoring strategies, the TENASCIN C moiety must be in proper orientation to the TRAILR2 molecules on the cancer cell membrane for apoptosis to be effected. In addition, TENASCIN C expression is also upregulated in chronic liver disease and treatment with bispecific molecule comprising a TRAIL agonist is expected to worsen the condition.

Thus, although there have been advances in the treatment of certain cancers in recent years and despite the fact, that numerous different approaches are currently pursued, there is still a need to provide novel, therapeutically suitable compounds for the treatment of cancer and in particular to develop therapeutically efficacious but safe antibody-based biological molecules which can function as TRAIL-receptor agonist molecules.

It is thus an objective of the present invention to generate TRAIL-receptor agonist molecules having an improved therapeutic profile and providing certain advantages compared to the agents, compositions and/or methods currently used and/or known in the art. These advantages include in vivo efficacy, improved therapeutic and pharmacological properties, less side effects, and/or other advantageous properties such as high stability, particularly in a low pH environment, and improved ease of production or reduced costs of goods, especially as compared to molecules already known in the art.

BRIEF SUMMARY OF THE INVENTION

The objective is solved by the subject matter of the present invention. The present invention is based on the concept of combining an antigen binding site that binds specifically to TNF-related apoptosis-inducing ligand receptor 2 (TRAILR2) with an antigen binding site that binds specifically to cadherin-3 (CDH3) within a single binding molecule. As discussed in more detail below, one advantage of the molecule of the invention is that apoptosis is only promoted in cells that present both, TRAILR2 and CDH3 on their surface.

The inventors of the present invention have further discovered that use of an antigen binding site that binds specifically to the extracellular domain 1 (EC1) of CDH3 significantly improves efficacy of the binding molecule.

According to a first aspect of the invention, the invention provides a binding molecule comprising:

(a) at least one antigen binding site that binds specifically to TNF-related apoptosis-inducing ligand receptor 2 (TRAILR2), and (b) at least one antigen binding site that binds specifically to cadherin-3 (CDH3), wherein said at least one antigen binding site that binds specifically to CDH3 is selected from the group consisting of:

i. an antigen binding site comprising heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3);

ii. an antigen binding site comprising heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3);

iii. an antigen binding site comprising heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3); and iv. an antigen binding site comprising heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3).

In a specific aspect, the invention provides a binding molecule having at least one antigen binding site (a first antigen binding site) that binds specifically to TNF-related apoptosis inducing ligand receptor 2 (TRAILR2) and at least one antigen binding site (a second antigen binding site) that binds specifically to the extracellular domain 1 (EC1 domain) of cadherin-3 (CDH3).

Specifically, the binding molecule provided herein is a bispecific binding molecule.

In one aspect, the binding molecule provided herein thus recognizes an antigen comprising SEQ ID NO:98, or an amino acid sequence that is at least 80%, at least 90%, at least 95%, at least 98%, or at least 99% identical to SEQ ID NO:98.

In a specific aspect, the binding molecule provided herein specifically binds to an antigen comprising SEQ ID NO:99, or an amino acid sequence that is at least 80%, at least 90%, at least 95%, at least 98%, or at least 99% identical to SEQ ID NO:99.

In a preferred embodiment of the binding molecule of the invention, the antigen binding site that binds specifically to CDH3 (the second antigen binding site) is selected from the group consisting of:

- i. a heavy chain variable domain (VH) comprising the amino acid sequence of SEQ ID NO:2 and a light chain variable domain (VL) comprising the amino acid sequence of SEQ ID NO:6;
- ii. a VH comprising the amino acid sequence of SEQ ID NO:12 and a VL comprising the amino acid sequence of SEQ ID NO:16;
- iii. a VH comprising the amino acid sequence of SEQ ID NO:22 and a VL comprising the amino acid sequence of SEQ ID NO:26; and
- iv. a VH comprising the amino acid sequence of SEQ ID NO:32 and a VL comprising the amino acid sequence of SEQ ID NO:36.

In a preferred embodiment, the binding molecule provided herein comprises:

- i. a heavy chain comprising the amino acid sequence of SEQ ID NO:80 and a light chain comprising the amino acid sequence of SEQ ID NO:81;
- ii. a heavy chain comprising the amino acid sequence of SEQ ID NO:82 and a light chain comprising the amino acid sequence of SEQ ID NO:83;
- iii. a heavy chain comprising the amino acid sequence of SEQ ID NO:84 and a light chain comprising the amino acid sequence of SEQ ID NO:85; or light chain comprising the amino acid sequence of SEQ ID NO:87.

In a specific embodiment, the binding molecule provided herein comprises:

- i. a heavy chain comprising the amino acid sequence of SEQ ID NO:80, or an amino acid sequence that is at least 80%, at least 90%, at least 95%, at least 98%, or at least 99% identical to SEQ ID NO:80, and a light chain comprising the amino acid sequence of SEQ ID NO:81, or an amino acid sequence that is at least 80%, at least 90%, at least 95%, at least 98%, or at least 99% identical to SEQ ID NO:81;
- ii. a heavy chain comprising the amino acid sequence of SEQ ID NO:82, or an amino acid sequence that is at least 80%, at least 90%, at least 95%, at least 98%, or at least 99% identical to SEQ ID NO:82, and a light chain comprising the amino acid sequence of SEQ ID NO:83, or an amino acid sequence that is at least 80%, at least 90%, at least 95%, at least 98%, or at least 99% identical to SEQ ID NO:83;
- iii. a heavy chain comprising the amino acid sequence of SEQ ID NO:84, or an amino acid sequence that is at least 80%, at least 90%, at least 95%, at least 98%, or at least 99% identical to SEQ ID NO:84, and a light chain comprising the amino acid sequence of SEQ ID NO:85, or an amino acid sequence that is at least 80%, at least 90%, at least 95%, at least 98%, or at least 99% identical to SEQ ID NO:85; or
- iv. a heavy chain comprising the amino acid sequence of SEQ ID NO:86, or an amino acid sequence that is at least 80%, at least 90%, at least 95%, at least 98%, or at least 99% identical to SEQ ID NO:86, and a light chain comprising the amino acid sequence of SEQ ID NO:87, or an amino acid sequence that is at least 80%, at least 90%, at least 95%, at least 98%, or at least 99% identical to SEQ ID NO:87.

In a specific embodiment, the binding molecule provided herein comprises an antigen binding site that binds specifically to CDH3 comprising a heavy chain variable region comprising an amino acid sequence that is at least 80%, at least 90%, at least 95%, at least 98%, or at least 99% identical to SEQ ID NO:2 and contains the CDR1 of SEQ ID NO:3, the CDR2 of SEQ ID NO:4, and the CDR3 of SEQ ID NO:5, and comprises a light chain variable region comprising an amino acid sequence that is at least 80%, at least 90%, at least 95%, at least 98%, or at least 99% identical, respectively, to SEQ ID NO:6 and contains the light chain CDR1 of SEQ ID NO:7, the light chain CDR2 of SEQ ID NO:8, and the light chain CDR3 of SEQ ID NO:9.

In a specific embodiment, the binding molecule provided herein comprises an antigen binding site that binds specifically to CDH3 comprising a heavy chain variable region comprising an amino acid sequence that is at least 80%, at least 90%, at least 95%, at least 98%, or at least 99% identical to SEQ ID NO:12 and contains the CDR1 of SEQ ID NO:13, the CDR2 of SEQ ID NO:14, and the CDR3 of SEQ ID NO:15, and comprises a light chain variable region comprising an amino acid sequence that is at least 80%, at least 90%, at least 95%, at least 98%, or at least 99% identical, respectively, to SEQ ID NO:16 and contains the light chain CDR1 of SEQ ID NO:17, the light chain CDR2 of SEQ ID NO:18, and the light chain CDR3 of SEQ ID NO:19.

In a specific embodiment, the binding molecule provided herein comprises an antigen binding site that binds specifically to CDH3 comprising a heavy chain variable region comprising an amino acid sequence that is at least 80%, at least 90%, at least 95%, at least 98%, or at least 99% identical to SEQ ID NO:22 and contains the CDR1 of SEQ ID NO:23, the CDR2 of SEQ ID NO:24, and the CDR3 of SEQ ID NO:25, and comprises a light chain variable region comprising an amino acid sequence that is at least 80%, at least 90%, at least 95%, at least 98%, or at least 99% identical, respectively, to SEQ ID NO:26 and contains the light chain CDR1 of SEQ ID NO:27, the light chain CDR2 of SEQ ID NO:28, and the light chain CDR3 of SEQ ID NO:29.

In a specific embodiment, the binding molecule provided herein comprises an antigen binding site that binds specifically to CDH3 comprising a heavy chain variable region comprising an amino acid sequence that is at least 80%, at least 90%, at least 95%, at least 98%, or at least 99% identical to SEQ ID NO:32 and contains the CDR1 of SEQ ID NO:33, the CDR2 of SEQ ID NO:34, and the CDR3 of SEQ ID NO:35, and comprises a light chain variable region comprising an amino acid sequence that is at least 80%, at least 90%, at least 95%, at least 98%, or at least 99% identical, respectively, to SEQ ID NO:36 and contains the light chain CDR1 of SEQ ID NO:37, the light chain CDR2 of SEQ ID NO:38, and the light chain CDR3 of SEQ ID NO:39.

In a specific embodiment, the binding molecule provided herein comprises an antigen binding site that binds specifically to CDH3 comprising a heavy chain variable region comprising an amino acid sequence that is at least 80%, at least 90%, at least 95%, at least 98%, or at least 99% identical to SEQ ID NO:42 and contains the CDR1 of SEQ ID NO:43, the CDR2 of SEQ ID NO:44, and the CDR3 of SEQ ID NO:45, and comprises a light chain variable region comprising an amino acid sequence that is at least 80%, at least 90%, at least 95%, at least 98%, or at least 99% identical, respectively, to SEQ ID NO:46 and contains the light chain CDR1 of SEQ ID NO:47, the light chain CDR2 of SEQ ID NO:48, and the light chain CDR3 of SEQ ID NO:49.

In a specific embodiment, the binding molecule provided herein comprises an antigen binding site that binds specifically to CDH3 comprising a heavy chain variable region comprising an amino acid sequence that is at least 80%, at least 90%, at least 95%, at least 98%, or at least 99% identical to SEQ ID NO:52 and contains the CDR1 of SEQ ID NO:53, the CDR2 of SEQ ID NO:54, and the CDR3 of SEQ ID NO:55, and comprises a light chain variable region comprising an amino acid sequence that is at least 80%, at least 90%, at least 95%, at least 98%, or at least 99% identical, respectively, to SEQ ID NO:56 and contains the light chain CDR1 of SEQ ID NO:57, the light chain CDR2 of SEQ ID NO:58, and the light chain CDR3 of SEQ ID NO:59.

In a specific embodiment, the binding molecule provided herein comprises an antigen binding site that binds specifically to CDH3 comprising a heavy chain variable region comprising an amino acid sequence that is at least 80%, at least 90%, at least 95%, at least 98%, or at least 99% identical to SEQ ID NO:62 and contains the CDR1 of SEQ ID NO:63, the CDR2 of SEQ ID NO:64, and the CDR3 of SEQ ID NO:65, and comprises a light chain variable region comprising an amino acid sequence that is at least 80%, at least 90%, at least 95%, at least 98%, or at least 99% identical, respectively, to SEQ ID NO:66 and contains the light chain CDR1 of SEQ ID NO:67, the light chain CDR2 of SEQ ID NO:68, and the light chain CDR3 of SEQ ID NO:69.

In a specific embodiment, the binding molecule provided herein comprises an antigen binding site that binds specifically to CDH3 comprising a heavy chain comprising an amino acid sequence that is at least 80%, at least 90%, at least 95%, at least 98%, or at least 99% identical to SEQ ID NO:80 and contains the CDR1 of SEQ ID NO:3, the CDR2 of SEQ ID NO:4, and the CDR3 of SEQ ID NO:5, and comprises a light chain comprising an amino acid sequence that is at least 80%, at least 90%, at least 95%, at least 98%, or at least 99% identical, respectively, to SEQ ID NO:81 and contains the light chain CDR1 of SEQ ID NO:7, the light chain CDR2 of SEQ ID NO:8, and the light chain CDR3 of SEQ ID NO:9.

In a specific embodiment, the binding molecule provided herein comprises an antigen binding site that binds specifically to CDH3 comprising a heavy chain comprising an amino acid sequence that is at least 80%, at least 90%, at least 95%, at least 98%, or at least 99% identical to SEQ ID NO:82 and contains the CDR1 of SEQ ID NO:13, the CDR2 of SEQ ID NO:14, and the CDR3 of SEQ ID NO:15, and comprises a light chain comprising an amino acid sequence that is at least 80%, at least 90%, at least 95%, at least 98%, or at least 99% identical, respectively, to SEQ ID NO:83 and contains the light chain CDR1 of SEQ ID NO:17, the light chain CDR2 of SEQ ID NO:18, and the light chain CDR3 of SEQ ID NO:19.

In a specific embodiment, the binding molecule provided herein comprises an antigen binding site that binds specifically to CDH3 comprising a heavy chain comprising an amino acid sequence that is at least 80%, at least 90%, at least 95%, at least 98%, or at least 99% identical to SEQ ID NO:84 and contains the CDR1 of SEQ ID NO:23, the CDR2 of SEQ ID NO:24, and the CDR3 of SEQ ID NO:25, and comprises a light chain comprising an amino acid sequence that is at least 80%, at least 90%, at least 95%, at least 98%, or at least 99% identical, respectively, to SEQ ID NO:85 and contains the light chain CDR1 of SEQ ID NO:27, the light chain CDR2 of SEQ ID NO:28, and the light chain CDR3 of SEQ ID NO:29.

In a specific embodiment, the binding molecule provided herein comprises an antigen binding site that binds specifically to CDH3 comprising a heavy chain comprising an amino acid sequence that is at least 80%, at least 90%, at least 95%, at least 98%, or at least 99% identical to SEQ ID NO:86 and contains the CDR1 of SEQ ID NO:33, the CDR2 of SEQ ID NO:34, and the CDR3 of SEQ ID NO:35, and comprises a light chain comprising an amino acid sequence that is at least 80%, at least 90%, at least 95%, at least 98%, or at least 99% identical, respectively, to SEQ ID NO:87 and contains the light chain CDR1 of SEQ ID NO:37, the light chain CDR2 of SEQ ID NO:38, and the light chain CDR3 of SEQ ID NO:39.

In a specific embodiment, the binding molecule provided herein comprises an antigen binding site that binds specifically to CDH3 comprising a heavy chain comprising an amino acid sequence that is at least 80%, at least 90%, at least 95%, at least 98%, or at least 99% identical to SEQ ID NO:88 and contains the CDR1 of SEQ ID NO:43, the CDR2 of SEQ ID NO:44, and the CDR3 of SEQ ID NO:45, and comprises a light chain comprising an amino acid sequence that is at least 80%, at least 90%, at least 95%, at least 98%, or at least 99% identical, respectively, to SEQ ID NO:89 and contains the light chain CDR1 of SEQ ID NO:47, the light chain CDR2 of SEQ ID NO:48, and the light chain CDR3 of SEQ ID NO:49.

In a specific embodiment, the binding molecule provided herein comprises an antigen binding site that binds specifically to CDH3 comprising a heavy chain comprising an amino acid sequence that is at least 80%, at least 90%, at least 95%, at least 98%, or at least 99% identical to SEQ ID NO:90 and contains the CDR1 of SEQ ID NO:53, the CDR2 of SEQ ID NO:54, and the CDR3 of SEQ ID NO:55, and comprises a light chain comprising an amino acid sequence that is at least 80%, at least 90%, at least 95%, at least 98%, or at least 99% identical, respectively, to SEQ ID NO:91 and contains the light chain CDR1 of SEQ ID NO:57, the light chain CDR2 of SEQ ID NO:58, and the light chain CDR3 of SEQ ID NO:59.

In a specific embodiment, the binding molecule provided herein comprises an antigen binding site that binds specifically to CDH3 comprising a heavy chain comprising an amino acid sequence that is at least 80%, at least 90%, at least 95%, at least 98%, or at least 99% identical to SEQ ID NO:92 and contains the CDR1 of SEQ ID NO:63, the CDR2 of SEQ ID NO:64, and the CDR3 of SEQ ID NO:65, and comprises a light chain comprising an amino acid sequence that is at least 80%, at least 90%, at least 95%, at least 98%, or at least 99% identical, respectively, to SEQ ID NO:93 and contains the light chain CDR1 of SEQ ID NO:67, the light chain CDR2 of SEQ ID NO:68, and the light chain CDR3 of SEQ ID NO:69.

In a preferred embodiment of the binding molecule of the invention, the at least one antigen binding site that binds specifically to TRAILR2 comprises heavy chain CDRs comprising the amino acid sequences of SEQ ID NO:73 (CDR1), SEQ ID NO:74 (CDR2) and SEQ ID NO:75 (CDR3) and light chain CDRs comprising the amino acid sequences of SEQ ID NO:77 (CDR1), SEQ ID NO:78 (CDR2) and SEQ ID NO:79 (CDR3).

In a preferred embodiment of the binding molecule of the invention, the at least one antigen binding site that binds specifically to TRAILR2 (the first antigen binding site) is an antigen binding site comprising a heavy chain variable domain comprising the amino acid sequence of SEQ ID NO:72 and a light chain variable domain comprising the amino acid sequence of SEQ ID NO:76.

In a specific embodiment, the binding molecule provided herein comprises an antigen binding site that binds specifically to TRAILR2 comprising a VH comprising an amino acid sequence that is at least 80%, at least 90%, at least 95%, at least 98%, or at least 99% identical to SEQ ID NO:72 and contains the CDR1 of SEQ ID NO:73, the CDR2 of SEQ ID NO:74, and the CDR3 of SEQ ID NO:75, and comprises a VL comprising an amino acid sequence that is at least 80%, at least 90%, at least 95%, at least 98%, or at least 99% identical, respectively, to SEQ ID NO:76 and contains the light chain CDR1 of SEQ ID NO:77, the light chain CDR2 of SEQ ID NO:78, and the light chain CDR3 of SEQ ID NO:79.

In some embodiments, the binding molecules provided herein, which are defined by their heavy chain amino acid sequence (e.g. a modified heavy chain with a TRAILR2-specific scFv fused to the C-terminus of an Ig heavy chain) as well as their light chain amino acid sequence, comprise two heavy chains and two light chains, thereby forming a symmetric tetravalent and bispecific structure.

In yet a further preferred embodiment, the binding molecule of the invention comprises a modified heavy chain, preferably wherein a TRAILR2-specific scFv is fused to the C-terminus of an Ig heavy chain. Preferably, said modified heavy chain comprises the amino acid sequence of SEQ ID NO:1, SEQ ID NO:11, SEQ ID NO:21, or SEQ ID NO:31.

Specifically, the binding molecule of the invention comprises an amino acid sequence that is at least 80%, at least 90%, at least 95%, at least 98%, or at least 99% identical to SEQ ID NO:1, SEQ ID NO:11, SEQ ID NO:21, or SEQ ID NO:31.

Specifically, the binding molecule of the invention comprises:

i. a modified heavy chain comprising the amino acid sequence of SEQ ID NO:1 and a light chain comprising the amino acid sequence of SEQ ID NO:81;
ii. a modified heavy chain comprising the amino acid sequence of SEQ ID NO:11 and a light chain comprising the amino acid sequence of SEQ ID NO:83;
iii. a modified heavy chain comprising the amino acid sequence of SEQ ID NO:21 and a light chain comprising the amino acid sequence of SEQ ID NO:85; or
iv. a modified heavy chain comprising the amino acid sequence of SEQ ID NO:31 and a light chain comprising the amino acid sequence of SEQ ID NO:87.

In a preferred embodiment of the binding molecule of the invention, the molecule is bispecific and tetravalent.

Specifically, the at least one antigen binding site that binds specifically to TRAILR2 is linked to the at least one antigen binding site that binds specifically to CDH3.

In a preferred embodiment of the binding molecule of the invention, the at least one antigen binding site that binds specifically to CDH3 is an immunoglobulin (Ig) molecule (having the conventional Y shaped structure of a full-length antibody with two light and two heavy chains) and the at least one antigen binding site that binds specifically to TRAILR2 comprises one or more scFv(s).

In a preferred embodiment of the binding molecule of the invention, the one or more scFv(s) have a VL-VH orientation from N- to C-terminus.

In a preferred embodiment of the binding molecule of the invention, the one or more scFv(s) is fused to the C-terminus of the heavy chain of the Ig molecule, thereby forming a modified Ig molecule. For example, one scFv is fused to the C-terminus of one of the heavy chains of the Ig molecule and one scFv is fused to the C-terminus of the other heavy chain of the Ig molecule. As such, an scFv specific for TRAILR2 is fused to each of the heavy chains of the Ig molecule, thereby forming a symmetric, bispecific and tetravalent structure.

In a preferred embodiment, the binding molecule of the invention comprises two antigen binding sites that bind specifically to TNF-related apoptosis-inducing ligand receptor 2 (TRAILR2) and two antigen binding sites that bind specifically to cadherin-3 (CDH3).

Thus, in a specific aspect, a bispecific and tetravalent binding molecule is provided herein, wherein the binding molecule is a modified immunoglobulin (Ig) molecule comprising two antigen binding sites that bind specifically to TNF-related apoptosis-inducing ligand receptor 2 (TRAILR2) and two antigen binding sites that bind specifically to cadherin-3 (CDH3); wherein the two antigen binding sites that bind specifically to CDH3 reside in the variable region (Fv) of the Ig molecule and the two antigen binding sites that bind specifically to TRAILR2 are scFvs; and wherein the scFvs are fused to the C-terminus of the heavy chains of the Ig molecule. Preferably, a first scFv is fused to a first heavy chain and a second scFv is fused the second heavy chain of the Ig molecule, respectively.

In a preferred embodiment of the binding molecule of the invention, the Ig molecule is IgG1KO. In another preferred embodiment of the binding molecule of the invention, the Ig molecule is IgG1 FcRnmut.

In a preferred embodiment of the binding molecule of the invention, the one or more scFv(s) is fused to the Ig molecule by a peptide linker, preferably a peptide linker having a length of about 4 to 20 amino acids (e.g., any one of 5, 6, 9, 12, 15 amino acids).

Further described herein are binding molecules, specifically bispecific binding molecules, having at least one antigen binding site (a first antigen binding site) that binds specifically to TNF-related apoptosis inducing ligand receptor 2 (TRAILR2), as described in detail above, and at least one antigen binding site (a second antigen binding site) that binds specifically to the extracellular domain 2 (EC2 domain) of cadherin-3 (CDH3).

Further provided herein is an antibody that binds specifically to CDH3, comprising:

i. heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3);
ii. heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3);
iii. heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3);
iv. heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3);
v. heavy chain CDRs comprising the amino acid sequences of SEQ ID NO:43 (CDR1), SEQ ID NO:44

(CDR2) and SEQ ID NO:45 (CDR3) and light chain CDRs comprising the amino acid sequences of SEQ ID NO:47 (CDR1), SEQ ID NO:48 (CDR2) and SEQ ID NO:49 (CDR3);

vi. heavy chain CDRs comprising the amino acid sequences of SEQ ID NO:53 (CDR1), SEQ ID NO:54 (CDR2) and SEQ ID NO:55 (CDR3) and light chain CDRs comprising the amino acid sequences of SEQ ID NO:57 (CDR1), SEQ ID NO:58 (CDR2) and SEQ ID NO:59 (CDR3); or vii. heavy chain CDRs comprising the amino acid sequences of SEQ ID NO:63 (CDR1), SEQ ID NO:64 (CDR2) and SEQ ID NO:65 (CDR3) and light chain CDRs comprising the amino acid sequences of SEQ ID NO:67 (CDR1), SEQ ID NO:68 (CDR2) and SEQ ID NO:69 (CDR3).

In a preferred embodiment, the antibody provided herein comprises:

i. a heavy chain variable domain (VH) comprising the amino acid sequence of SEQ ID NO:2 and a light chain variable domain (VL) comprising the amino acid sequence of SEQ ID NO:6;

ii. a VH comprising the amino acid sequence of SEQ ID NO:12 and a VL comprising the amino acid sequence of SEQ ID NO:16;

iii. a VH comprising the amino acid sequence of SEQ ID NO:22 and a VL comprising the amino acid sequence of SEQ ID NO:26;

iv. a VH comprising the amino acid sequence of SEQ ID NO:32 and a VL comprising the amino acid sequence of SEQ ID NO:36;

v. a VH comprising the amino acid sequence of SEQ ID NO:42 and a VL comprising the amino acid sequence of SEQ ID NO:46;

vi. a VH comprising the amino acid sequence of SEQ ID NO:52 and a VL comprising the amino acid sequence of SEQ ID NO:56; or vii. a VH comprising the amino acid sequence of SEQ ID NO:62 and a VL comprising the amino acid sequence of SEQ ID NO:66.

In yet a further preferred embodiment of the invention, the antibody that binds specifically to CDH3 comprises:

i. a heavy chain comprising the amino acid sequence of SEQ ID NO:80 and a light chain comprising the amino acid sequence of SEQ ID NO:81;

ii. a heavy chain comprising the amino acid sequence of SEQ ID NO:82 and a light chain comprising the amino acid sequence of SEQ ID NO:83;

iii. a heavy chain comprising the amino acid sequence of SEQ ID NO:84 and a light chain comprising the amino acid sequence of SEQ ID NO:85;

iv. a heavy chain comprising the amino acid sequence of SEQ ID NO:86 and a light chain comprising the amino acid sequence of SEQ ID NO:87;

v. a heavy chain comprising the amino acid sequence of SEQ ID NO:88 and a light chain comprising the amino acid sequence of SEQ ID NO:89;

vi. a heavy chain comprising the amino acid sequence of SEQ ID NO:90 and a light chain comprising the amino acid sequence of SEQ ID NO:91; or vii. a heavy chain comprising the amino acid sequence of SEQ ID NO:92 and a light chain comprising the amino acid sequence of SEQ ID NO:93.

Specifically, the antibody comprises:

i. a heavy chain comprising the amino acid sequence of SEQ ID NO:80, or an amino acid sequence that is at least 80%, at least 90%, at least 95%, at least 98%, or at least 99% identical to SEQ ID NO:80, and a light chain comprising the amino acid sequence of SEQ ID NO:81, or an amino acid sequence that is at least 80%, at least 90%, at least 95%, at least 98%, or at least 99% identical to SEQ ID NO:81;

ii. a heavy chain comprising the amino acid sequence of SEQ ID NO:82, or an amino acid sequence that is at least 80%, at least 90%, at least 95%, at least 98%, or at least 99% identical to SEQ ID NO:82, and a light chain comprising the amino acid sequence of SEQ ID NO:83, or an amino acid sequence that is at least 80%, at least 90%, at least 95%, at least 98%, or at least 99% identical to SEQ ID NO:83;

iii. a heavy chain comprising the amino acid sequence of SEQ ID NO:84, or an amino acid sequence that is at least 80%, at least 90%, at least 95%, at least 98%, or at least 99% identical to SEQ ID NO:84, and a light chain comprising the amino acid sequence of SEQ ID NO:85, or an amino acid sequence that is at least 80%, at least 90%, at least 95%, at least 98%, or at least 99% identical to SEQ ID NO:85;

iv. a heavy chain comprising the amino acid sequence of SEQ ID NO:86, or an amino acid sequence that is at least 80%, at least 90%, at least 95%, at least 98%, or at least 99% identical to SEQ ID NO:86, and a light chain comprising the amino acid sequence of SEQ ID NO:87, or an amino acid sequence that is at least 80%, at least 90%, at least 95%, at least 98%, or at least 99% identical to SEQ ID NO:87;

v. a heavy chain comprising the amino acid sequence of SEQ ID NO:88, or an amino acid sequence that is at least 80%, at least 90%, at least 95%, at least 98%, or at least 99% identical to SEQ ID NO:88, and a light chain comprising the amino acid sequence of SEQ ID NO:89, or an amino acid sequence that is at least 80%, at least 90%, at least 95%, at least 98%, or at least 99% identical to SEQ ID NO:89;

vi. a heavy chain comprising the amino acid sequence of SEQ ID NO:90, or an amino acid sequence that is at least 80%, at least 90%, at least 95%, at least 98%, or at least 99% identical to SEQ ID NO:90, and a light chain comprising the amino acid sequence of SEQ ID NO:91, or an amino acid sequence that is at least 80%, at least 90%, at least 95%, at least 98%, or at least 99% identical to SEQ ID NO:91; or vii. a heavy chain comprising the amino acid sequence of SEQ ID NO:92, or an amino acid sequence that is at least 80%, at least 90%, at least 95%, at least 98%, or at least 99% identical to SEQ ID NO:92, and a light chain comprising the amino acid sequence of SEQ ID NO:93, or an amino acid sequence that is at least 80%, at least 90%, at least 95%, at least 98%, or at least 99% identical to SEQ ID NO:93.

In a preferred embodiment, the antibody or antigen-binding fragment thereof provided herein is selected from the group consisting of chimeric, humanized, and human antibodies or antibody fragments, and scFVs, Fab fragments, monovalent antibody fragments and $F(ab')^2$ fragments.

A further aspect of the invention provides a nucleic acid molecule encoding a binding molecule of the invention or an expression vector containing such a nucleic acid molecule.

In a preferred embodiment, said vector is a plasmid or a viral vector.

A further aspect of the invention provides a host cell comprising a nucleic acid molecule of the invention in functional association with an expression control sequence.

Further provided herein is a host cell comprising an expression vector comprising a nucleic acid molecule encoding a binding molecule as described herein.

A further aspect of the invention provides a method of production of a binding molecule of the invention, comprising i. cultivating the host cell under conditions allowing expression of the molecule, and
ii. recovering the molecule, and optionally
iii. further purifying and/or modifying and/or formulating the molecule.

Further provided herein is the binding molecule of the invention, for use in medicine.

In a preferred embodiment, the binding molecule of the invention is provided for use in the treatment of cancer, preferably pancreatic cancer, lung cancer or head and neck cancer.

Further provided herein is a pharmaceutical composition comprising the binding molecule of the invention together with a pharmaceutically acceptable carrier and optionally one or more further active ingredients.

A further aspect of the invention provides a method of treatment of cancer comprising administering an effective amount of a binding molecule of the invention to a patient in need thereof.

In a preferred embodiment, the pharmaceutical composition provided herein is lyophilized, stabilized and/or formulated for administration by injection.

BRIEF SUMMARY OF THE DRAWINGS

FIG. 1: Amino acid sequences of CDH3.

DETAILED DESCRIPTION OF THE INVENTION

Figure 2:
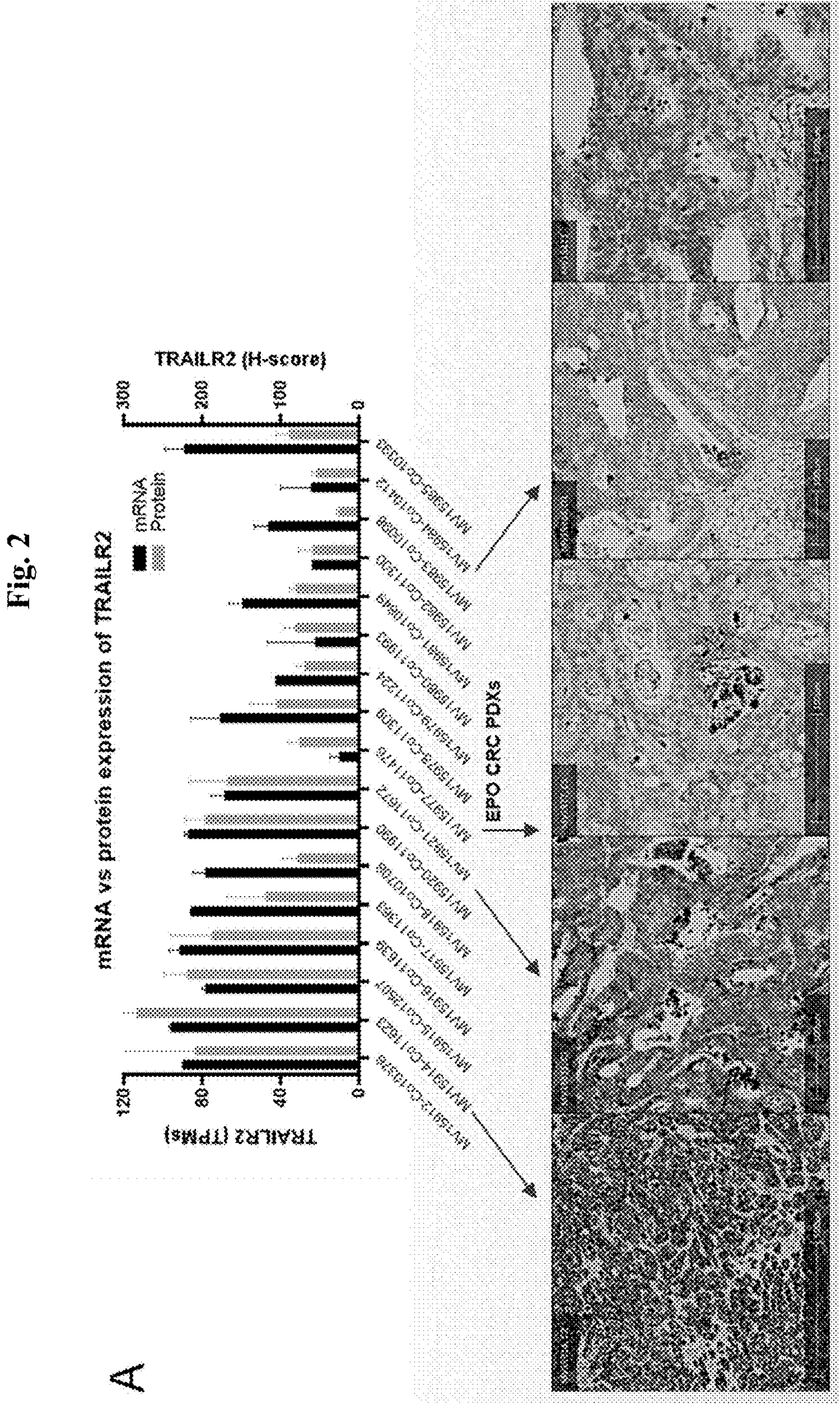
FIG. 2: Expression of CDH3 and TRAILR2. Protein expression and membrane localisation in correlation with mRNA expression for TRAILR2 and CDH3 is demonstrated in PDXs derived from colorectal cancer (A and B). In addition, membrane staining of CDH3 and TRAILR2 is shown in surgical tumor tissues from squamous cell carcinoma of head and neck and squamous cell carcinoma of the oesophagus (C).
Figure 2:
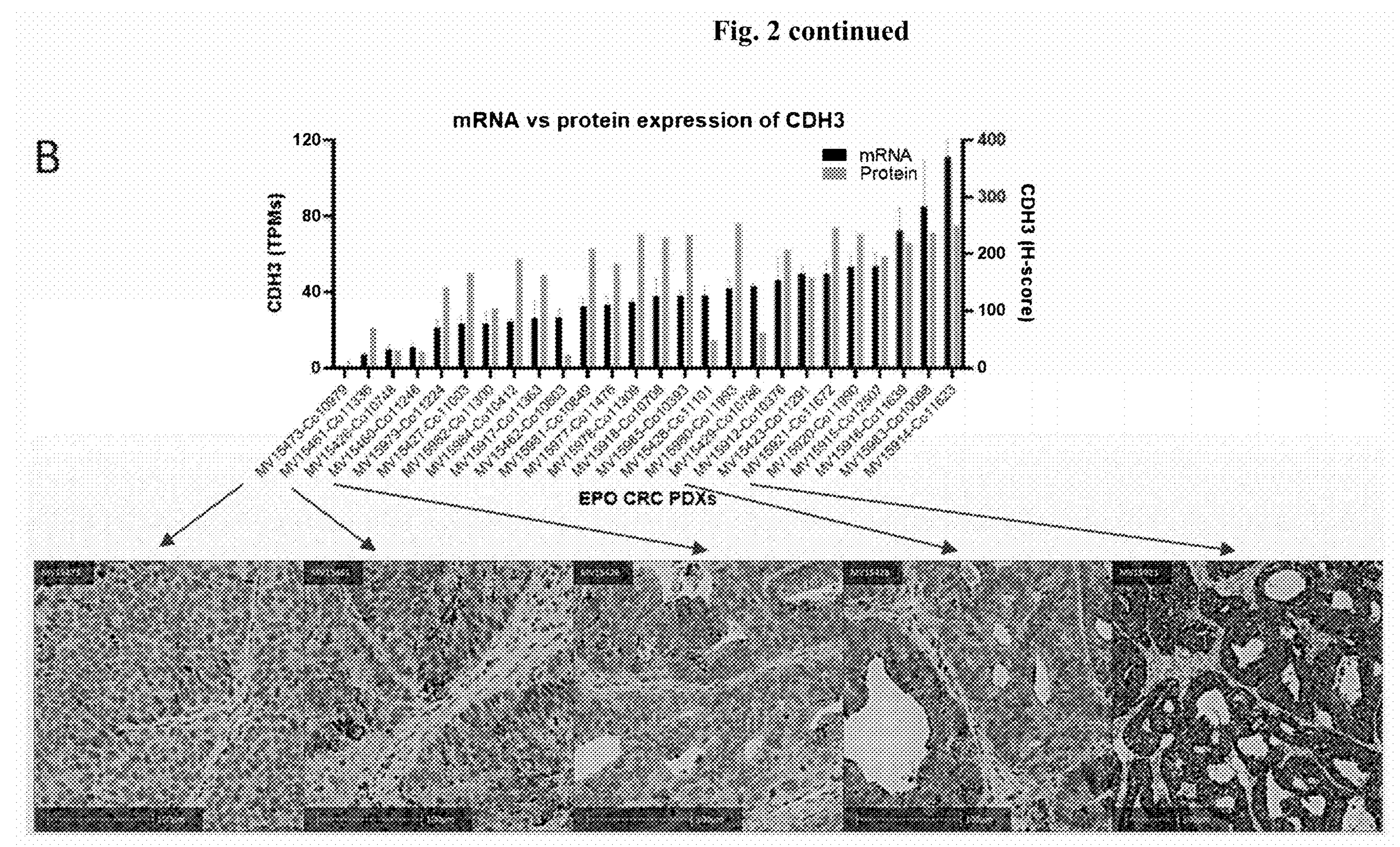
Figure 2:
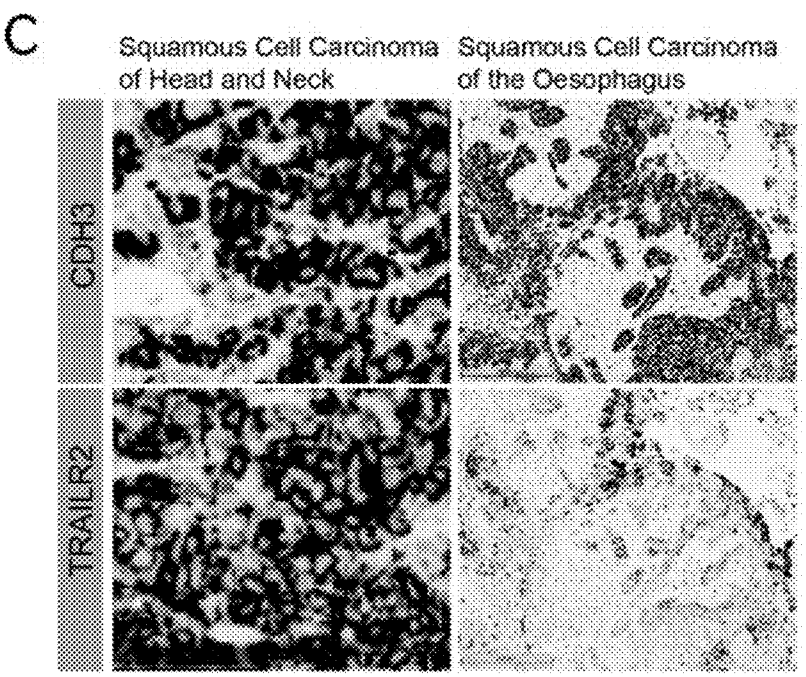

As described above, one approach to treating cancer has been to induce apoptosis in a cancer cell by using molecules which specifically bind to and activate the TNF-related apoptosis inducing ligand (TRAIL) receptor-mediated apoptotic pathway. As shown in many preclinical studies, TRAIL-signalling efficiently induces apoptosis in numerous tumor cell lines but not in the majority of normal cells. However, normal tissues especially hepatocytes in the liver are also reported to be susceptible to this mechanism of apoptosis induction.

TRAIL binds with high affinity to four distinct cell surface receptors. Two of them, TRAILR1 and TRAILR2, are able to trigger TRAIL-induced apoptosis via the interaction of its intracellular death domain with different adaptor proteins and pro-caspase 8. Clustering of TRAILR1 or TRAILR2 molecules via TRAIL ligand facilitates autocatalytic cleavage and activation of pro-caspase 8 which in turn leads to the induction of apoptosis. TRAILR3 and TRAILR4 are decoy receptors, and while their extracellular domains are able to bind TRAIL, the intracellular portions of the receptors do not contain a domain able to induce apoptosis upon TRAIL binding.

Overexpression of decoy TRAIL receptors can cause the cancer cells to be insensitive to the presence of the TRAIL ligand. The specific targeting of the non-decoy, death-inducing TRAIL receptors avoid this problem and it represents a more effective treatment of tumors.

The present invention focuses on developing TRAILR2 agonist molecules. TRAILR2 is widely expressed in a broad spectrum of cancers. Several TRAILR2 specific agonistic antibodies including Lexatumumab (HGS-ETR2) have been developed for the treatment of cancer. However, these agonistic antibodies lacked efficacy in the clinic. Without intent to be limited by theory, this is thought to be likely due to a lack of sufficient clustering of the TRAILR2 receptor, and hence the failure to effectively induce apoptosis in cancer cells.

In a different attempt to promote TRAILR2-mediated apoptosis in cancer cells, a tetrameric TRAILR2-binding nanobody, TAS266, has been developed. In preclinical experiments it demonstrated antitumor efficacy superior to conventional TRAILR2-targeting antibodies. However, it has been reported that hepatocytes in the liver can be sensitive to TRAILR2 mediated apoptosis and therefore a non-targeted increase of TRAILR2 clustering, as promoted by TAS266, has the risk of potential toxicity. Indeed, the Phase I clinical trial of TAS266 has been terminated.

Hence, if a molecule is used which too efficiently agonises the pathway, then severe side effects can be induced since apoptosis is induced in non-cancerous cells. On the other hand, if only weakly agonising molecules are used then these have been shown to have poor anticancer activity, although they are well tolerated.

One approach is to combine targeting of the TRAIL receptor with a cancer cell-specific marker, i.e. a protein that is not or little expressed by non-cancerous cells, also termed "anchor proteins" (see e.g. WO 2018/115231 A2 where CDH17 is used as anchor protein). However, such tumor-specific target proteins are rare and this scarcity remains a major drawback typically faced in the development of cancer-specific therapeutics. While attempts to target more broadly expressed lineage antigens have been made, the value of these therapies has been limited by toxicities caused by the expression of these antigens in certain normal tissues, such as for example the expression of Epcam in the gastro-intestinal tract (Kebenko et al., Oncoimmunology 2018, Vol. 7, No. 8). While various approaches to reduce the toxicities related to off-site antigen expression are currently pursued, toxicities still remain dose-limiting for many compounds.

The inventors have identified anchor proteins which are not present in substantial quantities in the serum and were localized in cancer cells which co-expressed the TRAILR2. Importantly, the selected anchor proteins are not expressed in liver, which is expected to be advantageous due to the potential liver toxicity described above.

The present inventors identified cadherin-3 as a suitable anchor target that can be used in combination with a TRAIL receptor binding molecule.

Cadherin-3 (CDH3) is a member of the cadherin superfamily, genes encoding calcium-dependent, membrane-associated glycoproteins. The encoded protein is cadherin-like, consisting of an extracellular region, containing 5 cadherin domains, a transmembrane region, and an intracellular domain.

The inventors analysed the expression of CDH3 in tumor tissues and discovered that TRAILR2 and CDH3 are co-expressed in a variety of tumors (i.e., pancreatic cancer (PAC), head and neck cancer, lung cancer, colorectal cancer, oesophageal cancer, triple negative breast cancer, ovarian cancer, skin cutaneous melanoma, and in bladder urothelial and cervical cancer), with little or no co-expression in non-cancerous cells. Notably, CDH3 was not detectable in normal liver tissue or hepatocytes with reported sensitivity to TRAILR2 activation.

Thus, herein provided are binding molecules including at least one antigen binding site that binds specifically to TRAILR2 and at least one antigen binding site that binds specifically to CDH3.

In the accompanying experimental data, it can be seen that such molecules are able to induce apoptosis in vitro and in vivo in cells where both CDH3 and TRAILR2 are expressed. Surprisingly, bispecific binding molecules binding to TRAILR2 and the EC1 domain of CDH3 induce apoptosis significantly more efficiently than such bispecific binding molecules targeting specifically the EC2 domain of CDH3, as is impressively demonstrated by the in vivo data shown in Example 6.

Importantly, as is also shown in the examples, the same molecules induce essentially no apoptosis in cells expressing TRAILR2 but not CDH3. Hence the binding molecules of the present invention are therapeutically effective for cancers in which the cancer cells express both CDH3 and TRAILR2. In one aspect, the binding molecules of the present invention do not affect CDH3 negative liver cells, thereby reducing the risk of liver toxicity.

Furthermore, the binding molecules of the present invention are highly stable at low pH conditions, allowing efficient production at large quantities and thus making them excellent candidates for therapeutic proteins.

Notably, the binding molecules of the present invention show essentially no internalization activity in a representable assay. As shown in Example 7, no internalization was measurable for an exemplary CDH3/TRAILR2 EC1-specific binding molecule. Little or very slow internalization is advantageous for supporting a durable and efficacious activation of TRAILR2 at the cell surface for the bispecific binding molecules of the invention.

Hence the CDH3/TRAILR2 binding molecules of the invention have clear advantages over known molecules in the art and offers utility to treat cancer, including pancreatic cancer, head and neck cancers and lung cancers. Some of these advantages include improved in vivo efficacy, less side effects, high stability and improved ease of production; especially as compared to molecules already known in the art.

The first aspect of the invention provides a binding molecule having at least one antigen binding site (a first antigen binding site) that binds specifically to TNF-related apoptosis inducing ligand receptor 2 (TRAILR2) and at least one antigen binding site (a second antigen binding site) that binds specifically to cadherin-3 (CDH3), preferably to the EC1 domain of CDH3.

Until the present invention it had not been disclosed or even remotely contemplated to prepare binding molecules which can specifically bind to TRAILR2 and CDH3, specifically, the EC1 domain of CDH3. Nonetheless individually each protein and their associated genes are known in the art and are well represented in biological databases.

For the avoidance of doubt, by "TNF-related apoptosis-inducing ligand receptor 2 (TRAILR2)" we mean the human protein provided in UniProt O14763 www.uniprot.org/uniprot/O14763, and the nucleic acid sequence encoding that protein.

For the avoidance of doubt, by "cadherin-3 (CDH3)" we mean the human protein provided in UniProt P22223 www.uniprot.org/uniprot/P22223, and the nucleic acid sequence encoding that protein.

The present invention relates to binding molecules that have binding specificities for at least two different targets. In relation to the present invention, the binding molecules are derived from antibodies. Techniques for making binding molecules include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Binding molecules of the invention may also be made by engineering electrostatic steering effects for making antibody Fc-heterodimeric molecules (WO2009/089004A1); cross-linking two or more antibodies or fragments (see, e.g., U.S. Pat. No. 4,676,980, and Brennan et al., *Science,* 229: 81 (1985)); using leucine zippers to produce bispecific antibodies (see, e.g., Kostelny et al., *Immunol.,* 148(5): 1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *Immunol.,* 152:5368 (1994)); and preparing trispecific antibodies as described, e.g., in Tutt et al. *Immunol.* 147: 60 (1991).

Terms not specifically defined herein should be given the meanings that would be given to them by one of skill in the art in light of the disclosure and the context. As used in the specification, however, unless specified to the contrary, the following terms have the meaning indicated and the following conventions are adhered to.

Used Terms and Definitions

A molecule (such as the binding molecule of the invention, or a fragment thereof) that can "bind", "bind to", "specifically bind", or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein. As used herein, the term "bispecific" when referring to a binding molecule, relates to a molecule (such as the binding molecule of the invention) that can specifically bind to or has specificity for at least two different antigens or proteins (or for at least part, fragment or epitope thereof).

The term "antigen binding site", as used herein, relates to a domain of a binding molecule that confers binding to a specific antigen. Antigen binding sites are originally derived from antibodies, although advances in this field have led to additional possibilities of designing and/or obtaining antigen binding sites without the need for generating a naturally occurring antibody against the target of interest. Irrespective of its origin, an "antigen binding site" in accordance with the present invention comprises at least the minimal structural elements, i.e. the necessary and sufficient structural elements, that allow for binding to its specific target antigen. Thus, an "antigen binding site" in accordance with the present invention comprises at least three heavy chain CDR sequences (in the case of single domain antibodies), more preferably at least three light chain and three heavy chain CDR sequences. As discussed below, these CDRs typically reside in the so-called variable domain, or variable region (Fv) of an antibody. It will be appreciated that whereas an antigen binding site comprises at least the minimal structural elements, it typically encompasses additional elements (such as e.g. the framework regions). Thus, as used in accordance with the present invention, an antigen binding site can also be defined via the sequences of the respective combination of heavy chain variable domain and light chain variable domain. It is particularly preferred in accordance with the present invention that an "antigen binding site" is comprised in a polypeptide and/or that each of said CDRs or said variable domains is/are (a) polypeptide(s) or peptide(s).

"Antibodies" or "immunoglobulin molecules" (also known as immunoglobulins, abbreviated Ig) are gamma globulin proteins that can be found in blood or other bodily fluids of vertebrates and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies can bind, by non-covalent interaction, to other molecules or structures known as antigens. This binding is specific in the sense that an antibody will only bind to a specific structure with high affinity. The unique part of the antigen recognized by an antibody is called an epitope, or antigenic determinant. The part of the antibody binding to the epitope is sometimes called paratope and resides in the so-called variable domain, or variable region (Fv) of the antibody. The variable domain comprises three so-called complementary-determining region (CDR's) spaced apart by framework regions (FR's).

Within the context of this invention, reference to CDR's is based on the definition of with Kabat (E. A. Kabat, T. T. Wu, H. Bilofsky, M. Reid-Miller and H. Perry, Sequence of Proteins of Immunological Interest, National Institutes of Health, Bethesda (1983)). An alternative definition of CDRs is based on (i) CCG (Chemical Computing Group as illustrated in Almagro et al., Proteins 2011; 79:3050-3066 and Maier et al, Proteins 2014; 82:1599-1610), (ii) Chothia (Chothia and Lesk, 1987, J. Mol. Biol. 196: 901-917), (iii) IMGT (Lefranc M P, Dev Comp Immunol. 2003 January; 27(1):55-77) and (iv) North (North B, J Mol Biol. (2011) 406:228-56).

The expressions "variable domains" or "variable region" or Fv as used herein denotes each of the pair of light and heavy chains which is involved directly in binding the antibody to the antigen. The variable domain of a light chain is abbreviated as "VL" and the variable domain of a heavy chain is abbreviated as "VH". The variable light and heavy chain domains have the same general structure and each domain comprises four framework (FR) regions whose sequences are widely conserved, connected by three HVRs (or CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site. The antibody's heavy and light chain CDR regions play a particularly important role in the binding specificity/affinity of the antibodies according to the invention and therefore provide a further object of the invention.

An immunoglobulin domain essentially consists of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "constant domains" or "constant region" as used within the current application denotes the sum of the domains of an antibody other than the variable region. Such constant domains and regions are well known in the state of the art and e.g. described by Kabat et al. ("Sequence of proteins of immunological interest", US Public Health Services, NIH Bethesda, MD, Publication No. 91).

The "Fc part" of an antibody is not involved directly in binding of an antibody to an antigen, but exhibit various effector functions. An "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM. According to the heavy chain constant regions the different classes of immunoglobulins are called α, δ, ε, γ, and μ respectively. Several of these may be further divided into subclasses (isotypes), e.g. IgGI, IgG2, IgG3, and IgG4, IgAI, and IgA2. The Fc part of an antibody is directly involved in ADCC (antibody dependent cell-mediated cytotoxicity) and CDC (complement-dependent cytotoxicity) based on complement activation, Clq binding and Fc receptor binding. Complement activation (CDC) is initiated by binding of complement factor Clq to the Fc part of most IgG antibody subclasses. While the influence of an antibody on the complement system is dependent on certain conditions, binding to Clq is caused by defined binding sites in the Fc part. Such binding sites are known in the state of the art and described e.g. by Boakle et al., Nature 282 (1975) 742-743, Lukas et al., J. Immunol. 127 (1981) 2555-2560, Brunhouse and Cebra, Mol. Immunol. 16 (1979) 907-917, Burton et al., Nature 288 (1980) 338-344, Thommesen et al., Mol. Immunol. 37 (2000) 995-1004, Idusogie et al., J. Immunol. 164 (2000) 4178-4184, Hezareh et al., J. Virology 75 (2001) 12161-12168, Morgan et al., Immunology 86 (1995) 319-324, EP 0307434. Such binding sites are e.g. L234, L235, D270, N297, E318, K320, K322, P331 and P329 (numbering according to EU index of Kabat, see below). Most crucial among these residues in mediating Clq and Fcgamma receptor binding in IgG1 are L234 and L235 (Hezareh et al., J. Virology 75 (2001) 12161-12168). Antibodies of subclass IgGI and IgG3 usually show complement activation and Clq and C3 binding, whereas IgG2 and IgG4 do not activate the complement system and do not bind Clq and C3.

The art has further developed antibodies and made them versatile tools in medicine and technology. Thus, in the context of the present invention the terms "binding molecule" "antibody molecule" or "antibody" do not only include antibodies as they may be found in nature, comprising e.g. two light chains and two or heavy chains, or just two heavy chains as in camelid species, but furthermore encompasses all molecules comprising at least one paratope with binding specificity to an antigen and structural similarity to a variable domain of an immunoglobulin.

The terms "antibody" and "antibody molecule" are used interchangeably herein.

Thus, an antibody may comprise a monoclonal antibody, a human antibody, a humanized antibody, a chimeric antibody, a fragment of an antibody, in particular a Fv, Fab, Fab', or F(ab')2 fragment, a single chain antibody, in particular a single chain variable fragment (scFv), a Small Modular Immunopharmaceutical (SMIP), a domain antibody, a nanobody, and/or a diabody. The antibody may have an effector function, such as ADCC or CDC, that is usually mediated by the Fc part (antibody constant region) of the antibody, or it may have no effector function, e.g. by lacking a Fc part or having a blocked, masked Fc part, in essence a Fc part that is not or insufficiently recognized by immune cells or immune system components, like the complement system. Monoclonal antibodies (mAb) are monospecific antibodies that are identical in amino acid sequence. They may be produced by hybridoma technology from a hybrid cell line (called hybridoma) representing a clone of a fusion of a specific antibody producing B cell with a myeloma (B cell cancer) cell (Kohler G, Milstein C. Continuous cultures of fused cells secreting antibody of predefined specificity. Nature 1975; 256:495-7). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells." J Immunol Methods 204 (1): 77-87; see also below). A "recombinant antibody" or "recombinant binding molecule" is an antibody or binding molecule which has been produced by a recombinantly engineered host cell. It is optionally isolated or purified.

Polyclonal antibodies represent a collection of antibody molecules with different amino acid sequences and may be obtained from the blood of vertebrates after immunization with the antigen by processes well-known in the art.

Monoclonal antibodies (mAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7.). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells.". J Immunol Methods 204 (1): 77-87; see also below).

For application in man, it is often desirable to reduce immunogenicity of antibodies originally derived from other species, like mouse. This can be done by construction of chimeric antibodies, or by a process called "humanization". In this context, a "chimeric antibody" is understood to be antibody comprising a sequence part (e.g. a variable domain) derived from one species (e.g. mouse) fused to a sequence part (e.g. the constant domains) derived from a different species (e.g. human). A "humanized antibody" is an antibody comprising a variable domain originally derived from a non-human species, wherein certain amino acids have been mutated to make the overall sequence of that variable domain more closely resemble to a sequence of a human variable domain. Methods of chimerisation and humanization of antibodies are well-known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy". Nature: 332:323.). The term "human antibodies", as used herein, relates to antibodies that were created based on sequences derived from the human genome, for example by phage display or use of transgenic animals (see e.g. WO 90/05144). The term "antibody", as used herein, explicitly includes such humanized antibodies, chimeric antibodies, as well as human antibodies.

A "humanized" antibody refers to an antibody comprising amino acid residues from nonhuman hypervariable regions (HVRs) and amino acid residues from human FRs. In certain embodiments, a humanized antibody will comprise substantially all of at least one, and typically two, variable domains, in which all or substantially all of the HVRs (e.g. complementary determining regions (CDRs)) correspond to those of a non-human antibody, and all or substantially the entire framework regions (FRs) correspond to those of a human antibody. A humanized antibody optionally may comprise at least a portion of an antibody constant region derived from a human antibody. A "humanized form" of an antibody, e.g. a non-human antibody, refers to an antibody that has undergone humanization.

Furthermore, technologies have been developed for creating antibodies based on sequences derived from the human genome, for example by phage display or use of transgenic animals (WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93.; Bruggemann M, Taussig M J. "Production of human antibody repertoires in transgenic mice". Curr Opin Biotechnol. 1997 August; 8(4):455-8.). Such antibodies are "human antibodies" in the context of the present invention.

The term "antibody", in particular the antibody molecules described herein, can also include fragments of immunoglobulins which retain antigen binding properties, like Fab, Fab', or F(ab')2 fragments. Such fragments may be obtained by fragmentation of immunoglobulins e.g. by proteolytic digestion, or by recombinant expression of such fragments. For example, immunoglobulin digestion can be accomplished by means of routine techniques, e.g. using papain or pepsin (WO 94/29348). Papain digestion of antibodies typically produces two identical antigen binding fragments, so-called Fab fragments, each with a single antigen binding site, and a residual Fc fragment. Pepsin treatment yields an F(ab')2. In Fab molecules, the variable domains are each fused to an immunoglobulin constant domain, preferably of human origin. Thus, the heavy chain variable domain may be fused to a CH1 domain (a so-called Fd fragment), and the light chain variable domain may be fused to a CL domain. Fab molecules may be produced by recombinant expression of respective nucleic acids in host cells, see below.

A number of technologies have been developed for placing variable domains of immunoglobulins, or molecules derived from such variable domains, in a different molecular context. Those should be also considered as "antibodies" in accordance with the present invention. In general, these antibody molecules are smaller in size compared to immunoglobulins, and may comprise a single amino acid chain or several amino acid chains. For example, a single-chain variable fragment (scFv) is a fusion of the variable regions of the heavy and light chains of immunoglobulins, linked together with a short linker, usually serine (S) or glycine (G) (WO 88/01649; WO 91/17271; Huston et al; International Reviews of Immunology, Volume 10, 1993, 195-217). "Single domain antibodies" or "nanobodies" harbour an antigen-binding site in a single Ig-like domain (WO 94/04678; WO 03/050531, Ward et al., Nature. 1989 Oct. 12; 341(6242):544-6; Revets et al., Expert Opin Biol Ther. 5(1):111-24, 2005). One or more single domain antibodies with binding specificity for the same or a different antigen may be linked together. Diabodies are bivalent antibody molecules consisting of two amino acid chains comprising two variable domains (WO 94/13804, Holliger et al., Proc Natl Acad Sci USA. 1993 Jul. 15; 90(14):6444-8). Other examples of antibody-like molecules are immunoglobulin super family antibodies (IgSF; Srinivasan and Roeske, Current Protein Pept. Sci. 2005, 6(2): 185-96). A different concept leads to the so-called Small Modular Immunopharmaceutical (SM IP) which comprises a Fv domain linked to single-chain hinge and effector domains devoid of the constant domain CH1 (WO 02/056910).

An antibody molecule may be fused (as a fusion protein) or otherwise linked (by covalent or non-covalent bonds) to other molecular entities, such as cytotoxic drugs, or entities having a desired impact on the properties of the antibody molecule. For example, it may be desirable to improve pharmacokinetic properties of antibody molecules, stability e.g. in body fluids such as blood, in particular in the case of single chain antibodies or domain antibodies. A number of technologies have been developed in this regard, in particular to prolong the half-life of such antibody molecules in the circulation, such as pegylation (WO 98/25971; WO 98/48837; WO 2004081026), fusing or otherwise covalently attaching the antibody molecule to another antibody molecule having affinity to a serum protein like albumin (WO 2004041865; WO 2004003019), or expression of the antibody molecule as fusion protein with all or part of a serum protein like albumin or transferrin (WO 01/79258). Means and methods for lead identification and lead optimisation in the design of antibodies are well known in the art and have been reviewed, e.g., in Goulet, D. R. and Atkins, W. M. J Pharm Sci 2020; 109(1):74-103 or Tiller, K. E., & Tessier, P. M. (2015). Annual review of biomedical engineering, 17, 191-216.

In respect of the present invention, the first aspect of the invention provides a binding molecule comprising at least one antigen binding site that binds specifically to TNF-related apoptosis-inducing ligand receptor 2 (TRAILR2) and at least one antigen binding site that binds specifically to cadherin-3 (CDH3). Notably, the CDH3-antigen binding site of the binding molecule of the invention specifically binds to the EC1 domain of CDH3.

"Binding specificity" means that the antibody molecule has a significantly higher binding affinity to the TRAILR2 or CDH3 target antigen than to structurally unrelated molecules.

"Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample.

An epitope is a region of an antigen that is bound by an antibody or antigen binding moiety. The term "epitope" includes any polypeptide determinant capable of specific binding to an antibody or antigen binding moiety. In certain embodiments, epitope determinants include chemically active surface groupings of molecules such as amino acids, glycan side chains, phosphoryl, or sulfonyl, and, in certain embodiments, may have specific three-dimensional structural characteristics, and/or specific charge characteristics. Conformational and nonconformational epitopes are distinguished in that the binding to the former but not the latter is lost in the presence of denaturing solvents. As used herein, the terms "binding" and "specific binding" refer to the binding of the antibody or antigen binding moiety to an epitope of the antigen in an in vitro assay, preferably in a plasmon resonance assay (BIAcore®, GE-Healthcare Uppsala, Sweden) with purified wild-type antigen.

The antibody, or binding molecule described herein, binds to its antigen with an affinity that is at least two-fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis (Munsen, et al. (1980) Analyt. Biochem. 107:220-239).

Affinity is the interaction between a single antigen-binding site on an antibody molecule and a single epitope. It is expressed by the association constant $K_A=k_{ass}/k_{diss}$, or the dissociation constant $K_D=k_{diss}/k_{ass}$ As used herein, the term "binding" or "specifically binding" refers to the binding of the antibody to an epitope of the antigen in an in-vitro assay, preferably in a surface plasmon resonance assay (SPR, BIAcore, GE-Healthcare Uppsala, Sweden), e.g., measured at room temperature. The affinity of the binding is defined by the terms $k_{ass}$ (rate constant for the association of the antibody from the antibody/antigen complex), $k_{diss}$ (dissociation constant), and $K_D$ ($k_{diss}/k_{ass}$). Specific binding commonly refers to the formation of a complex between a receptor molecule and its ligands. In the context of antibody-antigen binding, high affinity antibodies typically bind their target antigens at affinities of $10^{-9}$ M or less.

In one aspect, the antibody binds to the TRAILR2 or CDH3 target antigens with an affinity, as determined e.g. by surface plasmon resonance analysis (Malmqvist M., "Surface plasmon resonance for detection and measurement of antibody-antigen affinity and kinetics.", Curr Opin Immunol. 1993 April; 5(2):282-6.), with a KD value ranging from 1 pM to 100 μM, preferably 1 pM to 1 μM. Antibody affinity can also be measured using kinetic exclusion assay (KinExA) technology (Darling, R. J., and Brault P-A., "Kinetic exclusion assay technology: Characterization of Molecular Interactions." ASSAY and Drug Development Technologies. 2004 Dec. 2(6): 647-657).

The binding affinity of an antibody molecule may be enhanced by a process known as affinity maturation (Marks et al., 1992, Biotechnology 10:779-783; Barbas, et al., 1994, Proc. Nat. Acad. Sci, USA 91:3809-3813; Shier et al., 1995, Gene 169:147-155). Affinity matured antibodies are therefore also embraced in the present invention.

In one embodiment, the bispecific binding molecule of the present invention can induce TRAILR2 mediated apoptosis in one or more cancer cell types, such as the colon adenocarcinoma cell line GP2d or the lung cancer cell line NCI-H358, with more than 50% inhibition of cell growth at a concentration of 1 nM or less, and even more preferably less than 0.01 nM.

In a further embodiment, the binding molecule of the present invention cannot induce TRAILR2 mediated apoptosis in CDH3 negative cells, with less than 50% inhibition of cell growth at a concentration of up to 1 nM, or more preferably up to 10 nM, and even more preferably up to 100 nM.

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, for example from WO 98/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows:

Ala into Gly or into Ser;
Arg into Lys;
Asn into Gln or into His;
Asp into Glu;
Cys into Ser;
Gln into Asn;
Glu into Asp;
Gly into Ala or into Pro;
His into Asn or into Gln;
Ile into Leu or into Val;
Leu into Ile or into Val;
Lys into Arg, into Gln or into Glu;
Met into Leu, into Tyr or into Ile;
Phe into Met, into Leu or into Tyr;
Ser into Thr;
Thr into Ser;
Trp into Tyr;
Tyr into Trp or into Phe;
Val into Ile or into Leu.

The term "isolated," as used herein, refers to material that is removed from its original or native environment (e.g. the natural environment if it is naturally occurring). For example, a naturally-occurring nucleic acid molecule or polypeptide present in a living animal is not isolated, but the same nucleic acid molecule or polypeptide, separated by human intervention from some or all of the co-existing materials in the natural system, is isolated. Such nucleic acid molecules could be part of a vector and/or such nucleic acid molecules or polypeptides could be part of a composition, and still be isolated in that such vector or composition is not part of the environment in which the nucleic acid molecule or the polypeptide is found in nature. For example, a nucleic acid molecule or polypeptide is considered to be "(in) essentially isolated (form)" when, compared to its native biological source and/or the reaction medium or cultivation medium from which it has been obtained, it has been separated from at least one other component with which it is usually associated in said source or medium, such as another nucleic acid molecule, another polypeptide, another biological component or macromolecule or at least one contaminant, impurity or minor component. In particular, a nucleic acid molecule or polypeptide is considered "essentially isolated" when it has been purified at least 2-fold, in particular at least 10-fold, more in particular at least 100-fold, and up to 1000-fold or more. A nucleic acid molecule or polypeptide that is "in essentially isolated form" is preferably essentially homogeneous, as determined using a suitable technique, such as a suitable chromatographical technique, e.g., polyacrylamide-gel-electrophoresis. Binding molecules and nucleic acids of the present invention are preferably isolated.

Unless indicated otherwise, the term "sequence" as used herein (for example in terms like "immunoglobulin sequence", "binding molecule sequence", or "polypeptide sequence"), should generally be understood to include both the relevant amino acid sequence as well as nucleic acid sequences or nucleotide sequences encoding the same, unless the context requires a more limited interpretation.

As used herein, the terms "identical" or "percent identity," in the context of two or more nucleic acid or polypeptide sequences, refer to two or more sequences or sub-sequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, word length=12, to obtain nucleotide sequences homologous to a nucleic acid encoding a protein of interest. BLAST protein searches can be performed with the XBLAST program, score=50, wordlength=3, to obtain amino acid sequences homologous to a protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad.

Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.Preferably, the CLUSTAL W algorithm described above is used.

The term "comprising", as used herein, denotes that further components and/or steps can be included in addition to the specifically recited components and/or steps. However, this term also encompasses that the claimed subject matter consists of exactly the recited components and/or steps.

As used herein, the term "at least", refers to any number including the specifically recited number and any number higher than that. For example, "at least one" encompasses exactly one, as well as more than one, including without being limiting two, such as for example three or four. Further included is e.g. five, six, seven, eight, nine, 10, 15, such as 20, 30, 40, 50, 75, 100, 150, 200, 300, 400 or 500, as well as any integer number in between or above these specifically recited numbers. With regard to the term "at least one antigen binding site", it is particularly preferred that said term encompasses one, two, three or four antigen binding site(s). Most preferably, said term relates to exactly one antigen binding site. In those cases where more than one antigen binding site is chosen for a target, these multiple antigen binding sites can be chosen independently, i.e. they can be identical or they can differ from each other.

The term "polypeptide" as used herein describes linear molecular chains of amino acids, including single chain polypeptides or their fragments, containing more than 30 amino acids. On the other hand, the term "peptide" as used in the present invention describes linear chains of amino acids containing up to 30 amino acids. The term "(poly) peptide" as used in accordance with the present invention refers to a group of molecules which comprises the group of peptides, consisting of up to 30 amino acids, as well as the group of polypeptides, consisting of more than 30 amino acids.

The term "linker", as used herein, encompasses both peptide linkers, i.e. a sequence of amino acids, as well as non-peptide linkers, which covalently or non-covalently connect individual parts of a molecule. The term "non-peptide linker", as used herein, refers to linkage groups having two or more reactive groups but excluding peptide linkers as defined below. For example, the non-peptide linker may be a polymer having reactive groups at both ends, which individually bind to reactive groups of the binding portions of the molecule of the invention, for example, an amino terminus, a lysine residue, a histidine residue or a cysteine residue. The reactive groups of the polymer include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide polymer may be the same or different. For example, the non-peptide polymer may have a maleimide group at one end and an aldehyde group at another end.

Peptide linkers, as envisaged herein, are (poly)peptide linkers of at least 1 amino acid in length. Preferably, the linkers are 1 to 100 amino acids in length. More preferably, the linkers are 5 to 50 amino acids in length, more preferably 10 to 40 amino acids in length, and even more preferably, the linkers are 15 to 30 amino acids in length. Non-limiting examples of often used small linkers include sequences of glycine and serine amino acids, termed GS mini-linker. Preferred examples of linker sequences are Gly/Ser linkers of different length such as $(gly_x ser_y)_z$ linkers, including $(gly_4ser)_3$, $(gly_4ser)_4$, $(gly_4ser)$, $(gly_3ser)$, $gly_3$, and $(gly_3ser_2)_3$. The number of amino acids in these linkers can vary, for example, they can be 4 (e.g., GGGS) (SEQ ID NO:95), 6 (e.g., GGSGGS) (SEQ ID NO:94), 7 (e.g., GGGSGGS (SEQ ID NO:221)), or multiples thereof, such as e.g. two or three or more repeats of these four/six amino acids. Most preferably, such GS mini-linkers have 20 amino acids and the sequence GGGGSGGGGSGGGGSGGGGS (SEQ ID NO:232). Further examples of linkers include the following:

| Linker | Sequence | SEQ ID NO |
|---|---|---|
| 5 GS linker: | GGGGS | 222 |
| 7GS linker: | SGGSGGS | 223 |
| 8GS linker: | GGGGGGGS | 224 |
| 9GS linker: | GGGGSGGGS | 225 |
| 10GS linker: | GGGGSGGGGS | 226 |
| 15GS linker: | GGGGSGGGGSGGGGS | 227 |
| 18GS linker: | GGGGSGGGGSGGGGGGGS | 228 |
| 20GS linker: | GGGGSGGGGSGGGGSGGGGS | 232 |
| 25GS linker: | GGGGSGGGGSGGGGSGGGGSGGGGS | 229 |
| 30GS linker: | GGGGSGGGGSGGGGSGGGGSGGGGSGGGGS | 230 |
| 35GS linker: | GGGGSGGGGSGGGGSGGGGSGGGGSGGGGS GGGGS | 231 |

It will be appreciated by the skilled person that when the molecule of interest is a single polypeptide chain, the linker is a peptide linker.

It is known in the art that the nature, i.e. the length and/or compositions, such as e.g. the amino acid sequence, of the linker may modify or enhance the stability and/or solubility of the molecule which contains the linker. Typically, the length and sequence of a linker is chosen depending on the composition of the respective molecule of interest. The skilled person is well aware of methods to design and test the suitability of different linkers, see e.g. Völkel, T. et al. Protein Engineering, Design and Selection, Volume 14, Issue 10, 2001, Pages 815-823. For example, the properties of the molecule can easily be tested by comparing the binding affinity of the binding portions of the molecule of the invention. In case of the tri-specific molecule of the invention, the respective measurements for each binding portion may be carried out separately. The stability of the resulting molecule can be measured using an ELISA based method to determine the residual binding capacity of the molecule after incubation in human serum at 37° C. for several time periods. Other suitable tests can e.g. be found in Brian R. Miller, B. R. et al. Protein Engineering, Design and Selection, Volume 23, Issue 7, 2010, Pages 549-557 or Kügler, M. et al. Protein Engineering, Design and Selection, Volume 22, Issue 3, 2009, Pages 135-147.

The term "nucleic acid molecule", in accordance with the present invention, which is used interchangeably with the term "polynucleotide" herein, includes DNA, such as for example cDNA or genomic DNA, and RNA, for example mRNA. Further included are nucleic acid mimicking molecules known in the art such as for example synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA). LNA is an RNA derivative in which the ribose ring is constrained by a methylene linkage between the 2'-oxygen and the 4'-carbon. They may contain additional non-natural or derivative nucleotide bases, as will be readily appreciated by those skilled in the art.

Binding Molecules of the Invention

In a first aspect, the invention provides a binding molecule comprising at least one antigen binding site that binds specifically to TNF-related apoptosis-inducing ligand receptor 2 (TRAILR2) and at least one antigen binding site that binds specifically to cadherin-3 (CDH3). Preferably, said at least one antigen binding site binding CDH3 binds specifically to the EC1 domain of CDH3.

Thus, the binding molecule of the invention (also referred to herein as the "protein of the invention" or the "binder of the invention") comprises at least the specifically recited two different antigen binding sites, i.e. at least one binding site for TRAILR2 and at least one binding site for CDH3. Because of the at least two specificities, the binding molecule of the invention is also referred to herein as the "bispecific binding molecule" of the invention.

The term CDH3, as used herein, refers to "cadherin-3", also known as "P-cadherin". CDH3, a member of the cadherin-like superfamily, is a calcium-dependent cell-cell adhesion glycoprotein composed of five extracellular cadherin repeats (ECs), a transmembrane region and a highly conserved cytoplasmic tail. Human CDH3 is represented by SEQ ID NO:98 as well as in database accession number UniProt P22223, available under http://www.uniprot.orgi-uniprot/P22223.

Cadherins are a group of transmembrane proteins that serve as the major adhesion molecules located within adherens junctions. They can regulate cell-cell adhesion through their extracellular domain and their cytosolic domains connect to the actin cytoskeleton by binding to catenins. Structurally, cadherins comprise a number of domains: classically, these include a signal sequence; a propeptide of around 130 residues; a single transmembrane domain and five tandemly repeated extracellular cadherin domains, 4 of which are cadherin repeats, and the fifth typically contains 4 conserved cysteines and a C-terminal cytoplasmic domain. However, proteins are designated as members of the broadly defined cadherin family if they have one or more cadherin repeats. A cadherin repeat is an independently folding sequence of approximately 110 amino acids that typically contains motifs with the conserved sequences DRE, DXNDNAPXF, and DXD.

As used herein, the term "EC1 domain of CDH3" refers to the first of the extracellular cadherin repeats of CDH3. Specifically, the EC1 domain of CDH3 is represented by the amino acid sequence of SEQ ID NO:99.

Accordingly, the term "EC2 domain of CDH3" refers to the second extracellular cadherin repeat of CDH3, represented by SEQ ID NO:100.

The binding molecule of the present invention is not particularly limited with regard to its format, provided that it comprises at least the specifically recited two different antigen binding sites (TRAILR2 and CDH3) and that is capable of binding these two targets. As such, the format can be based on the format of a naturally occurring antibody or of an antibody derivative, or fragments of such antibodies, as well as antibody mimics. Such formats can be modified as needed to accommodate all three antigen binding sites, for example by additionally comprising a further antibody fragment, in particular a Fv, Fab, Fab', or $F(ab')_2$ fragment, a single chain antibody, in particular a single chain variable fragment (scFv), a Small Modular Immunopharmaceutical (SMIP), a domain antibody, or a nanobody. Further non-limiting examples of suitable formats that can be employed, either individually or for all antigen binding sites, include the antibody mimics defined herein above.

In a preferred embodiment, the at least one antigen binding site of the binding molecule described herein that binds specifically cadherin-3 (CDH3) is an immunoglobulin (Ig) molecule (having the conventional Y shaped structure of a full-length antibody comprising two heavy and two light chains) and the at least one antigen binding site that binds specifically to TNF-related apoptosis-inducing ligand receptor 2 (TRAILR2) comprises one or more scFv, scFab, Fab or Fv binding elements. Preferably the antigen binding site that binds specifically to TNF-related apoptosis-inducing ligand receptor 2 (TRAILR2) comprises one or more scFv(s). Even more preferably, the binding molecule described herein comprises two antigen binding sites that bind specifically to TRAILR2, each comprising an scFv, i.e. such binding molecule comprises two scFvs with target specificity to TRAILR2.

A "single chain Fv fragment" (scFv) is a polypeptide comprising an antibody heavy chain variable domain (VH), a linker, and an antibody light chain variable domain (VL), wherein said antibody domains and said linker have one of the following orders in N-terminal to C-terminal direction: a) VH-linker-VL, b) VL-linker-VH, and wherein said linker is a polypeptide of 15 to 25 amino acids, preferably 20 amino acids, in length.

In addition, these single chain Fv fragments might be further stabilized by incorporation of disulfide bonds between the VH and VL domains, within the VH domain, or within the VL domain, via incorporation of cysteine residues. The term N-terminus denotes the first amino acid of the polypeptide chain while the term C-terminus denotes the last amino acid of the C-terminus of the polypeptide chain. Hence an embodiment of the invention is wherein the one or more scFv(s) comprises additional cysteine residues to form disulfide bonds.

In an embodiment of the invention, stability of the scFv moiety can be increased by incorporation of two cysteine residues in close 3-dimensional proximity to form a disulfide bond within the scFv (referred to herein as scFvss). Where the scFv is derived from the V region sequences of TRv1 (as discussed below), example potential sites where such stabilizing disulfide bonds can be engineered include: (a) between position 99 of VL and position 45 of VH, (b) between position 102 of VL and position 44 of VH, (c)

between positions 4 and 100 of VL, and (d) between positions 6 and 112 of VH. To effect stabilization through engineered disulfide bonds, residues at these positions are preferably substituted with cysteine residues.

Preferably, said antigen binding site for TRAILR2 is a scFv that is fused to the C-terminus of the heavy chain of the immunoglobulin molecule; e.g. one scFv that is fused to one of the heavy chains of the Ig molecule, or two scFvs, wherein one scFv is fused to one of the two heavy chains and one scFv is fused to the other heavy chain. Thereby, a modified heavy chain is formed.

In a preferred embodiment, the bispecific binding molecules of the invention comprise modified immunoglobulin molecules in which (i) the immunoglobulin heavy chain comprises an amino acid sequence of a heavy chain variable domain which binds specifically to CDH3, immunoglobulin heavy chain constant domains and also an scFv, which binds specifically to TRAILR2, comprising an amino acid sequence of light chain and heavy chain variable domains, and which scFv is linked to the C-terminal end of the Ig constant domains, and (ii) the immunoglobulin light chain comprises an amino acid sequence of a light chain variable domain which binds specifically to CDH3 and a light chain constant domain. Preferably, the modified immunoglobulin molecules comprise two immunoglobulin heavy chains (e.g. modified heavy chains) and two immunoglobulin light chains.

The fusion of various components to each other is well known in the art. Said fusion can, for example, be via peptide linkers, or via non-peptide linkers. Preferably, said fusion is via (a) peptide linker(s).

In a specific aspect of the invention, the one or more scFv(s) that specifically bind to TRAILR2 are fused to the Ig molecule that specifically binds to CDH3 by a peptide linker, preferably a peptide linker having a length of about 4 to 20 amino acids (e.g., any one of 6, 9, 12, or 15). Preferably the scFv is fused to the C-terminus of the heavy chain of the Ig molecule.

Methods of linking scFv molecules to the C-terminus of the heavy chain of the IgG molecule or linking the variable domains within scFv molecules are well known in the art. Typically a small linker sequence of glycine and serine (also termed a GS mini-linker) amino acids is used.

The number of amino acids in the linker can vary from 4 to 10 or more, as described herein. In practice, normally the linker is formed by combining the nucleic acid molecule encoding the IgG of interest (which in the present case would include the nucleic acid encoding the variable domain of the heavy chain for the CDH3 binding site and constant domains of the IgG type) with the nucleic acid encoding the desired scFv (which in the present case would include the nucleic acid encoding the variable domain of the heavy and light chain, either in VL-VH or VH-VL orientation for the TRAILR2 binding site) interspaced by the nucleic acid molecule encoding the linker sequence (e.g. a GS mini-linker of any one of 5, 10, 15, or 20 amino acids, preferably a linker such as GGGGSGGGGSGGGGSGGGGS (SEQ ID NO:232)). Then as further explained below this complete modified heavy chain encoding nucleic acid molecule is placed within an expression vector and introduced to appropriate host cells such that the complete IgG heavy chain-scFv single polypeptide is formed.

Preferably the linker between the scFv molecule and the C-terminus of the heavy chain of the IgG molecule is GGSGGS (SEQ ID NO:94) or GGGSGGS.

Preferably, said immunoglobulin molecule is a monoclonal, a chimeric, a humanized or a human immunoglobulin (e.g. antibody) molecule. Further preferred is that the heavy chain constant region of said immunoglobulin molecule is selected from the group consisting of IgG1, IgG2, IgG3, IgG4, IgM, IgA and IgE constant regions. In another preferred embodiment, the light chain constant region of said immunoglobulin molecule is kappa or lambda. Preferably, the Ig molecule is an IgG.

In one embodiment, the present invention provides a binding molecule which is a multispecific binding protein comprising (i) one Ig molecule that specifically binds to CDH3 with two heavy and two light chains, and (ii) two scFv molecules (scFv(s)) each that specifically bind to TRAILR2. Preferably, each heavy chain of the Ig molecule has one scFv fused to its C-terminus, thereby forming a bispecific tetravalent binding protein.

In one embodiment, the present invention provides a binding molecule (also referred to herein as multi-specific binding protein or a modified Ig molecule) with:

- (i) two heavy chains (e.g., modified heavy chains), each comprising from N to C terminus:
  - a heavy chain variable domain specific for CDH3 (e.g., murine, humanized or human VH domain), preferably, specific for the EC1 domain of CDH3,
  - constant domains of an IgG (e.g. human IgG1 or IgG4),
  - a peptide linker (e.g. a GS mini linker), and
  - an scFv specific for TRAILR2 (e.g. an scFv comprising from N to C terminus a VH domain (e.g. murine, humanized or human VH domain) a linker and a VL domain (e.g. murine, humanized or human VL domain), or vice versa a VL domain a linker and a VH domain); and
- (ii) two light chains, each comprising from N to C-terminus:
  - a light chain variable domain specific for CDH3 (e.g. murine, humanized or human VL domain), preferably, specific for the EC1 domain of CDH3,
  - a light chain constant domain (e.g., a human kappa chain).

Since the Fc region of an antibody interacts with a number of Fc receptors, which results in a number of important functional capabilities (which are referred to as "effector functions"), the antibody is, in certain embodiments, a full length antibody or an antibody that contains a portion of the Fc region, the latter as long as the antibody exhibits specific binding both to the relevant portion of the antigen and to Fc receptors and complements. The choice of the type and length of the constant region depends on whether effector functions like complement fixation or antibody-dependent cell-mediated cytotoxicity are desirable features, and on the desired pharmacological properties of the antibody protein.

In an embodiment of the invention, the binding molecule of the invention may have an Fc region, or the relevant section thereof, that has been engineered to avoid unintended crosslinking by soluble Fc gamma receptors or complement Cl q. In one embodiment, such binding molecule or antibody variant has much lower affinities to Fcgamma receptors and complement Cl q than the parent antibody. (In the following, if not otherwise stated, the term "parent" in the context of an antibody molecule, or in the context of IgG or the Fc region, refers to the non-engineered antibody molecule, Fc region or IgG, respectively, from which the mutated (engineered) molecule is derived.). Hence an embodiment of the invention is wherein the Ig molecule comprises a Fc variant having a reduced affinity to Fc gamma receptors or complement receptors or both compared to a wildtype Fc region. Such Ig molecule is referred to herein as IgG1(KO).

A further embodiment of the invention is wherein the binding molecule of the invention comprises an Fc region, or the relevant section thereof, that has been engineered to modify serum levels (half-life) by optimizing its interaction with the neonatal Fc receptor (FcRn), e.g. by a point mutation in the CH2 domain at position H310A). Such Ig molecule is referred to herein as IgG1 FcRnmut.

A further embodiment of the invention is wherein the binding molecule comprises an Ig molecule which comprises a hinge region variant of IgG4 that ablates swapping of the heavy chains with other IgG4 molecules. Such Ig molecule is referred to herein as IgG4Pro.

The present invention provides a bispecific binding molecule having at least one antigen binding site that binds specifically to TNF-related apoptosis-inducing ligand receptor 2 (TRAILR2) and at least one antigen binding site that binds specifically to cadherin-3 (CDH3).

Methods of preparing binding sites that bind to specific target antigens are well known in the art. The skilled person can readily use these methods to devise an antigen binding site having the necessary specificity for the TRAILR2 or CDH3 target antigens.

Methods of generating antibodies and antibody fragments are well known in the art. For example, antibodies may be generated via any one of several methods which employ induction of in vivo production of antibody molecules, screening of immunoglobulin libraries (Orlandi et al, 1989. Proc. Natl. Acad. Sci. U.S.A. 86:3833-3837; Winter et al 1991, Nature 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al 1975. Nature 20 256:4950497; Kozbor et al 1985. J. Immunol. Methods 81:31-42; Cote et al 1983. Proc. Natl. Acad. Sci. USA 80:2026-2030; Cole et al 1984. Mol. Cell. Biol. 62:109-120).

In some embodiments, the antigen binding site (for CDH3 and/or TrailR2) is a “humanized” antigen binding site (e.g., comprising humanized VH/VL domain) comprising amino acid residues from non-human hypervariable regions (HVRs; e.g. complementary determining regions (CDRs)) and amino acid residues from human frame work sequences. In some embodiments, the antigen binding site (for CDH3 and/or TRAILR2) is a human antigen binding site (e.g. comprising human VH/VL domain) comprising CDR and FR sequences which are both derived from sequences of the human genome.

The amino acid sequences of the specific antigen binding sites are provided in the description and the sequence listing.

Provided below are details of preferred embodiments of the invention which comprise specific antigen binding sites for TRAILR2 and/or CDH3.

In a preferred embodiment, the at least one antigen binding site that binds specifically to CDH3 comprises heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3).

In a further preferred embodiment, the at least one antigen binding site that binds specifically to CDH3 comprises heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3).

In a further preferred embodiment, the at least one antigen binding site that binds specifically to CDH3 comprises heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3).

In a further preferred embodiment, the at least one antigen binding site that binds specifically to CDH3 comprises heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3).

In a preferred embodiment of the binding molecule of the invention, the at least one antigen binding site that binds specifically to TRAILR2 comprises heavy chain CDRs comprising the amino acid sequences of SEQ ID NO:73 (CDR1), SEQ ID NO:74 (CDR2) and SEQ ID NO:75 (CDR3) and light chain CDRs comprising the amino acid sequences of SEQ ID NO:77 (CDR1), SEQ ID NO:78 (CDR2) and SEQ ID NO:79 (CDR3).

Thus, in a specific aspect, the binding molecule described herein comprises an antigen binding site that specifically binds to CDH3, which comprises heavy chain CDRs comprising the amino acid sequences of SEQ ID NO:3 (HCDR1), SEQ ID NO:4 (HCDR2) and SEQ ID NO:5 (HCDR3) and light chain CDRs comprising the amino acid sequences of SEQ ID NO:7 (LCDR1), SEQ ID NO:8 (LCDR2) and SEQ ID NO:9 (LCDR3); and at least one, preferably two, antigen binding site(s) that bind specifically to TRAILR2 which comprises heavy chain CDRs comprising the amino acid sequences of SEQ ID NO:73 (HCDR1), SEQ ID NO:74 (HCDR2) and SEQ ID NO:75 (HCDR3) and light chain CDRs comprising the amino acid sequences of SEQ ID NO:77 (LCDR1), SEQ ID NO:78 (LCDR2) and SEQ ID NO:79 (LCDR3).

In a further specific aspect, the binding molecule described herein comprises an antigen binding site that specifically binds to CDH3, which comprises heavy chain CDRs comprising the amino acid sequences of SEQ ID NO:13 (HCDR1), SEQ ID NO:14 (HCDR2) and SEQ ID NO:15 (HCDR3) and light chain CDRs comprising the amino acid sequences of SEQ ID NO:17 (LCDR1), SEQ ID NO:18 (LCDR2) and SEQ ID NO:19 (LCDR3); and at least one, preferably two, antigen binding site(s) that bind specifically to TRAILR2 which comprises heavy chain CDRs comprising the amino acid sequences of SEQ ID NO:73 (HCDR1), SEQ ID NO:74 (HCDR2) and SEQ ID NO:75 (HCDR3) and light chain CDRs comprising the amino acid sequences of SEQ ID NO:77 (LCDR1), SEQ ID NO:78 (LCDR2) and SEQ ID NO:79 (LCDR3).

In a further specific aspect, the binding molecule described herein comprises an antigen binding site that specifically binds to CDH3, which comprises heavy chain CDRs comprising the amino acid sequences of SEQ ID NO:23 (HCDR1), SEQ ID NO:24 (HCDR2) and SEQ ID NO:25 (HCDR3) and light chain CDRs comprising the amino acid sequences of SEQ ID NO:27 (LCDR1), SEQ ID NO:28 (LCDR2) and SEQ ID NO:29 (LCDR3); and at least one, preferably two, antigen binding site(s) that bind specifically to TRAILR2 which comprises heavy chain CDRs comprising the amino acid sequences of SEQ ID NO:73 (HCDR1), SEQ ID NO:74 (HCDR2) and SEQ ID NO:75 (HCDR3) and light chain CDRs comprising the amino acid sequences of SEQ ID NO:77 (LCDR1), SEQ ID NO:78 (LCDR2) and SEQ ID NO:79 (LCDR3).

In yet a further specific aspect, the binding molecule described herein comprises an antigen binding site that specifically binds to CDH3, which comprises heavy chain CDRs comprising the amino acid sequences of SEQ ID NO:33 (HCDR1), SEQ ID NO:34 (HCDR2) and SEQ ID NO:35 (HCDR3) and light chain CDRs comprising the amino acid sequences of SEQ ID NO:37 (LCDR1), SEQ ID NO:38 (LCDR2) and SEQ ID NO:39 (LCDR3); and at least one, preferably two, antigen binding site(s) that bind specifically to TRAILR2 which comprises heavy chain CDRs comprising the amino acid sequences of SEQ ID NO:73 (HCDR1), SEQ ID NO:74 (HCDR2) and SEQ ID NO:75 (HCDR3) and light chain CDRs comprising the amino acid sequences of SEQ ID NO:77 (LCDR1), SEQ ID NO:78 (LCDR2) and SEQ ID NO:79 (LCDR3).

The CDRs disclosed herein and depicted in the SEQ ID Nos above are presented according to the Kabat nomenclature and are shown in table 1 below. As used herein, HCDR stands for heavy chain CDR and LCDR for light chain CDR.

As additional nomenclatures are known in the art, the CDR sequences based on the most commonly used of these nomenclatures are shown in table 1 below as well. These numbering systems are based on (i) CCG (Chemical Computing Group as illustrated in Almagro et al., Proteins 2011; 79:3050-3066 and Maier et al, Proteins 2014; 82:1599-1610), (ii) Chothia (Chothia and Lesk, 1987, J. Mol. Biol. 196: 901-917), (iii) IMGT (Lefranc M P, Dev Comp Immunol. 2003 January; 27(1):55-77) and (iv) North (North B, J Mol Biol. (2011) 406:228-56).

TABLE 1

Amino acid sequences and SEQ ID NOs of CDRs comprised in the binding molecules of the invention:

| SEQ ID Number | Description of Sequence | Nomenclature | Sequence |
|---|---|---|---|
| 3 | CDH3v7 | Kabat | SYYWS |
| 101 | HCDR1 | Chothia | GGSISSY |
| 102 | | IMGT | GGSISSYY |
| 103 | | CCG | GGSISSYYWS |
| 104 | | North | TVSGGSISSYYWS |
| 4 | CDH3v7 | Kabat | YIYYSRTTNYNPSLKS |
| 105 | HCDR2 | Chothia | YYSRT |
| 106 | | IMGT | IYYSRTT |
| 107 | | CCG | YIYYSRTTNYNPSLKS |
| 108 | | North | YIYYSRTTN |
| 5 | CDH3v7 | Kabat | ARNGIDAFDI |
| 109 | HCDR3 | Chothia | ARNGIDAFDI |
| 110 | | IMGT | ARARNGIDAFDI |
| 111 | | CCG | ARNGIDAFDI |
| 112 | | North | ARARNGIDAFDI |
| 7 | CDH3v7 | Kabat | RSSQSLLHSYGYNYLD |
| 113 | LCDR1 | Chothia | RSSQSLLHSYGYNYLD |
| 114 | | IMGT | QSLLHSYGYNY |
| 115 | | CCG | RSSQSLLHSYGYNYLD |
| 116 | | North | RSSQSLLHSYGYNYLD |
| 8 | CDH3v7 | Kabat | LGSNRAS |
| 117 | LCDR2 | Chothia | LGSNRAS |
| 118 | | IMGT | LGS |
| 119 | | CCG | LGSNRAS |
| 120 | | North | YLGSNRAS |
| 9 | CDH3v7 | Kabat | MQALQTPLT |
| 121 | LCDR3 | Chothia | MQALQTPLT |
| 122 | | IMGT | MQALQTPLT |
| 123 | | CCG | MQALQTPLT |
| 124 | | North | MQALQTPLT |
| 13 | CDH3v1 | Kabat | SYWIG |
| 125 | HCDR1 | Chothia | GYSFTSY |
| 126 | | IMGT | GYSFTSYW |
| 127 | | CCG | GYSFTSYWIG |
| 128 | | North | KGSGYSFTSYWIG |
| 14 | CDH3v1 | Kabat | IIYPGDSDTRYSPSFQG |
| 129 | HCDR2 | Chothia | YPGDSD |
| 130 | | IMGT | IYPGDSDT |
| 131 | | CCG | IIYPGDSDTRYSPSFQG |
| 132 | | North | IIYPGDSDTR |
| 15 | CDH3v1 | Kabat | HSFFDY |
| 133 | HCDR3 | Chothia | HSFFDY |
| 134 | | IMGT | ARHSFFDY |
| 135 | | CCG | HSFFDY |
| 136 | | North | ARHSFFDY |

TABLE 1-continued

Amino acid sequences and SEQ ID NOs of CDRs comprised in the binding molecules of the invention:

| SEQ ID Number | Description of Sequence | Nomenclature | Sequence |
|---|---|---|---|
| 17 | CDH3v1 | Kabat | RASQSVSSIYLA |
| 137 | LCDR1 | Chothia | RASQSVSSIYLA |
| 138 | | IMGT | QSVSSIY |
| 139 | | CCG | RASQSVSSIYLA |
| 140 | | North | RASQSVSSIYLA |
| 18 | CDH3v1 | Kabat | GASSRAT |
| 141 | LCDR2 | Chothia | GASSRAT |
| 142 | | IMGT | GAS |
| 143 | | CCG | GASSRAT |
| 144 | | North | YGASSRAT |
| 19 | CDH3v1 | Kabat | QQYSSSPRT |
| 145 | LCDR3 | Chothia | QQYSSSPRT |
| 146 | | IMGT | QQYSSSPRT |
| 147 | | CCG | QQYSSSPRT |
| 148 | | North | QQYSSSPRT |
| 23 | CDH3v2 | Kabat | NYYWS |
| 149 | HCDR1 | Chothia | GGSISNY |
| 150 | | IMGT | GGSISNYY |
| 151 | | CCG | GGSISNYYWS |
| 152 | | North | TVSGGSISNYYWS |
| 24 | CDH3v2 | Kabat | YMYYSGITNYNPSLKS |
| 153 | HCDR2 | Chothia | YYSGI |
| 154 | | IMGT | MYYSGIT |
| 155 | | CCG | YMYYSGITNYNPSLKS |
| 156 | | North | YMYYSGITN |
| 25 | CDH3v2 | Kabat | ERNGIDGMDV |
| 157 | HCDR3 | Chothia | ERNGIDGMDV |
| 158 | | IMGT | ARERNGIDGMDV |
| 159 | | CCG | ERNGIDGMDV |
| 160 | | North | ARERNGIDGMDV |
| 27 | CDH3v2 | Kabat | RSSQSLLHSYGYNYLD |
| 161 | LCDR1 | Chothia | RSSQSLLHSYGYNYLD |
| 162 | | IMGT | QSLLHSYGYNY |
| 163 | | CCG | RSSQSLLHSYGYNYLD |
| 164 | | North | RSSQSLLHSYGYNYLD |
| 28 | CDH3v2 | Kabat | LGSNRAS |
| 165 | LCDR2 | Chothia | LGSNRAS |
| 166 | | IMGT | LGS |
| 167 | | CCG | LGSNRAS |
| 168 | | North | YLGSNRAS |
| 29 | CDH3v2 | Kabat | MQALQTPIT |
| 169 | LCDR3 | Chothia | MQALQTPIT |
| 170 | | IMGT | MQALQTPIT |
| 171 | | CCG | MQALQTPIT |
| 172 | | North | MQALQTPIT |
| 33 | CDH3v3 | Kabat | GYYWS |
| 173 | HCDR1 | Chothia | GGSISGY |
| 174 | | IMGT | GGSISGYY |
| 175 | | CCG | GGSISGYYWS |
| 176 | | North | TVSGGSISGYYWS |
| 34 | | Kabat | YIYYSANTNYNPSLKS |
| 177 | CDH3v3 | Chothia | YYSAN |
| 178 | HCDR2 | IMGT | IYYSANT |
| 179 | | CCG | YIYYSANTNYNPSLKS |
| 180 | | North | YIYYSANTN |
| 35 | CDH3v3 | Kabat | GGSGSYWAFDI |
| 181 | HCDR3 | Chothia | GGSGSYWAFDI |
| 182 | | IMGT | SRGGSGSYWAFDI |
| 183 | | CCG | GGSGSYWAFDI |
| 184 | | North | SRGGSGSYWAFDI |

TABLE 1-continued

Amino acid sequences and SEQ ID NOs of CDRs comprised in the binding molecules of the invention:

| SEQ ID Number | Description of Sequence | Nomenclature | Sequence |
|---|---|---|---|
| 37 | CDH3v3 | Kabat | RSSQSLMYSYGYNYLD |
| 185 | LCDR1 | Chothia | RSSQSLMYSYGYNYLD |
| 186 | | IMGT | QSLMYSYGYNY |
| 187 | | CCG | RSSQSLMYSYGYNYLD |
| 188 | | North | RSSQSLMYSYGYNYLD |
| 38 | CDH3v3 | Kabat | LGSNRAS |
| 189 | LCDR2 | Chothia | LGSNRAS |
| 190 | | IMGT | LGS |
| 191 | | CCG | LGSNRAS |
| 192 | | North | YLGSNRAS |
| 39 | CDH3v3 | Kabat | MQALQTPPT |
| 193 | LCDR3 | Chothia | MQALQTPPT |
| 194 | | IMGT | MQALQTPPT |
| 195 | | CCG | MQALQTPPT |
| 196 | | North | MQALQTPPT |
| 73 | TRAILR2 | Kabat | DYGMS |
| 197 | HCDR1 | Chothia | GFTFDDY |
| 198 | | IMGT | GFTFDDYG |
| 199 | | CCG | GFTFDDYGMS |
| 200 | | North | AASGFTFDDYGMS |
| 74 | TRAILR2 | Kabat | GINWNGGSTGYADSVKG |
| 201 | HCDR2 | Chothia | NWNGGS |
| 202 | | IMGT | INWNGGST |
| 203 | | CCG | GINWNGGSTGYADSVKG |
| 204 | | North | GINWNGGSTG |
| 75 | TRAILR2 | Kabat | ILGAGRGWYFDL |
| 205 | HCDR3 | Chothia | ILGAGRGWYFDL |
| 206 | | IMGT | AKILGAGRGWYFDL |
| 207 | | CCG | ILGAGRGWYFDL |
| 208 | | North | AKILGAGRGWYFDL |
| 77 | TRAILR2 | Kabat | QGDSLRSYYAS |
| 209 | LCDR1 | Chothia | QGDSLRSYYAS |
| 210 | | IMGT | SLRSYY |
| 211 | | CCG | QGDSLRSYYAS |
| 212 | | North | QGDSLRSYYAS |
| 78 | TRAILR2 | Kabat | GKNNRPS |
| 213 | LCDR2 | Chothia | GKNNRPS |
| 214 | | IMGT | GKN |
| 215 | | CCG | GKNNRPS |
| 216 | | North | YGKNNRPS |
| 79 | TRAILR2 | Kabat | NSRDSSGNHVV |
| 217 | LCDR3 | Chothia | NSRDSSGNHVV |
| 218 | | IMGT | NSRDSSGNHVV |
| 219 | | CCG | NSRDSSGNHVV |
| 220 | | North | NSRDSSGNHVV |

The amino acid positions indicated for CDRs herein (see table 1) according to Kabat, CCG, Chothia, IMGT and North positions are linear, i.e. the amino acids of the respective full length molecule chain are consecutively numbered starting from number 1 at the N-terminus and end with the number that corresponds to the total number of amino acids in said molecule. For example, a heavy chain consisting of 118 amino acids in length will start with number 1 at the N-terminus and will end with number 118 at the most C-terminal amino acid. Thus, any reference to e.g. position 25 means that the amino acid number 25 as counted from the N-terminus of this molecule is referred to.

In a preferred embodiment of the binding molecule of the present invention, the at least one antigen binding site that binds specifically to CDH3 comprises an immunoglobulin heavy chain variable domain (VH) comprising the amino acid sequence of SEQ ID NO:2 and an immunoglobulin light chain variable domain (VL) comprising the amino acid sequence of SEQ ID NO:6.

In a preferred embodiment of the binding molecule of the present invention, the at least one antigen binding site that binds specifically to CDH3 comprises a VH comprising the amino acid sequence of SEQ ID NO:12 and a VL comprising the amino acid sequence of SEQ ID NO:16.

In a preferred embodiment of the binding molecule of the present invention, the at least one antigen binding site that binds specifically to CDH3 comprises a VH comprising the amino acid sequence of SEQ ID NO:22 and a VL comprising the amino acid sequence of SEQ ID NO:26.

In a preferred embodiment of the binding molecule of the present invention, the at least one antigen binding site that binds specifically to CDH3 comprises a VH comprising the amino acid sequence of SEQ ID NO:32 and a VL comprising the amino acid sequence of SEQ ID NO:36.

In accordance with the present invention, the terms “immunoglobulin heavy chain variable domain” and “immunoglobulin light chain variable domain” are used in accordance with the definitions in the art.

Specifically, the binding molecule of the present invention, the at least one antigen binding site for CDH3 is selected from the antigen binding sites described herein above, whereas the antigen binding site for TRAILR2 is chosen by the skilled person either from those TRAILR2-specific antigen binding sites available in the art or from those disclosed herein.

Preferably, said antigen binding site that binds specifically to TRAILR2 is a single-chain variable fragment (scFv). More preferably, said scFv is arranged such that the heavy chain variable domain is at its N-terminus and the light chain variable domain is at its C-terminus.

Methods of linking polypeptides of interest, including scFv molecules, to e.g. the C-terminus of the heavy chain of an IgG molecule are well known in the art. It will be appreciated that said fusion of the scFv to the Ig molecule can be either a direct fusion or can be via a linker, preferably a peptide linker, as described above. In practice, the linkage is typically achieved by combining the nucleic acid molecule encoding the IgG of interest with the nucleic acid encoding the desired polypeptide, e.g. the scFv, where necessary interspaced by the nucleic acid molecule encoding the linker sequence, thereby forming a single nucleic acid molecule comprising all three elements. Then, this complete HC-scFv encoding nucleic acid molecule is placed within an expression vector and introduced to appropriate host cells such that the complete IgG heavy chain-scFv single polypeptide is formed and optionally, the same is done for the IgG light chain-scFv counterpart.

In a specific embodiment of the binding molecule of the invention, the antigen binding site that binds specifically to TRAILR2 (the first antigen binding site) is an antigen binding site comprising an immunoglobulin heavy chain variable domain comprising the amino acid sequence of SEQ ID NO:72 and an immunoglobulin light chain variable domain comprising the amino acid sequence of SEQ ID NO:76.

Thus, in a specific aspect, the binding molecule described herein comprises an antigen binding site that specifically binds to CDH3 comprising an immunoglobulin heavy chain variable domain comprising the amino acid sequence of SEQ ID NO:2 and an immunoglobulin light chain variable domain comprising the amino acid sequence of SEQ ID NO:6; and at least one, preferably two, antigen binding site(s) that bind specifically to TRAILR2 comprising an immunoglobulin heavy chain variable domain comprising the amino acid sequence of SEQ ID NO:72 and an immunoglobulin light chain variable domain comprising the amino acid sequence of SEQ ID NO:76.

In a further a specific aspect, the binding molecule described herein comprises an antigen binding site that specifically binds to CDH3 comprising an immunoglobulin heavy chain variable domain comprising the amino acid sequence of SEQ ID NO:12 and an immunoglobulin light chain variable domain comprising the amino acid sequence of SEQ ID NO:16; and at least one, preferably two, antigen binding site(s) that bind specifically to TRAILR2 comprising an immunoglobulin heavy chain variable domain comprising the amino acid sequence of SEQ ID NO:72 and an immunoglobulin light chain variable domain comprising the amino acid sequence of SEQ ID NO:76.

In a further a specific aspect, the binding molecule described herein comprises an antigen binding site that specifically binds to CDH3 comprising an immunoglobulin heavy chain variable domain comprising the amino acid sequence of SEQ ID NO:22 and an immunoglobulin light chain variable domain comprising the amino acid sequence of SEQ ID NO:26; and at least one, preferably two, antigen binding site(s) that bind specifically to TRAILR2 comprising an immunoglobulin heavy chain variable domain comprising the amino acid sequence of SEQ ID NO:72 and an immunoglobulin light chain variable domain comprising the amino acid sequence of SEQ ID NO:76.

In yet a further specific aspect, the binding molecule described herein comprises an antigen binding site that specifically binds to CDH3 comprising an immunoglobulin heavy chain variable domain comprising the amino acid sequence of SEQ ID NO:32 and an immunoglobulin light chain variable domain comprising the amino acid sequence of SEQ ID NO:36; and at least one, preferably two, antigen binding site(s) that bind specifically to TRAILR2 comprising an immunoglobulin heavy chain variable domain comprising the amino acid sequence of SEQ ID NO:72 and an immunoglobulin light chain variable domain comprising the amino acid sequence of SEQ ID NO:76.

In a preferred embodiment of the invention, the binding molecule comprises:

i. a heavy chain comprising the amino acid sequence of SEQ ID NO:80 and a light chain comprising the amino acid sequence of SEQ ID NO:81;
ii. a heavy chain comprising the amino acid sequence of SEQ ID NO:82 and a light chain comprising the amino acid sequence of SEQ ID NO:83;
iii. a heavy chain comprising the amino acid sequence of SEQ ID NO:84 and a light chain comprising the amino acid sequence of SEQ ID NO:85; or
iv. a heavy chain comprising the amino acid sequence of SEQ ID NO:86 and a light chain comprising the amino acid sequence of SEQ ID NO:87.

In a specific embodiment, the binding molecule provided herein comprises:

i. a heavy chain comprising the amino acid sequence of SEQ ID NO:80, or an amino acid sequence that is at least 80%, at least 90%, at least 95%, at least 98%, or at least 99% identical to SEQ ID NO:80, and a light chain comprising the amino acid sequence of SEQ ID NO:81, or an amino acid sequence that is at least 80%, at least 90%, at least 95%, at least 98%, or at least 99% identical to SEQ ID NO:81;
ii. a heavy chain comprising the amino acid sequence of SEQ ID NO:82, or an amino acid sequence that is at least 80%, at least 90%, at least 95%, at least 98%, or at least 99% identical to SEQ ID NO:82, and a light chain comprising the amino acid sequence of SEQ ID NO:83, or an amino acid sequence that is at least 80%, at least 90%, at least 95%, at least 98%, or at least 99% identical to SEQ ID NO:83;
iii. a heavy chain comprising the amino acid sequence of SEQ ID NO:84, or an amino acid sequence that is at least 80%, at least 90%, at least 95%, at least 98%, or at least 99% identical to SEQ ID NO:84, and a light chain comprising the amino acid sequence of SEQ ID NO:85, or an amino acid sequence that is at least 80%, at least 90%, at least 95%, at least 98%, or at least 99% identical to SEQ ID NO:85; or iv. a heavy chain comprising the amino acid sequence of SEQ ID NO:86, or an amino acid sequence that is at least 80%, at least 90%, at least 95%, at least 98%, or at least 99% identical to SEQ ID NO:86, and a light chain comprising the amino acid sequence of SEQ ID NO:87, or an amino acid sequence that is at least 80%, at least 90%, at least 95%, at least 98%, or at least 99% identical to SEQ ID NO:87.

In a specific aspect, the binding molecule described herein thus comprises a heavy chain comprising the amino acid sequence of SEQ ID NO:80, or an amino acid sequence that is at least 80%, at least 90%, at least 95%, at least 98%, or at least 99% identical to SEQ ID NO:80, and a light chain comprising the amino acid sequence of SEQ ID NO:81, or an amino acid sequence that is at least 80%, at least 90%, at least 95%, at least 98%, or at least 99% identical to SEQ ID NO:81; and at least one, preferably two, scFv(s) having target specificity for TRAILR2 and comprising or consisting of an immunoglobulin heavy chain variable domain having the amino acid sequence of SEQ ID NO:72, or an amino acid sequence that is at least 80%, at least 90%, at least 95%, at least 98%, or at least 99% identical to SEQ ID NO:72, and an immunoglobulin light chain variable domain having the amino acid sequence of SEQ ID NO:76, or an amino acid sequence that is at least 80%, at least 90%, at least 95%, at least 98%, or at least 99% identical to SEQ ID NO:76. In a preferred embodiment, the at least one scFv(s) that bind specifically to TRAILR2 comprise the amino acid sequence of SEQ ID NO. 71.

In a further specific aspect, the binding molecule described herein thus comprises a heavy chain comprising the amino acid sequence of SEQ ID NO:82, or an amino acid sequence that is at least 80%, at least 90%, at least 95%, at least 98%, or at least 99% identical to SEQ ID NO:82, and a light chain comprising the amino acid sequence of SEQ ID NO:83, or an amino acid sequence that is at least 80%, at least 90%, at least 95%, at least 98%, or at least 99% identical to SEQ ID NO:83; and at least one, preferably two, scFv(s) having target specificity for TRAILR2 and comprising or consisting of an immunoglobulin heavy chain variable domain having the amino acid sequence of SEQ ID NO:72, or an amino acid sequence that is at least 80%, at least 90%, at least 95%, at least 98%, or at least 99% identical to SEQ ID NO:72, and an immunoglobulin light chain variable domain having the amino acid sequence of SEQ ID NO:76, or an amino acid sequence that is at least 80%, at least 90%, at least 95%, at least 98%, or at least 99% identical to SEQ ID NO:76. In a preferred embodiment, the at least one scFv(s) that bind specifically to TRAILR2 comprise the amino acid sequence of SEQ ID NO. 71.

In a further specific aspect, the binding molecule described herein thus comprises a heavy chain comprising the amino acid sequence of SEQ ID NO:84, or an amino acid sequence that is at least 80%, at least 90%, at least 95%, at least 98%, or at least 99% identical to SEQ ID NO:84, and a light chain comprising the amino acid sequence of SEQ ID NO:85, or an amino acid sequence that is at least 80%, at least 90%, at least 95%, at least 98%, or at least 99% identical to SEQ ID NO:85; and at least one, preferably two, scFv(s) having target specificity for TRAILR2 and comprising or consisting of an immunoglobulin heavy chain variable domain having the amino acid sequence of SEQ ID NO:72, or an amino acid sequence that is at least 80%, at least 90%, at least 95%, at least 98%, or at least 99% identical to SEQ ID NO:72, and an immunoglobulin light chain variable domain having the amino acid sequence of SEQ ID NO:76, or an amino acid sequence that is at least 80%, at least 90%, at least 95%, at least 98%, or at least 99% identical to SEQ ID NO:76. In a preferred embodiment, the at least one scFv(s) that bind specifically to TRAILR2 comprise the amino acid sequence of SEQ ID NO. 71.

In yet a further specific aspect, the binding molecule described herein thus comprises a heavy chain comprising the amino acid sequence of SEQ ID NO:86, or an amino acid sequence that is at least 80%, at least 90%, at least 95%, at least 98%, or at least 99% identical to SEQ ID NO:86, and a light chain comprising the amino acid sequence of SEQ ID NO:87, or an amino acid sequence that is at least 80%, at least 90%, at least 95%, at least 98%, or at least 99% identical to SEQ ID NO:87; and at least one, preferably two, scFv(s) having target specificity for TRAILR2 and comprising or consisting of an immunoglobulin heavy chain variable domain having the amino acid sequence of SEQ ID NO:72, or an amino acid sequence that is at least 80%, at least 90%, at least 95%, at least 98%, or at least 99% identical to SEQ ID NO:72, and an immunoglobulin light chain variable domain having the amino acid sequence of SEQ ID NO:76, or an amino acid sequence that is at least 80%, at least 90%, at least 95%, at least 98%, or at least 99% identical to SEQ ID NO:76. In a preferred embodiment, the at least one scFv(s) that bind specifically to TRAILR2 comprise the amino acid sequence of SEQ ID NO. 71.

In a specific embodiment, the binding molecule of the invention comprises a modified heavy chain, preferably wherein a TRAILR2-specific scFv is fused to the C-terminus of an Ig heavy chain. Preferably, said modified heavy chain comprises the amino acid sequence of SEQ ID NO:1, SEQ ID NO:11, SEQ ID NO:21, or SEQ ID NO:31. Specifically, the binding molecule of the invention comprises an amino acid sequence that is at least 80%, at least 90%, at least 95%, at least 98%, or at least 99% identical to SEQ ID NO:1, SEQ ID NO:11, SEQ ID NO:21, or SEQ ID NO:31.

Specifically, the binding molecule of the invention comprises:

i. a modified heavy chain comprising the amino acid sequence of SEQ ID NO:1 and a light chain comprising the amino acid sequence of SEQ ID NO:81;

ii. a modified heavy chain comprising the amino acid sequence of SEQ ID NO:11 and a light chain comprising the amino acid sequence of SEQ ID NO:83;

iii. a modified heavy chain comprising the amino acid sequence of SEQ ID NO:21 and a light chain comprising the amino acid sequence of SEQ ID NO:85; or iv. a modified heavy chain comprising the amino acid sequence of SEQ ID NO:31 and a light chain comprising the amino acid sequence of SEQ ID NO:87.

In a preferred embodiment, the binding molecule described herein thus comprises a modified heavy chain comprising the amino acid sequence of SEQ ID NO:1, or an amino acid sequence that is at least 80%, at least 90%, at least 95%, at least 98%, or at least 99% identical to SEQ ID NO:1, and a light chain comprising the amino acid sequence of SEQ ID NO:81, or an amino acid sequence that is at least 80%, at least 90%, at least 95%, at least 98%, or at least 99% identical to SEQ ID NO:81.

In a further preferred embodiment, the binding molecule described herein thus comprises a modified heavy chain comprising the amino acid sequence of SEQ ID NO:11, or an amino acid sequence that is at least 80%, at least 90%, at least 95%, at least 98%, or at least 99% identical to SEQ ID NO:11, and a light chain comprising the amino acid sequence of SEQ ID NO:83, or an amino acid sequence that is at least 80%, at least 90%, at least 95%, at least 98%, or at least 99% identical to SEQ ID NO:83.

In a further preferred embodiment, the binding molecule described herein thus comprises a modified heavy chain comprising the amino acid sequence of SEQ ID NO:21, or an amino acid sequence that is at least 80%, at least 90%, at least 95%, at least 98%, or at least 99% identical to SEQ ID NO:21, and a light chain comprising the amino acid sequence of SEQ ID NO:85, or an amino acid sequence that is at least 80%, at least 90%, at least 95%, at least 98%, or at least 99% identical to SEQ ID NO:85.

In a further preferred embodiment, the binding molecule described herein thus comprises a modified heavy chain comprising the amino acid sequence of SEQ ID NO:31, or an amino acid sequence that is at least 80%, at least 90%, at least 95%, at least 98%, or at least 99% identical to SEQ ID NO:31, and a light chain comprising the amino acid sequence of SEQ ID NO:87, or an amino acid sequence that is at least 80%, at least 90%, at least 95%, at least 98%, or at least 99% identical to SEQ ID NO:87.

Further described herein are bispecific binding molecules having at least one antigen binding site (a first antigen binding site) that binds specifically to TNF-related apoptosis inducing ligand receptor 2 (TRAILR2), as described in detail above, and at least one antigen binding site (a second antigen binding site) that binds specifically to the extracellular domain 2 (EC2 domain) of cadherin-3 (CDH3).

In one aspect, the binding molecule provided herein thus binds to an antigen comprising or consisting of SEQ ID NO:100, or an amino acid sequence that is at least 80%, at least 90%, at least 95%, at least 98%, or at least 99% identical to SEQ ID NO:100.

Preferably, said at least one antigen binding site that binds specifically to the EC2 domain of CDH3 is selected from the group consisting of:

i. an antigen binding site comprising heavy chain CDRs comprising the amino acid sequences of SEQ ID NO:43 (CDR1), SEQ ID NO:44 (CDR2) and SEQ ID NO:45 (CDR3) and light chain CDRs comprising the amino acid sequences of SEQ ID NO:47 (CDR1), SEQ ID NO:48 (CDR2) and SEQ ID NO:49 (CDR3);
ii. an antigen binding site comprising heavy chain CDRs comprising the amino acid sequences of SEQ ID NO:53 (CDR1), SEQ ID NO:54 (CDR2) and SEQ ID NO:55 (CDR3) and light chain CDRs comprising the amino acid sequences of SEQ ID NO:57 (CDR1), SEQ ID NO:58 (CDR2) and SEQ ID NO:59 (CDR3); and
iii. an antigen binding site comprising heavy chain CDRs comprising the amino acid sequences of SEQ ID NO:63 (CDR1), SEQ ID NO:64 (CDR2) and SEQ ID NO:65 (CDR3) and light chain CDRs comprising the amino acid sequences of SEQ ID NO:67 (CDR1), SEQ ID NO:68 (CDR2) and SEQ ID NO:69 (CDR3).

Even more preferably, the antigen binding site that binds specifically to the EC2 domain of CDH3 is selected from the group consisting of:

i. a VH comprising the amino acid sequence of SEQ ID NO:42 and a VL comprising the amino acid sequence of SEQ ID NO:46;
ii. a VH comprising the amino acid sequence of SEQ ID NO:52 and a VL comprising the amino acid sequence of SEQ ID NO:56; and
iii. a VH comprising the amino acid sequence of SEQ ID NO:62 and a VL comprising the amino acid sequence of SEQ ID NO:66.

Preferably, the binding molecule described herein and having target specificity for the EC2 domain of CDH3 comprises:

i. a heavy chain comprising the amino acid sequence of SEQ ID NO:88 and a light chain comprising the amino acid sequence of SEQ ID NO:89;
ii. a heavy chain comprising the amino acid sequence of SEQ ID NO:90 and a light chain comprising the amino acid sequence of SEQ ID NO:91;
iii. a heavy chain comprising the amino acid sequence of SEQ ID NO:92 and a light chain comprising the amino acid sequence of SEQ ID NO:93.

In a specific aspect, the binding molecule targeting TRAILR2 and the EC2 domain of CDH3 comprises a modified heavy chain, preferably wherein a TRAILR2-specific scFv is fused to the C-terminus of an Ig heavy chain. Preferably, said modified heavy chain comprises the amino acid sequence of SEQ ID NO:41, SEQ ID NO:51, or SEQ ID NO:61. Specifically, said binding molecule comprises an amino acid sequence that is at least 80%, at least 90%, at least 95%, at least 98%, or at least 99% identical to SEQ ID NO:41, SEQ ID NO:51, or SEQ ID NO:61.

Specifically, said binding molecule comprises:

i. a modified heavy chain comprising the amino acid sequence of SEQ ID NO:41 and a light chain comprising the amino acid sequence of SEQ ID NO:89;
ii. a modified heavy chain comprising the amino acid sequence of SEQ ID NO:51 and a light chain comprising the amino acid sequence of SEQ ID NO:91; or
iii. a modified heavy chain comprising the amino acid sequence of SEQ ID NO:61 and a light chain comprising the amino acid sequence of SEQ ID NO:93.

Mono-Specific Antibody Molecules of the Invention

Further provided herein are antibody molecules (e.g., a full length antibody/immunoglobulin molecule having a Y shaped structure with two heavy and two light chains, or fragments thereof such as Fv, Fab, Fab', or F(ab')2 fragment, a single chain antibody, single chain variable fragment (scFv)) that bind specifically to CDH3. Specifically, provided herein are antibody molecules that bind specifically to the EC1 or the EC2 domain of CDH3. In some embodiments, the antibody molecules specific for CDH3 are recombinant monoclonal antibodies, chimeric, humanized or human antibody molecules.

In some embodiments the antibody molecule specific for CDH3 comprises any one of the following CDR combinations shown in (i) to (vii):

i. heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3);
ii. heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3);
iii. heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3);
iv. heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3);

v. heavy chain CDRs comprising the amino acid sequences of SEQ ID NO:43 (CDR1), SEQ ID NO:44 (CDR2) and SEQ ID NO:45 (CDR3) and light chain CDRs comprising the amino acid sequences of SEQ ID NO:47 (CDR1), SEQ ID NO:48 (CDR2) and SEQ ID NO:49 (CDR3);

vi. heavy chain CDRs comprising the amino acid sequences of SEQ ID NO:53 (CDR1), SEQ ID NO:54 (CDR2) and SEQ ID NO:55 (CDR3) and light chain CDRs comprising the amino acid sequences of SEQ ID NO:57 (CDR1), SEQ ID NO:58 (CDR2) and SEQ ID NO:59 (CDR3); or vii. heavy chain CDRs comprising the amino acid sequences of SEQ ID NO:63 (CDR1), SEQ ID NO:64 (CDR2) and SEQ ID NO:65 (CDR3) and light chain CDRs comprising the amino acid sequences of SEQ ID NO:67 (CDR1), SEQ ID NO:68 (CDR2) and SEQ ID NO:69 (CDR3).

Specifically, provided herein is an antibody or antigen-binding fragment thereof that binds specifically to CDH3, comprising heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3).

Specifically, provided herein is an antibody or antigen-binding fragment thereof that binds specifically to CDH3, comprising heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3).

Specifically, provided herein is an antibody or antigen-binding fragment thereof that binds specifically to CDH3, comprising heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3).

Specifically, provided herein is an antibody or antigen-binding fragment thereof that binds specifically to CDH3, comprising heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3).

Specifically, provided herein is an antibody or antigen-binding fragment thereof that binds specifically to CDH3, comprising heavy chain CDRs comprising the amino acid sequences of SEQ ID NO:43 (CDR1), SEQ ID NO:44 (CDR2) and SEQ ID NO:45 (CDR3) and light chain CDRs comprising the amino acid sequences of SEQ ID NO:47 (CDR1), SEQ ID NO:48 (CDR2) and SEQ ID NO:49 (CDR3).

Specifically, provided herein is an antibody or antigen-binding fragment thereof that binds specifically to CDH3, comprising heavy chain CDRs comprising the amino acid sequences of SEQ ID NO:53 (CDR1), SEQ ID NO:54 (CDR2) and SEQ ID NO:55 (CDR3) and light chain CDRs comprising the amino acid sequences of SEQ ID NO:57 (CDR1), SEQ ID NO:58 (CDR2) and SEQ ID NO:59 (CDR3).

Specifically, provided herein is an antibody or antigen-binding fragment thereof that binds specifically to CDH3, comprising heavy chain CDRs comprising the amino acid sequences of SEQ ID NO:63 (CDR1), SEQ ID NO:64 (CDR2) and SEQ ID NO:65 (CDR3) and light chain CDRs comprising the amino acid sequences of SEQ ID NO:67 (CDR1), SEQ ID NO:68 (CDR2) and SEQ ID NO:69 (CDR3).

In some embodiments, the antibody molecule specific for CDH3 comprises:

i. a VH comprising the amino acid sequence of SEQ ID NO:2 and a VL comprising the amino acid sequence of SEQ ID NO:6;

ii. a VH comprising the amino acid sequence of SEQ ID NO:12 and a VL comprising the amino acid sequence of SEQ ID NO:16;

iii. a VH comprising the amino acid sequence of SEQ ID NO:22 and a VL comprising the amino acid sequence of SEQ ID NO:26;

iv. a VH comprising the amino acid sequence of SEQ ID NO:32 and a VL comprising the amino acid sequence of SEQ ID NO:36 v. a VH comprising the amino acid sequence of SEQ ID NO:42 and a VL comprising the amino acid sequence of SEQ ID NO:46;

vi. a VH comprising the amino acid sequence of SEQ ID NO:52 and a VL comprising the amino acid sequence of SEQ ID NO:56; or vii. a VH comprising the amino acid sequence of SEQ ID NO:62 and a VL comprising the amino acid sequence of SEQ ID NO:66.

Specifically, provided herein is an antibody or antigen-binding fragment thereof that binds specifically to CDH3, comprising a heavy chain variable domain (VH) comprising the amino acid sequence of SEQ ID NO:2 and a light chain variable domain (VL) comprising the amino acid sequence of SEQ ID NO:6.

Specifically, provided herein is an antibody or antigen-binding fragment thereof that binds specifically to CDH3, comprising a VH comprising the amino acid sequence of SEQ ID NO:12 and a VL comprising the amino acid sequence of SEQ ID NO:16.

Specifically, provided herein is an antibody or antigen-binding fragment thereof that binds specifically to CDH3, comprising a VH comprising the amino acid sequence of SEQ ID NO:22 and a VL comprising the amino acid sequence of SEQ ID NO:26.

Specifically, provided herein is an antibody or antigen-binding fragment thereof that binds specifically to CDH3, comprising a VH comprising the amino acid sequence of SEQ ID NO:32 and a VL comprising the amino acid sequence of SEQ ID NO:36.

Specifically, provided herein is an antibody or antigen-binding fragment thereof that binds specifically to CDH3, comprising a VH comprising the amino acid sequence of SEQ ID NO:42 and a VL comprising the amino acid sequence of SEQ ID NO:46.

Specifically, provided herein is an antibody or antigen-binding fragment thereof that binds specifically to CDH3, comprising a VH comprising the amino acid sequence of SEQ ID NO:52 and a VL comprising the amino acid sequence of SEQ ID NO:56.

Specifically, provided herein is an antibody or antigen-binding fragment thereof that binds specifically to CDH3, comprising a VH comprising the amino acid sequence of SEQ ID NO:62 and a VL comprising the amino acid sequence of SEQ ID NO:66.

In some embodiments, the CDH3-specific antibodies as defined above further comprise human heavy chain constant domains (e.g., an IgG constant domain) and a human light chain constant domain (e.g. a kappa or lambda light chain constant domain).

In specific embodiment of the antibody molecule specific for CDH3 comprises, said antibody molecule comprises:

i. a heavy chain comprising the amino acid sequence of SEQ ID NO:80 and a light chain comprising the amino acid sequence of SEQ ID NO:81;

ii. a heavy chain comprising the amino acid sequence of SEQ ID NO:82 and a light chain comprising the amino acid sequence of SEQ ID NO:83;

iii. a heavy chain comprising the amino acid sequence of SEQ ID NO:84 and a light chain comprising the amino acid sequence of SEQ ID NO:85;

iii. a heavy chain comprising the amino acid sequence of SEQ ID NO:86 and a light chain comprising the amino acid sequence of SEQ ID NO:87;

v. a heavy chain comprising the amino acid sequence of SEQ ID NO:88 and a light chain comprising the amino acid sequence of SEQ ID NO:89;

vi. a heavy chain comprising the amino acid sequence of SEQ ID NO:90 and a light chain comprising the amino acid sequence of SEQ ID NO:91;

vii. a heavy chain comprising the amino acid sequence of SEQ ID NO:92 and a light chain comprising the amino acid sequence of SEQ ID NO:93.

Specifically, provided herein is an antibody or antigen-binding fragment thereof that binds specifically to CDH3, comprising a heavy chain comprising the amino acid sequence of SEQ ID NO:80 and a light chain comprising the amino acid sequence of SEQ ID NO:81.

Specifically, provided herein is an antibody or antigen-binding fragment thereof that binds specifically to CDH3, comprising a heavy chain comprising the amino acid sequence of SEQ ID NO:82 and a light chain comprising the amino acid sequence of SEQ ID NO:83.

Specifically, provided herein is an antibody or antigen-binding fragment thereof that binds specifically to CDH3, comprising a heavy chain comprising the amino acid sequence of SEQ ID NO:84 and a light chain comprising the amino acid sequence of SEQ ID NO:85.

Specifically, provided herein is an antibody or antigen-binding fragment thereof that binds specifically to CDH3, comprising a heavy chain comprising the amino acid sequence of SEQ ID NO:86 and a light chain comprising the amino acid sequence of SEQ ID NO:87.

Specifically, provided herein is an antibody or antigen-binding fragment thereof that binds specifically to CDH3, comprising a heavy chain comprising the amino acid sequence of SEQ ID NO:88 and a light chain comprising the amino acid sequence of SEQ ID NO:89.

Specifically, provided herein is an antibody or antigen-binding fragment thereof that binds specifically to CDH3, comprising a heavy chain comprising the amino acid sequence of SEQ ID NO:90 and a light chain comprising the amino acid sequence of SEQ ID NO:91

Specifically, provided herein is an antibody or antigen-binding fragment thereof that binds specifically to CDH3, comprising a heavy chain comprising the amino acid sequence of SEQ ID NO:92 and a light chain comprising the amino acid sequence of SEQ ID NO:93.

The CDH3-specific antibodies provided herein may be used for in vitro, in vivo or ex vivo labelling, localizing, identifying or targeting cells expressing CDH3 (e.g. in ELISA assays, FACS analysis, immunohistology or the like) by attaching a dye, a drug or another molecule with binding specificity for a different antigen. In some embodiments, CDH3-specific antibodies specifically bind to the surface of a CDH3 expressing cell and are used for localizing and/or identifying such cells. In some embodiments, the CDH3 antibodies provided herein are used for identifying cells expressing CDH3 (e.g. tumor cells). In some embodiments, the CDH3 antibodies provided herein are used for delivering a drug or cytotoxic agent to a target cell (e.g. a tumor cell expressing CDH3) by attaching such drug or cytotoxic agent to said CDH3 antibody, thereby, for example, killing said target cell.

Also provided herein is a method of detecting cadherin-3 (CDH3) in a sample, the method comprising the steps:

(a) contacting the sample with an anti-CDH3 antibody molecule as defined herein above;

(b) permitting formation of antibody-antigen complexes in the sample; and (c) detecting the anti-CDH3 antibody.

Means and methods for detecting antibodies are well known in the art and include for example immunohistochemistry, Immunoblotting and ELISA.

Methods of identifying whether a particular tumor expresses TRAILR2 and/or CDH3, are well known in the art. For example, immunohistochemistry can be used to determine whether tumor tissue expresses TRAILR2 and/or CDH3 (e.g. using the TRAILR2 and/or CDH3 antibody molecules described herein).

Further provided herein is a kit for detecting cadherin-3 (CDH3), wherein the kit comprises an anti-CDH3 antibody molecule as defined herein above, and instructions for use.

Further provided herein is a kit for detecting cadherin-3 (CDH3) and TRAILR2, wherein the kit comprises an anti-CDH3 antibody molecule, preferably as defined herein above, and an anti-TRAILR2 antibody molecule, and instructions for use.

Nucleic Acid Molecules, Expression Vectors and Host Cells of the Invention

The present invention further relates to a nucleic acid molecule encoding the bispecific binding molecules or antibody molecules described herein, or a part thereof. The present invention further encompasses a set of nucleic acid molecules encoding the bispecific binding molecules or antibody molecules described herein.

In accordance with the present invention, said nucleic acid molecule "encodes" the binding molecule of the invention or a part thereof, which means that the nucleic acid molecule is provided in an expressible form, i.e. in a form that ensures that the binding molecule (or the respective part thereof) of the present invention can be expressed therefrom.

In some embodiments the binding molecules of the invention or antibody molecule of the invention comprise antibody heavy chain and/or light chain polypeptides. As can be appreciated by the skilled person, nucleic acid molecules can be readily prepared which encode the heavy chain polypeptides, light chain polypeptides, or heavy chain polypeptides and light chain polypeptides.

The term "a part thereof" reflects the fact that not all elements of the binding molecule of the present invention need to be encoded on a single nucleic acid molecule, as will be appreciated by the skilled person. Instead, two or more nucleic acid molecules can be relied on to individually encode certain parts of the binding molecule of the present invention.

Thus, the present invention also encompasses a set of isolated nucleic acid molecules, wherein the set together encodes all parts of the binding molecule of the present invention such that expression of this set of isolated nucleic acid molecules results in the generation of a complete binding molecule of the present invention. In other words, one or more nucleic acid molecule is provided herein, which encode(s) the individual polypeptide chains of the binding molecule of the present invention, including the heavy chains, light chains, scFvs, as well as combinations thereof, either separately on individual nucleic acid molecules or combined in one nucleic acid molecule.

Preferably, the nucleic acid molecule is a DNA molecule comprising coding sequences. More preferably, said DNA molecule additionally comprises regulatory sequences and, optionally, natural or artificial introns (such as e.g. the β-Globin intron from *Homo sapiens* with embedded miRNA-557 expression cassette). It may have its original codons or may have an optimized codon usage that has been specifically adapted for expression in the intended host cell or host organism. Such nucleic acid molecules of the invention can be readily prepared or obtained by the skilled person relying on methods known per se, such as e.g. by automated DNA synthesis, isolation from a nature source and/or recombinant DNA technology, based on the information on the amino acid sequences for the binding molecule of the invention given herein.

The nucleic acid molecules of the invention include, but are not limited to, the DNA molecules encoding the polypeptide sequences shown in the sequence listing. The present invention furthermore contemplates nucleic acid molecules complementary to the above-defined DNA molecules as well as nucleic acid molecules hybridizing thereto under high stringency binding and washing conditions, as defined in WO 2007/042309. Preferred molecules (from an mRNA perspective) are those that have at least 75% or 80% (preferably at least 85%, more preferably at least 90% and most preferably at least 95%) homology or sequence identity with one of the DNA molecules described herein. By way of example, if the aim is to express the bispecific binding molecule or the antibody molecule of the present invention in eukaryotic cells, the DNA sequences will have to be designed to match codon usage in eukaryotic cells. If it is desired to express the antibodies in *E. coli*, or other prokaryotic systems, these sequences will have to be designed to match codon usage *E. coli*, or the respective prokaryotic system. Variants of DNA molecules of the invention can be constructed in several different ways, as described e.g. in WO 2007/042309.

Preferably, the nucleic acid(s) is/are isolated, the term "isolated" being defined further above.

The present invention further relates to an expression vector comprising the nucleic acid molecule(s) of the invention.

For producing the binding molecules or antibodies of the invention, the DNA molecules encoding the binding molecules or antibody molecules described herein or parts thereof are inserted into an expression vector such that the sequences are operatively linked to transcriptional and translational control sequences.

For manufacturing the binding molecules or antibodies of the invention, the skilled artisan may choose from a great variety of expression systems well known in the art, e.g. those reviewed by Kipriyanov and Le Gall, Curr Opin Drug Discov Devel. 2004 March; 7(2):233-42.

In accordance with the present invention, the vector is an expression vector, i.e. a vector that can provide for expression of the respective polypeptide from the encoding nucleic acid molecule in vitro and/or in vivo (e.g. in a suitable host cell, host organism and/or expression system). Expression vectors include plasmids, retroviruses, cosmids, EBV derived episomes, and the like. The expression vector and expression control sequences are typically selected to be compatible with the host cell. Expression vectors generally comprise at least one nucleic acid molecule of the invention that is operably linked to one or more suitable regulatory element(s), such as promoter(s), enhancer(s), terminator(s), and the like. Specific examples of such regulatory elements and other elements, such as integration factor(s), selection marker(s), signal or leader sequence(s), reporter gene(s), and the like, useful or necessary for expressing polypeptides of the invention, are disclosed e.g. on pp. 131 to 133 of WO2006/040153.

Non-limiting examples for promoter sequences (exemplified for expression in mammalian cells) are promoters and/or enhancers derived from CMV (such as the CMV Promoter/Enhancer of human cytomegalovirus or the CMV Simian Virus 40 (SV40) promoter/enhancer), adenovirus, (e.g., the adenovirus major late promoter (AdMLP)), polyoma and strong mammalian promoters such as native immunoglobulin and actin promoters. Examples for polyadenylation signals are Hamster Growth Hormone or Bovine Growth Hormone polyA, SV40 late or early polyA; alternatively, 3'UTRs of immunoglobulin genes etc. can be used.

The recombinant expression vectors may also carry sequences that regulate replication of the vector in host cells (e.g. origins of replication, such as the ColE1 (pUC) origin of replication) and selectable marker genes (such as e.g. a β-Lactamase gene to confer ampicillin resistance for amplification of the plasmids in *E. coli*). The recombinant expression vector may also encode a signal peptide that facilitates secretion of the resulting polypeptide. The nucleic acid molecule encoding the respective polypeptide chain may be cloned into the vector such that the signal peptide is linked in-frame to the amino terminus of the mature full length nucleic acid molecule chain. The signal peptide may be an immunoglobulin signal peptide or a heterologous peptide from a non-immunoglobulin protein. Alternatively, the DNA sequence encoding the full-length chains of the protein of the invention may already contain a signal peptide sequence.

As indicated above, the coding sequences inserted in the vector can e.g. be synthesized by standard methods, or isolated from natural sources or produced semi-synthetically, i.e. by combining chemical synthesis and recombinant techniques. Ligation of the coding sequences to transcriptional regulatory elements and/or to other amino acid encoding sequences can be carried out using established methods. One approach often employed is, for example, to use vectors that encode a functionally complete human CH (constant heavy) immunoglobulin sequence, with appropriate restriction sites engineered so that any antigen binding site such as a single chain Fab sequence or any heavy/light chain variable domain can be easily inserted and expressed. For the antibody heavy chain, it can be, without limitation, any IgG isotype (IgG1, IgG2, IgG3, IgG4) or other immunoglobulins, including allelic variants.

In those cases where more than one nucleic acid molecule is required to make up the binding molecule of the present invention, these more than one nucleic acid molecules can be inserted into different or into the same expression vector.

In the latter case, they may be under the control of the same regulatory elements, e.g. promoters, enhancers, terminators and the like, or they may each have their own set of regulatory elements. In accordance with the present invention it is particularly preferred that, in those cases where more than one nucleic acid molecule encodes the individual elements of the binding molecule of the present invention, all the individual nucleic acid molecules required to form the binding molecule of the present invention are present on a single expression vector and, preferably, each nucleic acid molecule has its own set of regulatory elements.

Expression vectors comprising these DNA molecules can be introduced into host cells, e.g. bacterial cells or (higher) eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Accordingly, the present invention also relates to a host cell transfected with the expression vector(s) of the invention.

Host cells can be any suitable cells known in the art, including prokaryotic cells such as bacteria, as well as eukaryotic cells, such as yeast cells or mammalian cells. Non-limiting examples of mammalian cells include, without being limiting, human, mice, rat, monkey and rodent cells lines. Specific mammalian cell lines available as host cells for expression are well known in the art and include, inter alia, Chinese hamster ovary (CHO) cells, NS0, SP2/0 cells, HeLa cells, baby hamster kidney (BHK) cells, monkey kidney cells (COS), human carcinoma cells (e.g., Hep G2 and A-549 cells), 3T3 cells or the derivatives/progenies of any such cell line. Appropriate culture mediums and conditions for the above-described host cells are known in the art.

Methods of Manufacture and Preparation

For manufacturing the antibodies of the invention, the skilled artisan may choose from a variety of methods well known in the art.

For production of antibodies comprising two complete heavy and two complete light chains, like those of the IgG1 or IgG4 type, see Norderhaug et al., J Immunol Methods 1997, 204 (1): 77-87; Kipriyanow and Le Gall, Molecular Biotechnology 26: 39-60, 2004; Shukla et al., 2007, J. Chromatography B, 848(1): 28-39.

Fab molecules may be produced by expression of nucleic acids encoding such constructs in host cells, like *E. coli, Pichia pastoris*, or mammalian cell lines (e.g. CHO, or NS0). Processes are known in the art which allow proper folding, association, and disulfide bonding of these chains into functional Fab molecules comprising a Fd fragment and a light chain (Burtet et al., J. Biochem. 2007, 142(6), 665-669; Ning et al., Biochem. Mol. Biol. 2005, 38: 204-299; Quintero-Hernandez et al., Mol. Immunol. 2007, 44: 1307-1315; Willems et al. J. Chromatogr. B. Analyt. Technol. Biomed. Life Sci. 2003; 786:161-176.).

Processes for manufacturing scFv antibodies by recombinant expression of nucleic acids encoding scFv constructs in host cells (like *E. coli, Pichia pastoris*, or mammalian cell lines, e.g. CHO or NS0), yielding functional scFv molecules, are also known (Rippmann et al., Applied and Environmental Microbiology 1998, 64(12): 4862-4869; Yamawaki et al., J. Biosci. Bioeng. 2007, 104(5): 403-407; Sonoda et al., Protein Expr. Purif. 2010, 70(2): 248-253).

Specifically, provided herein is a method of producing the binding molecule or the antibody molecule described herein, said method comprising the steps:

(a) culturing the host cell of the invention under conditions allowing expression of the binding molecule of the invention;
(b) optionally recovering said molecule; and, optionally,
(c) further purifying and/or modifying and/or formulating said binding molecule.

The proteins of the invention are produced by culturing the host cells for a period of time sufficient to allow for expression of the protein by the host cells.

Suitable conditions for culturing a prokaryotic or eukaryotic host are well known to the person skilled in the art. To increase the yield and the solubility of the expression product, the medium can be buffered or supplemented with suitable additives known to enhance or facilitate both. In general, the skilled person is also aware that these conditions may have to be adapted to the needs of the host and the requirements of the molecule to be expressed. In case an inducible promoter controls the nucleic acid molecule(s) of the invention in the vector(s) present in the host cell, expression of the molecule of interest can be induced by addition of an appropriate inducing agent. Suitable expression protocols and strategies are known to the skilled person.

Subsequently, the binding molecules of the present invention are recovered and, where necessary, further purified. Preferably, they are recovered from the culture medium as a secreted molecule. However, they can also be recovered from host cell lysates if, for example, they were expressed without a secretory signal. It will be appreciated that the term "recovering said molecule" refers to the isolation of the binding molecule of the present invention encoded by the nucleic acid molecule(s) of the invention, i.e. the binding molecule that is present in the host cell of the invention due to the transformation or transfection of said host cell with the nucleic acid molecule or the vector of the invention.

An optional step of purifying the binding molecule of the present invention further helps in obtaining a substantially homogenous preparations of the molecule. Means and methods for purifying a molecule of interest are well known and the skilled person can, for example, use standard protein purification methods used for recombinant proteins and host cell proteins and adjust it in a way that is appropriate for the respective molecule. By way of example, state-of-the art purification methods useful for obtaining binding molecules of the present invention include, as a first step, removal of cells and/or particulate cell debris from the culture medium or lysate, followed by purification from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin.

As a final optional step in the process for obtaining a binding molecule of the present invention, the purified protein molecule may be dried, e.g. lyophilized, as described below for therapeutic applications, or otherwise formulated as desired. Furthermore, the resulting binding molecule of the present invention may be subjected to further modifications, for example to remove unwanted post-translational modifications and the like.

Pharmaceutical Compositions and Medical Uses of the Binding Molecule of the Present Invention or of the Pharmaceutical Composition The present invention further relates to a pharmaceutical composition comprising or consisting of one or more binding molecules or antibody molecules described herein. In one embodiment, said binding molecule(s) is/are the only pharmaceutically active agent(s). In an alternative embodiment, said composition comprises, in addition to said binding molecule(s), one or more further pharmaceutically active agents, for example as defined further below.

In accordance with the present invention, the term "pharmaceutical composition" relates to a composition for administration to a patient, preferably a human patient. The pharmaceutical composition of the invention comprises the compounds recited above, alone or in combination. It may, optionally, comprise further molecules capable of altering the characteristics of the compounds of the invention thereby, for example, stabilizing, modulating and/or activating their function. The composition may be in solid, liquid or gaseous form and may be, inter alia, in the form of (a) powder(s), e.g. a lyophilized powder, (a) solution(s), (a) tablet(s) or (an) aerosol(s). Preferably, the composition is a lyophilized powder or a solution.

To be used in therapy, the bispecific binding molecule described herein is formulated into pharmaceutical compositions appropriate to facilitate administration to animals or humans. Thus, the pharmaceutical composition of the present invention preferably also comprises a pharmaceutically acceptable carrier. Compositions comprising such carriers can be formulated by well-known conventional methods. Typically, the pharmaceutical composition comprising the binding molecule of the invention can be formulated by mixing the binding molecule with such pharmaceutically acceptable carriers, as well as (optionally) excipients or stabilizers. By "pharmaceutically acceptable carrier" is meant a non-toxic solid, semisolid or liquid filler, diluent, encapsulating material or formulation auxiliary of any type. Also, other excipients, modifiers or stabilizers are nontoxic at the dosages and concentrations employed. Pharmaceutically acceptable carriers, excipients, modifiers and stabilizers include, without limitation, buffer systems such as phosphate, citrate, acetate and other inorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. Also, organic solvents can be contained in the formulation such as ethanol or isopropanol. The excipients may also have a release-modifying or absorption-modifying function.

Usually, aqueous solutions or suspensions will be preferred. Generally, suitable formulations for therapeutic proteins such as the binding molecules of the invention are buffered protein solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 to 40.0 mg/ml, preferably 10.0 to 30 mg/ml, most preferably 30 mg/ml (i.v. administration) or 100 mg/ml (s.c. administration) and an aqueous buffer such as:

phosphate buffered saline, pH 7.4,
other phosphate buffers, pH 6.2 to 8.2,
acetate buffers, pH 3.2 to 7.5, preferably pH 4.8 to 5.5
histidine buffers, pH 5.0 to 7.0, preferably pH 5.3 to 5.5
succinate buffers, pH 3.2 to 6.6, or
citrate buffers, pH 2.1 to 6.2, and, optionally, salts (e.g. NaCl) and/or stabilizing agents (such as e.g. sucrose, trehalose, lysine) and/or other polyalcohols (such as e.g. mannitol and glycerol) for providing isotonicity of the solution, and optionally detergents, e.g. to prevent aggregation (e.g. 0.02% Tween-20 or Tween-80).

Preferred buffered protein solutions for i.v. administration are solutions including about 10 mg/ml of the binding molecule of the invention dissolved in 10 mM citrate buffer, pH 5.5, 207 mM sucrose, 25 mM lysine HCl and 0.02% polysorbate 20.

Particularly preferred buffered protein solutions for i.v. administration are solutions including about 30 mg/ml of the binding molecule of the invention dissolved in about 20 mM His/His-HCl buffer, pH 5.3 to 5.5, preferably pH 5.3, 220 mM sucrose and 0.02% polysorbate 20, and water for injection (WFI).

Formulations for subcutaneous application may include significantly higher concentrations of the antibody of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person or can easily be conceived starting from the above disclosure.

The pharmaceutical composition of the present invention can be administered to the subject using any suitable mode of administration, including for example parenteral administration by infusion or injection (intravenous, intraarticular, intramuscular, subcutaneous, intrasternal, intraperitoneal, intradermal), as well as transdermal, intranasal, buccal, or oral administration or administration by inhalation. For the administration of a solution or a reconstituted lyophilized powder, parenteral modes of administration are preferred.

Generally, for the treatment, prevention and/or alleviation of the diseases, disorders and conditions mentioned herein and depending on the specific disease, disorder or condition to be treated, the potency of the specific binding molecule of the invention to be used, the specific route of administration and the specific pharmaceutical formulation or composition used, has an impact on the actual dose to be administered. Furthermore, the actual pharmaceutically effective amount or therapeutic dosage will also depend on factors known by those skilled in the art such as age and weight of the patient. In any case, the binding molecule of the invention or the pharmaceutical composition of the invention will be administered at dosages and in a manner which allows a pharmaceutically effective amount to be delivered based upon patient's unique condition. Preferably, binding molecules of the invention or the pharmaceutical composition of the invention will be administered in an amount between 0.005 and 20.0 mg per kilogram of body weight and dose, preferably between 0.05 and 10.0 mg/kg/dose, and more preferably between 0.5 and 5 mg/kg/dose, either continuously (e.g. by infusion) or more preferably as single doses. The administration interval may be, for example, twice a week, weekly, or monthly doses, but can significantly vary, especially, depending on the before-mentioned parameters. Thus, in some cases it may be sufficient to use less than the minimum dose given above, whereas in other cases the upper limit may have to be exceeded. When administering large amounts, it may be advisable to divide them up into a number of smaller doses spread over the day. Preferably, administration is once per week at a dose range from between 0.005 and 20.0 mg per kilogram of body weight and dose, preferably between 0.05 and 10.0 mg/kg/dose, and more preferably between 0.5 and 5 mg/kg/dose.

The efficacy of the binding molecules of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

The binding molecules of the invention or the pharmaceutical composition of the invention may be used on their own or in combination with other pharmacologically active ingredients, such as state-of-the-art or standard-of-care compounds, such as e.g. cytostatic or cytotoxic substances, cell proliferation inhibitors, anti-angiogenic substances, steroids, immune modulators/checkpoint inhibitors, and the like.

Hence a further aspect of the invention provides the binding molecules of the invention or a pharmaceutical composition comprising a binding molecule of the invention, together with one or more further active ingredients, and optionally a pharmaceutically acceptable carrier.

Cytostatic and/or cytotoxic active substances which may be administered as combination partners in accordance with the present invention include, without being restricted thereto, hormones, hormone analogues and antihormones, aromatase inhibitors, LHRH agonists and antagonists, inhibitors of growth factors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF)), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib and trastuzumab; antimetabolites (e.g. antifolates such as methotrexate, raltitrexed, pyrimidine analogues such as 5-fluorouracil (5-FU), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g. anthracyclins); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g. PTK2/FAK inhibitors, MCL-1 inhibitors, c-FLIP inhibitors or KRAS inhibitors, such as KRAS G12c, KRAS G12D or KRAS G13d), protein protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/Bcl-xL inhibitors, ErbB receptor inhibitors, BCRABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals including but not limited to systemic targeted biopharmaceuticals, immunotherapeutic agents such as immune checkpoint inhibitors (e.g. CTLA4, PD1, PD-L1, LAG3, and TIM3 binding molecules/immunoglobulins, such as ipilimumab, nivolumab, pembrolizumab), interferon, interferon alpha, or rituximab; oncolytic viruses; anticancer vaccines and various chemotherapeutic agents such as amifostin, anagrelid, clodronat, filgrastin, leucovorin, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signalling pathway; stromal modulators such as (preferably bispecific) molecules targeting CD137 and FAP; and/or cyclin-dependent kinase 9 inhibitors.

Preferred in accordance with the present invention are treatments with the binding molecules of the invention or the pharmaceutical composition of the invention in combination with a drug selected from below:

(i) anti-VEGF antibodies (bevacizumab and other anti-angiogenic substances) with or without chemotherapy combination (including doxorubicin/cyclophosphamide combination and/or capecitabine/docetaxel combination in neoadjuvant setting; taxane/platinum regimen for first and later line treatment), e.g. in particular in breast cancer patients;

(ii) chemotherapeutics (including 5-fluorouracil (5-FU), irinotecan, oxaliplatin, and TAS-102);

(iii) anti-EGFR antibodies (cetuximab and panitumumab in KRAS wild-type tumors) with or without chemotherapy combination (including irinotecan), anti-VEGF antibody combination (bevacizumab and other anti-angiogenic substances) or regorafenib combination, e.g. for the treatment of CRC patients; and/or (iv) EGFR inhibitors, such as gefitinib, afatinib, nintedanib, lapatinib, erlotinib, asimertinib; and/or (v) ALK inhibitors; and/or (vi) ROS1 inhibitors; and/or (vii) immunotherapeutic agents, including anti-PD-1 and anti-PD-L1 agents and anti LAG3 agents, such as ezabenlimab, pembrolizumab and nivolumab and other antibodies as disclosed in WO2017/198741; and/or (viii) stromal modulators such as (preferably bispecific) molecules targeting CD137 and FAP.

In particularly preferred embodiments, the binding molecule of the invention or the pharmaceutical composition of the invention is used for the treatment of cancer in combination with an immune checkpoint inhibitor, preferably with a PD-1 antagonist, such as an anti-PD-1 antibody or an anti-PDL-1 antibody. Preferably said anti-PD-1 antibody is selected from the group consisting of pembrolizumab, nivolumab, pidilizumab, or PD1-1, PD1-2, PD1-3, PD1-4, and PD1-5 as described in WO2017/198741 (incorporated herein by reference), more preferably said anti-PD-1 antibody is ezabenlimab. Preferably said anti-PDL-1 antibody is selected from the group consisting of atezolizumab, avelumab and durvalumab. Specifically, such therapy may be in combination with a chemotherapeutic agent, such as e.g. cisplatin, carboplatin or gemcitabine.

In further preferred embodiments, the binding molecule or the pharmaceutical composition described herein is used for the treatment of cancer in combination with a single chemotherapeutic agent such as cisplatin, carboplatin, paclitaxel, docetaxel, 5-FU, methotrexate, cetuximab, capecitabine, afatinib, irinotecan, oxaliplatin, gemcitabine, paclitaxel, docetaxel, capecitabine, pemetrexed or cetuximab.

In particularly preferred embodiments, the binding molecule or the pharmaceutical composition described herein is used for the treatment of cancer in combination with a combination regimen selected from the group consisting of:

- cetuximab, platinum (cisplatin or carboplatin) and 5-FU;
- cisplatin and cetuximab;
- cisplatin or carboplatin combined with docetaxel or paclitaxel;
- cisplatin and 5-FU;
- cisplatin or carboplatin combined with docetaxel and cetuximab;
- cisplatin or carboplatin combined with paclitaxel and cetuximab;
- pembrolizumab, platinum (cisplatin or carboplatin) and paclitaxel;
- pembrolizumab, platinum (cisplatin or carboplatin) and docetaxel;
- cisplatin and etoposide;
- carboplatin and etoposide; and
- cyclophosphamide in combination with doxorubicin and vincristine.

In a preferred embodiment, the cancer to be treated with the binding molecule described herein is gastric cancer or esophageal adenocarcinoma and the method of treatment comprises a combination of the binding molecule described herein and a chemotherapeutic agent selected from the group consisting of irinotecan, oxaliplatin, paclitaxel and capecitabine.

In a further preferred embodiment, the cancer to be treated with the binding molecule described herein is pancreatic ductal adenocarcinoma (PDAC) and the method of treatment comprises a combination of the binding molecule described herein and a chemotherapeutic agent selected from the group consisting of irinotecan, gemcitabine, paclitaxel and capecitabine.

In a further preferred embodiment, the cancer to be treated with the binding molecule described herein is lung adenocarcinoma and the method of treatment comprises a combination of the binding molecule described herein and a chemotherapeutic agent selected from the group consisting of oxaliplatin, docetaxel and pemetrexed. Preferably, lung adenocarcinoma is treated with a combination therapy comprising the binding molecule of the invention, oxaliplatin and cisplatin.

In a further preferred embodiment, the cancer to be treated with the binding molecule described herein is squamous cell carcinoma of the lung (Lung SCC) and the method of treatment comprises a combination of the binding molecule described herein and a chemotherapeutic agent selected from the group consisting of oxaliplatin, cisplatin and docetaxel. Preferably, lung SCC is treated with a combination therapy comprising the binding molecule of the invention, oxaliplatin and cisplatin.

In yet a further preferred embodiment, the cancer to be treated with the binding molecule described herein is squamous cell carcinoma of head and neck (SCCHN or HNSCC) and the method of treatment comprises a combination of the binding molecule described herein and a chemotherapeutic agent selected from the group consisting of oxaliplatin, paclitaxel, docetaxel and cetuximab.

In a further embodiment, the binding molecule or the pharmaceutical composition described herein is used for the treatment of cancer in combination with radiotherapy.

The present invention further relates to the binding molecule of the invention, or the pharmaceutical composition of the invention, for use in medicine. The present invention further relates to the binding molecule of the invention, or the pharmaceutical composition of the invention, for use in the preparation of a medicament.

Furthermore, the present invention also relates to the binding molecule of the invention, or the pharmaceutical composition of the invention, for use in a method of treating, ameliorating or preventing cancer. The present invention further relates to a method of treating, preventing or ameliorating cancer comprising administering a therapeutically effective amount of the binding molecule of the invention, or of the pharmaceutical composition of the invention, to a patient in need thereof.

The "therapeutically effective amount" of the molecule to be administered is the minimum amount necessary to prevent, ameliorate, or treat clinical symptoms of cancer, in particular the minimum amount which is effective to the specific cancer to be treated.

As used herein, the term "cancer" is meant to include all types of cancerous growths or oncogenic processes, metastatic tissues or malignantly transformed cells, tissues, or organs, irrespective of histopathologic type or stage of invasiveness. Thus, all cancers, tumors, neoplasms, etc., mentioned below which are characterized by their specific location/origin in the body are meant to be included both as the primary tumors and the metastatic tumors derived therefrom.

Cancers, tumors, and other proliferative diseases whose growth can be inhibited using the multi-specific binding molecules described herein are any TRAILR2/CDH3 expressing tumors including but not limited to head and neck cancer, preferably HNSCC; lung cancer; preferably NSCLC; pancreatic cancer; cervical cancer; ovarian cancer; endometrial cancer; breast cancer, preferably TNBC; liver cancer (hepatoblastoma or hepatocellular carcinoma); prostate cancer; gastric sarcoma; gastrointestinal stromal tumors, oesophageal cancer; colon cancer; colorectal cancer; renal cancer; skin cancer; or gastro-intestinal cancers. Gastrointestinal cancers include but are not limited to oesophageal cancer (e.g., gastroesophageal junction cancer), stomach (gastric) cancer, hepatocellular carcinoma, biliary tract cancer (e.g., cholangiocarcinoma), gallbladder cancer, pancreatic cancer or colorectal cancer (CRC).

In a preferred embodiment of the binding molecule or the pharmaceutical composition for use according to the invention, or the method of treating, preventing or ameliorating cancer of the invention, or the use of the invention, the cancer is lung cancer, specifically lung adenocarcinoma, squamous cell carcinoma of the lung (lung SCC) and Non-Small Cell Lung Cancer (NSCLC); head and neck cancer, specifically head and neck squamous cell carcinoma (HNSCC); pancreatic cancer, specifically pancreatic ductal adenocarcinoma (PDAC); breast cancer, specifically triple negative breast cancer (TNBC); gastric cancer (GC); ovarian cancer; endometrial cancer, or esophageal cancer.

In a particularly preferred embodiment of the invention the cancer is pancreatic cancer, Non-Small Cell Lung Cancer (NSCLC), or Head and Neck Squamous Cell Carcinoma (HNSCC).

Pancreatic cancer (PAC) is a malignant disease causing >400.000 deaths per year worldwide. It is among the most-common causes of cancer-related death in industrialized countries. Despite therapeutic interventions like surgery and chemotherapy, pancreatic adenocarcinoma, accounting for ~90% of all pancreatic cancer cases, typically has a very poor prognosis, with approx. 25% of people surviving one year and only 5% of patients surviving for five years. Pancreatic ductal adenocarcinoma (PDAC) is the most prevalent neoplastic disease of the pancreas accounting for more than 90% of all pancreatic malignancies Lung cancer is the leading cause of cancer-related mortality in the United States. The 5-year relative survival rate from 2011 to 2017 for patients with lung cancer was 22%. NSCLC is any type of epithelial lung cancer other than small cell lung cancer (SCLC). The most common types of NSCLC are squamous cell carcinoma, large cell carcinoma, and adenocarcinoma, but there are several other types that occur less frequently. As a class, NSCLC is usually less sensitive to chemotherapy and radiation therapy compared with SCLC. Patients with resectable disease may be cured by surgery or surgery followed by chemotherapy. However, a large number of patients have unresectable disease and local control may be achieved with radiation therapy, but cure is seen only in a small number of patients. Hence there is a great need for further therapeutic agents to treat this disease.

Most head and neck cancers are derived from the mucosal epithelium in the oral cavity, pharynx and larynx and are known collectively as head and neck squamous cell carcinoma (HNSCC). Oral cavity and larynx cancers are generally associated with tobacco consumption, alcohol abuse or both, whereas pharynx cancers are increasingly attributed to infection with human papillomavirus (HPV), primarily HPV-16. Head and neck cancers can also begin in the salivary glands, sinuses, or muscles or nerves in the head and neck, but these types of cancer are much less common than squamous cell carcinomas.

HNSCC of the oral cavity is generally treated with surgical resection, followed by adjuvant radiation or chemotherapy plus radiation (known as chemoradiation or chemoradiotherapy (CRT)) depending on the disease stage. With the exception of early-stage oral cavity cancers (which are treated with surgery alone), treatment of the majority of patients with HNSCC is complicated and requires multimodality approaches and thus multidisciplinary care. Targeted therapeutic agents to treat HNSCC patients, and in particular late-stage patients, are thus urgently needed.

Colorectal cancer (CRC) is a distinct malignant disease listed in ICD-10 and one of the leading causes of cancer morbidity and mortality worldwide. Approximately 25% of CRC patients present with overt metastasis and metastatic disease develops in 40-50% of newly diagnosed patients. Although recent improvements in chemotherapy have extended survival durations of metastatic CRC, most patients will succumb to their disease. Hence there is a great need for further therapeutic agents to treat this disease.

Approximately 30-50% of colorectal cancers are known to have a mutated (abnormal) KRAS gene. KRAS mutations frequently found in neoplasms include those at exon 2 (codons 12 and 13) and exon 3 (codon 61) and can be analysed from tumor biopsies. They include activating mutations that result in continual signal transduction, stimulating downstream signalling pathways involved in cell growth, proliferation, invasion, and metastasis. Thus, in one embodiment, the binding molecules of the present invention are for use in the treatment of a KRAS mutant colorectal cancer (i.e., patients with KRAS mutant tumors). In an alternative embodiment, the binding molecules of the present invention are for use in the treatment of a KRAS wild type colorectal cancer (i.e., patients with KRAS wildtype tumors).

Esophageal cancer is among the most frequently diagnosed cancer worldwide. Similar to pancreatic cancer, diagnosis is difficult and tends to happen in already advanced stages, leading to a very poor prognosis for this indication. As a consequence, it accounts for approximately 5% of cancer-related deaths, thus making it the sixth most common cancer-related death cause.

With approximately 2.3 million new cases worldwide (GLOBOSCAN 2020), breast cancer is the most frequently diagnosed malignancy among women. Triple-negative breast cancer (TNBC) constitutes 15-20% of breast cancers and occurs more frequently in women younger than 40 years. Due to the highly invasive nature, TNBC is accompanied by distant metastasis in almost 50% of patients. TNBC patients show a shorter survival time compared to other types of breast cancer, with a 5-year mortality rate of approximately 40% and a mortality rate after disease recurrence of up to 75%. Currently used endocrine or molecular targeted therapies in other subtypes of BC do not represent an option for TNBC due to its molecular phenotype. Since the efficacy of chemotherapy based systemic TNBC treatments, such as postoperative adjuvant chemoradiotherapy, is very poor, there is a high need to develop new therapeutic modalities for this disease.

Ovarian cancer represents the seventh most common type of cancer in women worldwide and it has the highest morbidity among malignancies in women. Of the epithelial carcinoma types, the serous ovarian carcinoma is the most prevalent one. Ovarian cancer is diagnosed at a late stage in approximately 80% of cases and therefore has a usually poor prognosis.

Especially for recurrent ovarian cancer, current treatments are characterized my high intensity, poor quality-of-life, and low chance for cure. Therefore, new therapeutic strategies are urgently needed for treatment of this disease.

A stated above the inventors have identified that the binding molecules described herein have much utility for targeting cancer cells and therefore can be used in the therapy of cancers which express both TRAILR2 and CDH3. Methods of identifying whether a particular tumor expresses TRAILR2 and CDH3 are well known in the art. For example, immunohistochemistry can be used to determine whether tumor tissue expresses TRAILR2 and CDH3 (e.g. using the TRAILR2 and/or CDH3 antibody molecules described herein) and hence would be suitable for treatment with the binding molecule of the invention.

The binding molecules of the invention may be used in therapeutic regimens in the context of first line, second line, or any further line treatments and maintenance treatment.

In a further aspect, a binding molecule of the invention is used in combination with a device useful for the administration of the binding molecule, such as a syringe, injector pen, micropump, or another device. In a further aspect, a binding molecule of the invention is comprised in a kit of parts, for example also including a package insert with instructions for the use of the binding molecule.

The present invention further comprises the following items:

1. A binding molecule comprising (a) at least one antigen binding site that binds specifically to TNF-related apoptosis-inducing ligand receptor 2 (TRAILR2), and (b) at least one antigen binding site that binds specifically to cadherin-3 (CDH3), wherein said at least one antigen binding site binding specifically to CDH3 is selected from the group consisting of:

i. an antigen binding site comprising heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3);

ii. an antigen binding site comprising heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3);

iii. an antigen binding site comprising heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3); and iv. an antigen binding site comprising heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3).

2. The binding molecule of item 1, wherein the at least one antigen binding site that binds specifically to TRAILR2 comprises heavy chain CDRs comprising the amino acid sequences of SEQ ID NO:73 (CDR1), SEQ ID NO:74 (CDR2) and SEQ ID NO:75 (CDR3) and light chain CDRs comprising the amino acid sequences of SEQ ID NO:77 (CDR1), SEQ ID NO:78 (CDR2) and SEQ ID NO:79 (CDR3).

3. The binding molecule of item 1 or 2, wherein the at least one antigen binding site that binds specifically to CDH3 is an immunoglobulin (Ig) molecule and the at least one antigen binding site that binds specifically to TRAILR2 comprises one or more scFv(s).

4. The binding molecule of item 3, wherein the one or more scFv(s) have a VL-VH orientation from N- to C-terminus.

5. The binding molecule of item 3 or 4, wherein the one or more scFv(s) are fused to the C-terminus of the Ig molecule, preferably wherein a first scFv is fused to a first heavy chain and a second scFv is fused the second heavy chain of the Ig molecule, respectively.

6. The binding molecule of any one of items 3 to 5, wherein the one or more scFv(s) are each fused to the Ig molecule by a peptide linker, preferably a peptide linker having a length of about 4 to 20 amino acids.

7. The binding molecule of any one of items 3 to 6, wherein the Ig molecule is IgG.

8. The binding molecule of any one of items 1 to 7, wherein the antigen binding site that binds specifically to CDH3 is selected from the group consisting of:

i. a heavy chain variable domain (VH) comprising the amino acid sequence of SEQ ID NO:2 and a light chain variable domain (VL) comprising the amino acid sequence of SEQ ID NO:6;

ii. a VH comprising the amino acid sequence of SEQ ID NO:12 and a VL comprising the amino acid sequence of SEQ ID NO:16;

iii. a VH comprising the amino acid sequence of SEQ ID NO:22 and a VL comprising the amino acid sequence of SEQ ID NO:26; and iv. a VH comprising the amino acid sequence of SEQ ID NO:32 and a VL comprising the amino acid sequence of SEQ ID NO:36.

9. The binding molecule of any one of items 1 to 8, comprising:

i. a heavy chain comprising the amino acid sequence of SEQ ID NO:80 and a light chain comprising the amino acid sequence of SEQ ID NO:81;

ii. a heavy chain comprising the amino acid sequence of SEQ ID NO:82 and a light chain comprising the amino acid sequence of SEQ ID NO:83;

iii. a heavy chain comprising the amino acid sequence of SEQ ID NO:84 and a light chain comprising the amino acid sequence of SEQ ID NO:85; or iv. a heavy chain comprising the amino acid sequence of SEQ ID NO:86 and a light chain comprising the amino acid sequence of SEQ ID NO:87.

10. The binding molecule of any one of items 1 to 9, wherein the at least one antigen binding site that binds specifically to TRAILR2 is an antigen binding site comprising a heavy chain variable domain (VH) comprising the amino acid sequence of SEQ ID NO:72 and a light chain variable domain (VL) comprising the amino acid sequence of SEQ ID NO:76.

11. The binding molecule of item 10, comprising i. a modified heavy chain comprising the amino acid sequence of SEQ ID NO:1 and a light chain comprising the amino acid sequence of SEQ ID NO:81;

ii. a modified heavy chain comprising the amino acid sequence of SEQ ID NO:11 and a light chain comprising the amino acid sequence of SEQ ID NO:83;

iii. a modified heavy chain comprising the amino acid sequence of SEQ ID NO:21 and a light chain comprising the amino acid sequence of SEQ ID NO:85; or iv. a modified heavy chain comprising the amino acid sequence of SEQ ID NO:31 and a light chain comprising the amino acid sequence of SEQ ID NO:87.

12. An antibody or antigen-binding fragment thereof binding specifically to CDH3, comprising:

i. heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3);

ii. heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3);

iii. heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3);

iv. heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3)

v. heavy chain CDRs comprising the amino acid sequences of SEQ ID NO:43 (CDR1), SEQ ID NO:44 (CDR2) and SEQ ID NO:45 (CDR3) and light chain CDRs comprising the amino acid sequences of SEQ ID NO:47 (CDR1), SEQ ID NO:48 (CDR2) and SEQ ID NO:49 (CDR3);

vi. heavy chain CDRs comprising the amino acid sequences of SEQ ID NO:53 (CDR1), SEQ ID NO:54 (CDR2) and SEQ ID NO:55 (CDR3) and light chain CDRs comprising the amino acid sequences of SEQ ID NO:57 (CDR1), SEQ ID NO:58 (CDR2) and SEQ ID NO:59 (CDR3); or vii. heavy chain CDRs comprising the amino acid sequences of SEQ ID NO:63 (CDR1), SEQ ID NO:64 (CDR2) and SEQ ID NO:65 (CDR3) and light chain CDRs comprising the amino acid sequences of SEQ ID NO:67 (CDR1), SEQ ID NO:68 (CDR2) and SEQ ID NO:69 (CDR3).

13. The antibody or antigen-binding fragment thereof of item 12, comprising:

i. a heavy chain variable domain (VH) comprising the amino acid sequence of SEQ ID NO:2 and a light chain variable domain (VL) comprising the amino acid sequence of SEQ ID NO:6;

ii. a VH comprising the amino acid sequence of SEQ ID NO:12 and a VL comprising the amino acid sequence of SEQ ID NO:16;

iii. a VH comprising the amino acid sequence of SEQ ID NO:22 and a VL comprising the amino acid sequence of SEQ ID NO:26;

iv. a VH comprising the amino acid sequence of SEQ ID NO:32 and a VL comprising the amino acid sequence of SEQ ID NO:36 v. a VH comprising the amino acid sequence of SEQ ID NO:42 and a VL comprising the amino acid sequence of SEQ ID NO:46;

vi. a VH comprising the amino acid sequence of SEQ ID NO:52 and a VL comprising the amino acid sequence of SEQ ID NO:56; or vii. a VH comprising the amino acid sequence of SEQ ID NO:62 and a VL comprising the amino acid sequence of SEQ ID NO:66.

14. The antibody or antigen-binding fragment thereof of item 12 or 13, comprising:

i. a heavy chain comprising the amino acid sequence of SEQ ID NO:80 and a light chain comprising the amino acid sequence of SEQ ID NO:81;

ii. a heavy chain comprising the amino acid sequence of SEQ ID NO:82 and a light chain comprising the amino acid sequence of SEQ ID NO:83;

iii. a heavy chain comprising the amino acid sequence of SEQ ID NO:84 and a light chain comprising the amino acid sequence of SEQ ID NO:85;

iv. a heavy chain comprising the amino acid sequence of SEQ ID NO:86 and a light chain comprising the amino acid sequence of SEQ ID NO:87 v. a heavy chain comprising the amino acid sequence of SEQ ID NO:88 and a light chain comprising the amino acid sequence of SEQ ID NO:89;

vi. a heavy chain comprising the amino acid sequence of SEQ ID NO:90 and a light chain comprising the amino acid sequence of SEQ ID NO:91; or vii. a heavy chain comprising the amino acid sequence of SEQ ID NO:92 and a light chain comprising the amino acid sequence of SEQ ID NO:93.

15. The antibody or antigen-binding fragment thereof of any one of items 12 to 14, which is selected from the group consisting of chimeric, humanized, and human antibodies or antibody fragments, and scFvs, Fab fragments, monovalent antibody fragments and $F(ab')^2$ fragments.

16. An isolated nucleic acid encoding the binding molecule of any one of items 1 to 11 or the antibody or antigen-binding fragment thereof of any one of items 12 to 15.

17. An expression vector comprising the nucleic acid of item 16.

18. The vector of item 17, wherein said vector is a plasmid.

19. The vector of item 17, wherein said vector is a viral vector.

20. A host cell comprising the expression vector of any one of items 17 to 19.

21. A method of manufacturing the binding molecule of any one of items 1 to 11 or the antibody or antigen-binding fragment thereof of any one of items 12 to 15 comprising i. cultivating the host cell of item 20 under conditions allowing expression of the molecule, and ii. recovering the molecule, and optionally iii. further purifying and/or modifying and/or formulating the molecule.

22. The binding molecule of any one of items of 1 to 11, for use in medicine.

23. The binding molecule of any one of items 1 to 11, for use in the treatment of cancer.

24. The binding molecule for use according to item 23, wherein the cancer is pancreatic cancer, lung cancer or head and neck cancer.

25. A pharmaceutical composition comprising the binding molecule of any one of items 1 to 11 and a pharmaceutically acceptable carrier.

26. The pharmaceutical composition in accordance with item 25, which is lyophilized, stabilized and/or formulated for administration by injection.

27. A bispecific binding molecule comprising at least one antigen binding site that binds specifically to TNF-related apoptosis-inducing ligand receptor 2 (TRAILR2) and at least one antigen binding site that binds specifically to the EC1 domain of cadherin-3 (CDH3).

Features and advantages of the present invention will become apparent from the following more detailed Examples which illustrate, by way of example, the principles of the invention.

EXAMPLES

Example 1: Prevalence of Both CDH3 and TRAILR2 in Selected Tumor Indications Immunohistochemistry (IHC) for TRAILR2 and CDH3 was performed as follows:

Two-μm thick sections of each FFPE-block were prepared on a microtome, put on glass slides and dewaxed. The CDH3 sections were stained with the primary antibody Abcam #ab242060, rabbit monoclonal (1:50 in diluent with casein, Roche #760-219) on the automated platform Ventana Discovery Ultra using program #183. DR5 IHC was done using the Ventana Discovery program nr. 148 with the following antibody: rabbit anti DR5 (cell signalling #69400S Lot:1; 1:50 in Discovery Antibody diluent (Roche #760-108). Following the automated staining run, the slides were washed in distilled water in a mild detergent, then thoroughly rinsed in distilled water, put in a 90% ethanol bath for 1 minute, then moved to three baths of 100% ethanol for 1 minute, then moved to two baths of xylene for 30 seconds, and finally coverslipped with mounting medium. The slides were scanned (3D Histech) and submitted for analysis.

CDH3 expression was tested by IHC in non-neoplastic tissue (n=40) including liver and no CDH3 expression was found (data not shown). Co-expression of TRAILR2 and CDH3 on mRNA levels was detected in several indications such as pancreatic cancer (PAC), head and neck cancer, lung cancer, colorectal cancer, oesophageal cancer, triple negative breast cancer, and in bladder urothelial, ovarian, endometrial, and cervical cancer (TCGA), as shown below for some of these indications in table 2.

TABLE 2

Prevalence of CDH3 and TRAILR2 expression in different indications (TCGA data)

| TCGA database | | | | | | | |
|---|---|---|---|---|---|---|---|
| | Informative | Number of cases (TPM ≥30) | | | Proportion (%) (TPM ≥30) | | |
| Indication | cases (n) | TRAILR2 | CDH3 | TR2/CDH3 | TRAILR2 | CDH3 | TR2/CDH3 |
| HNSCC | 504 | 396 | 496 | 391 | 78.57 | 98.41 | 77.58 |
| Pancreatic adenocarcinoma | 179 | 156 | 118 | 115 | 87.15 | 65.92 | 64.25 |
| Lung squamous cell carcinoma | 500 | 371 | 452 | 349 | 74.20 | 90.40 | 69.80 |
| Lung adenocarcinoma | 506 | 441 | 307 | 283 | 87.15 | 60.67 | 55.93 |
| Ovarian carcinoma | 381 | 74 | 194 | 50 | 19.42 | 50.92 | 13.12 |
| Endometrial carcinoma | 542 | 382 | 389 | 290 | 70.48 | 71.77 | 53.51 |
| Triple negative breast cancer | 177 | 82 | 141 | 70 | 46.33 | 79.66 | 39.55 |
| Colorectal cancer | 612 | 545 | 484 | 437 | 89.05 | 79.85 | 71.41 |

Total number of informative cases and the number and proportion (in %) of cases showing the characteristic of interest (mRNA expression, TPM ≥30) are indicated for each cancer type. TPM: transcripts per million reads, TR2/CDH3: TRAILR2 and CDH3 double-positive cases, TCGA: The Cancer Genome Atlas. HNSCC: head and neck squamous cell carcinoma.

For example, FIGS. 2A and B shows protein expression and membrane localisation in correlation with mRNA expression for TRAILR2 and CDH3 in colorectal carcinoma.

FIG. 2C shows representative IHC images for CDH3 and TRAILR2 in tissue sections of squamous cell carcinoma of head and neck and squamous cell carcinoma of the oesophagus.

Example 2: Design and Generation of Binding Molecules Recognizing Human Cadherin3 (CDH3) and Human TRAIL Receptor 2 (TRAILR2)

In the present study binding molecules that bind CDH3 and TRAILR2 and that induce apoptosis in cancer cells expressing both CDH3 and TRAILR2 were developed. The molecular design comprises an IgG antibody which has specificity for CDH3 and scFvs with specificity to TRAILR2 coupled to the C terminus of the heavy chain. The bispecific molecule contains flexible peptide sequences between the variable heavy (VH) and variable light (VL) domains of the scFv, and the scFv domains are linked to the IgG antibody via further series of linkers.

Figure 3:
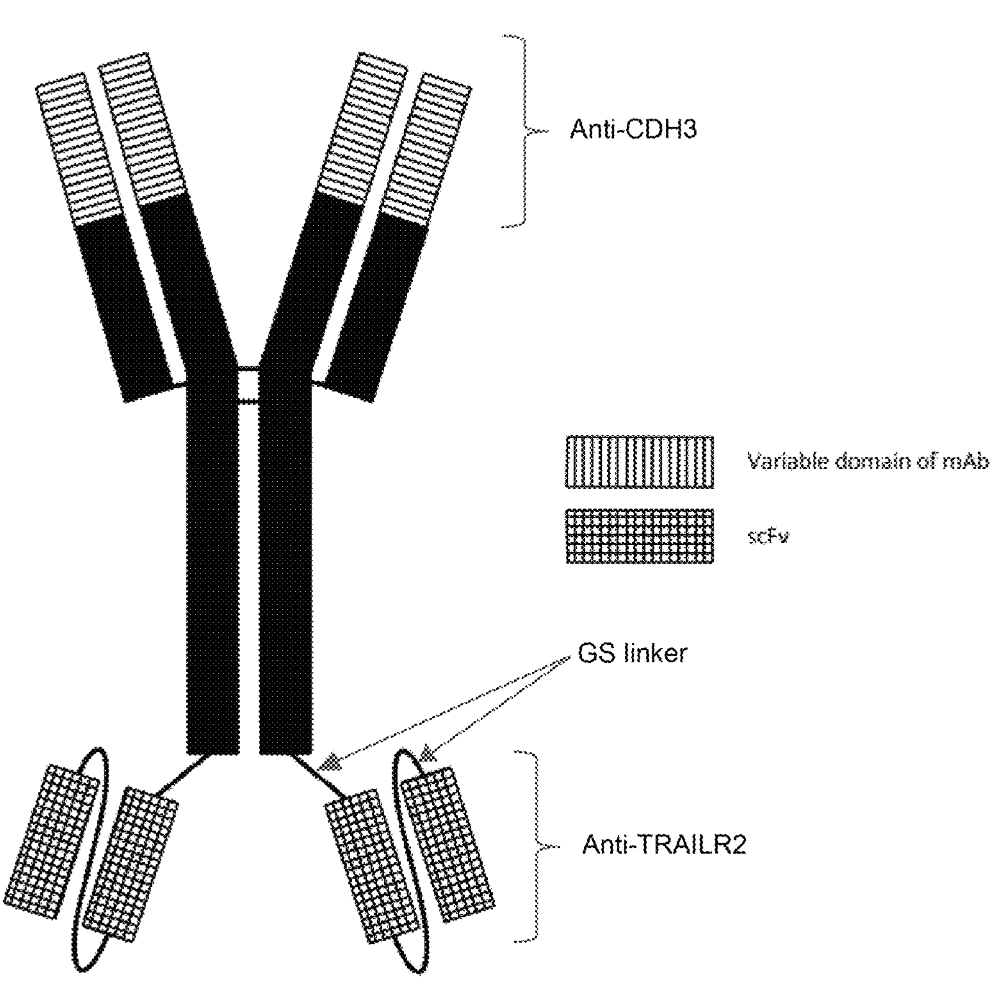
FIG. 3: Schematic representation of the molecule design. An example for a binding molecule of the invention is depicted comprising (i) an Ig molecule that specifically binds to CDH3, which comprises two heavy and two light chains, and (ii) two scFv molecules that specifically binds to TRAILR2. The N-terminus of an scFv is fused to the C-terminus of each of the heavy chains of the Ig molecule, thereby forming a symmetric, bispecific and tetravalent antibody-like molecule.

The binding molecules are bispecific and tetravalent. A schematic of the design is shown in FIG. 3. An example for a binding molecule of the invention is depicted comprising (i) an Ig molecule that specifically binds to CDH3, which comprises two heavy and two light chains, and (ii) two scFv molecules that specifically bind to TRAILR2. The N-terminus of an scFv is fused to the C-terminus of each of heavy chains of the Ig molecule, thereby forming a symmetric, bispecific and tetravalent antibody-like molecule.

The following examples explain the methods used to generate bispecific molecules that bind CDH3 and TRAILR2 and the biological activity of these molecules.

2.1 Preparation of Binding Domains that Recognise CDH3 and TRAILR2 Using High Throughput V Gene Recovery from Hybridomas and Cultured Single B Cells In order to prepare bispecific molecules binding to human CDH3 and TRAILR2, it is necessary to obtain variable domains binding to the individual target antigens (anti-CDH3 and anti-TRAILR2). To achieve this, clonal hybridomas or single B cells derived from CDH3 or TRAILR2 immunized AlivaMab humanized mice (Ablexis, San Francisco, Calif., USA: AlivaMab transgenic mouse platform with human immunoglobulin loci) were cultured in vitro. Supernatants were screened for reactivity against recombinant human CDH3 or TRAILR2, by AlphaLISA (PerkinElmer, Waltham, Mass., USA), and against binding to GP2d cells, by Flow-Cytometry.

Immunoglobulin (Ig) VH and VL genes were then amplified from identified positive clones. To isolate RNA from hybridomas, about $2 \times 10^6$ cells from single clones were pelleted and used as source material. For single B cells, 100 to 500 cells expanded from singularly isolated B cells were used as source material. RNA was isolated using RNeasy Plus (Qiagen, Hilden, Germany). cDNA was then synthesized using Smarter cDNA synthesis kit (Clontech, Mount View, CA) according to manufacturer's instructions.

To facilitate cDNA synthesis, oligodT was used to prime reverse transcription of all messenger RNAs followed by "5' capping" with a Smarter IIA oligonucleotide. Subsequent amplification of the VH and VL fragments was performed using a 2-step PCR amplification using 5' primers targeting the Smarter IIA cap and 3' primers targeting consensus regions in CH1. Briefly, each 50 µl PCR reaction consists of 20 µM of forward and reverse primer mixes, 25 µl of PrimeStar Max DNA polymerase premix (Clontech), 2 µl of unpurified cDNA, and 21 µl of double-distilled H2O. The cycling program starts at 94° C. for 3 min, followed by 35 cycles (94° C. for 30 Sec, 50° C. for 1 min, 68° C. for 1 min), and ends at 72° C. for 7 min The second round PCR was performed with VL and VH 2nd round primers containing 15 bp complementary extensions that "overlap" respective regions in their respective pTT5 mother vector (VH and VL). Second round PCR was performed with the following program: 94° C. for 3 min; 35 cycles (94° C. for 30 Sec, 50° C. for 1 min, 68° C. for 1 min), and ends at 72° C. for 7 min.

In-Fusion® HD Cloning Kit (Clontech, U.S.A.) was used for directional cloning of VL gene into a pTT5 hulgK vector and VH gene into a pTT5 huIgG1KO vector. To facilitate In-Fusion® HD Cloning, PCR products were purified and treated with Cloning Enhancer before In-Fusion HD Cloning. Cloning and transformation were performed according to manufacturer's protocol (Clontech, U.S.A.). Mini-prep DNAs were subjected to Sanger sequencing to confirm that complete V-gene fragments were obtained.

Using this methodology, a large number of pairs of Ig VH and VL genes encoding binding domains with specificity for CDH3 were prepared.

2.2 Confirmatory Screening of Recombinant Antibodies

Recombinant antibodies were produced by transient transfection of CHO-E37 cells with the corresponding heavy and light chain-encoding plasmids. Supernatants containing expressed recombinant antibodies were assayed by flow cytometry for binding to cell lines expressing human or cyno CDH3. Briefly, cells were incubated with recombinant supernatants, washed, and bound mAbs from the supernatants were detected with anti-human-IgG-APC (Jackson ImmunoResearch 109-136-098). Signal-to-background ratios (S/B) were calculated by dividing the median fluorescence intensity (MFI) of the sample by that of isotype control (variable regions against an unrelated protein and different constant region backbones). Clones of interest were selected for multispecific formatting. Multispecific binding proteins were generated and further evaluated in mechanistic and functional screening (such as cell binding, cytotoxicity and Caspase activation assays).

2.3 Construction of Bispecific Molecules Binding CDH3 and TRAILR2

To construct the gene segment encoding the TRAILR2 scFv, pairs of VL and VH genes encoding TRAILR2-binding variable domains (SEQ ID NO:76 and SEQ ID NO:72, respectively) were joined by a gene segment encoding a flexible linker of peptide sequence GGGGSGGGGSGGGGSGGGGS (SEQ ID NO:232). The resulting scFv-encoding gene segments were in turn cloned in-frame to the 3' end of a gene encoding the heavy chain of a human IgG antibody. These coding segments were synthesized by overlapping PCR methods and cloned into the expression vector pTT5. The pairs of VL and VH genes encoding CDH3-binding variable domains prepared in Example 2.1 were then formatted into the bispecific format illustrated in FIG. 3. The VH genes were cloned into pTT5 expression vector as an in-frame fusion at the 5' end of a gene encoding human Igγ. A gene encoding a TRAILR2-binding scFv was cloned in frame at the 3' end of the same Igγ encoding segment. Similarly, the VL genes were cloned into pTT5 expression vector as an in-frame fusion with a gene encoding human IgG kappa light chain.

The pairs of VL and VH genes encoding CDH3-binding variable domains prepared in Example 2.1 were further used to prepare antibody molecules (full length antibody molecules comprising two light and two heavy chains) that specifically bind to CDH3 (and termed CDH3v1, CDH3v2, CDH3v3, CDH3v4, CDH3v5, CDH3v6 or CDH3v7, see Tables 11-17) using methods known in the art and used for detecting/labelling cells or as control antibodies in the examples described below. Anti-TRAILR2 scFvs (Table 10) were then linked via the linker described above to the C-terminus of each heavy chain of the anti-CDH3 antibodies, thereby generating bispecific and tetravalent CDH3/TRAILR2 binding molecules (Tables 3-9).

Each expression vector contains eukaryotic promoter elements for the chain-encoding gene, the gene encoding the signal sequence and the heavy or light chain, an expression cassette for a prokaryotic selection marker gene such as ampicillin, and an origin of replication. These DNA plasmids were propagated in ampicillin resistant *E. coli* colonies and purified.

2.4 Expression and Purification of Bispecific, Tetravalent Molecules Recognizing Human TRAILR2 and Human CDH3

Bispecific molecules binding CDH3 and TRAILR2 were produced by transient transfection of CHO-E cells with the pTT5 vectors carrying the CDH3/TRAILR2-chain-encoding genes. Transfected CHO-E cells growing in suspension in serum-free media were cultivated in shake flasks under agitation at 140 rpm, 37° C. and 5% $CO_2$ and kept at conditions of exponential growth. On the day of transfection, cells were chemically transfected with 1 mg of light chain plasmid and 0.5 mg of heavy chain plasmid (1:3 mass ratio). CHO-E cells were then seeded at 1 to $2\times10^6$ cells/mi in 1 L of Gibco® FreeStyle™ CHO expression medium (LifeTechnologies, NY, US). Cells were then incubated under orbital shaking for 10 to 12 days with one-time feeding of 200 ml commercial feed solution to allow expression of the proteins. Antibody titers in the cell culture supernatants were determined using an Octet® instrument (Pall 30 ForteBio, CA, US) and protA biosensor tips according to manufacturer's instructions.

Recombinant CDH3/TRAILR2 binding molecules or antibodies were purified from culture supernatant by a two-step process: in the first purification step by Protein A affinity chromatography using MabSelect™ column (GE Healthcare) followed by the second purification step by Cation exchange chromatography using a Poros 50 HS column (Applied Biosystems, Carlsbad, Calif., USA). The two-step purified material was stored in final buffer of 50 mM Sodium Acetate and 100 mM NaCl, pH 5.0. Purity and degree of heterogeneity of the samples were assessed by mass spectrometry, analytical size-exclusion chromatography and analytical ultracentrifugation. Samples were confirmed to have a monomer content of ≥90% and contain <10% impurities prior to functional testing.

TABLE 3

Amino acid sequences of the bispecific binding molecule CDH3/TRAILR2v7

| SEQ ID NO | Description | CDH3/TR2v7 |
|---|---|---|
| 1 | Modified CDH3 heavy chain incl. TRAILR2 | QVQLQESGPGLVKPSETLSLTCTVSGGSIS**SYYWS**WIRQPPGKGLD WIG**YIYYSRTTNYNPSLKS**RVTISVDTSKNQFSLKLSSVTAADTAV YYCAR**ARNGIDAFDI**WGQGTMVTVSSASTKGPSVFPLAPSSKSTSG GTAALGCLVKDYFPEPVTVSWNSGALTSGVHTFPAVLQSSGLYSLS |

TABLE 3-continued

Amino acid sequences of the bispecific binding molecule CDH3/TRAILR2v7

| SEQ ID NO | Description | CDH3/TR2v7 |
|---|---|---|
| | ScFv | SVVTVPSSSLGTQTYICNVNHKPSNTKVDKRVEPKSCDKTHTCPPCPAPEAAGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGSGGSSSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 2 | CDH3 VH | QVQLQESGPGLVKPSETLSLTCTVSGGSIS**SYYWS**WIRQPPGKGLDWIG**YIYYSRTTNYNPSLKS**RVTISVDTSKNQFSLKLSSVTAADTAVYYCAR**ARNGIDAFDI**WGQGTMVTVSS |
| 3 | HCDR1 | SYYWS |
| 4 | HCDR2 | YIYYSRTTNYNPSLKS |
| 5 | HCDR3 | ARNGIDAFDI |
| 6 | CDH3 VL | DIVMTQSPLSLPVTPGEPASISC**RSSQSLLHSYGYNYLD**WYLQKPGQSPQLLIY**LGSNRAS**GVPDRFSGSGSGTDFTLKISRVEAADVGVYYC**MQALQTPLT**FGGGTKVEIK |
| 7 | LCDR1 | RSSQSLLHSYGYNYLD |
| 8 | LCDR2 | LGSNRAS |
| 9 | LCDR3 | MQALQTPLT |
| 81 | Light chain sequence | DIVMTQSPLSLPVTPGEPASISC**RSSQSLLHSYGYNYLD**WYLQKPGQSPQLLIY**LGSNRAS**GVPDRFSGSGSGTDFTLKISRVEAADVGVYYC**MQALQTPLT**FGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 71 | TRAILR2 SCFv | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 4

Amino acid sequences of the bispecific binding molecule CDH3/TRAILR2v1

| SEQ ID NO | Description | CDH3/TR2v1 |
|---|---|---|
| 11 | Modified heavy chain incl. TRAILR2 SCFv | EVQLVQSGAEVKKPGESLKISCKGSGYSFT**SYWIG**WVRQMPGKGLEWMG**IIYPGDSDTRYSPSFQG**QVTISADKSISTAYLQWSSLKASDTAMYYCAR**HSFFDY**WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKENWYVDGVEVHNAKTKPREEQYNSTYRVVSVLIVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGSGGSSSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 12 | CDH3 VH | EVQLVQSGAEVKKPGESLKISCKGSGYSFT**SYWIG**WVRQMPGKGLEWMG**IIYPGDSDTRYSPSFQG**QVTISADKSISTAYLQWSSLKASDTAMYYCAR**HSFFDY**WGQGTLVTVSS |

TABLE 4-continued

Amino acid sequences of the bispecific binding molecule CDH3/TRAILR2v1

| SEQ ID NO | Description | CDH3/TR2v1 |
|---|---|---|
| 13 | HCDR1 | SYWIG |
| 14 | HCDR2 | IIYPGDSDTRYSPSFQG |
| 15 | HCDR3 | HSFFDY |
| 16 | CDH3 VL | EIVLTQSPGTLSLSPGERATLSC**RASQSVSSIYLA**WYQQKPGQAPRLLIY**GASSRAT**GIPDRFSGSGSGTDFTLTISRLEPEDFAVYYC**QQYSSSPRT**FGQGTKVEIK |
| 17 | LCDR1 | RASQSVSSIYLA |
| 18 | LCDR2 | GASSRAT |
| 19 | LCDR3 | QQYSSSPRT |
| 83 | Light Chain Sequence | EIVLTQSPGTLSLSPGERATLSC**RASQSVSSIYLA**WYQQKPGQAPRLLIY**GASSRAT**GIPDRFSGSGSGTDFTLTISRLEPEDFAVYYC**QQYSSSPRT**FGQGTKVEIKRTVAAPSVFIFPPSDEQLKSGTASVVCLLNNFYPREAKVQWKVDNALQSGNSQESVTEQDSKDSTYSLSSTLILSKADYEKHKVYACEVTHQGLSSPVTKSENRGEC |
| 71 | TRAILR2 SCFv | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 5

Amino acid sequences of the bispecific binding molecule CDH3/TRAILR2v2

| SEQ ID NO | Description | CDH3/TR2v2 |
|---|---|---|
| 21 | Modified heavy chain incl. TRAILR2 SCFV | QVQLQESGPGLVKPSETLSLTCTVSGGSIS**NYYWS**WIRQPPGKGLEWIG**YMYYSGITNYNPSLKS**RVTISVDTSKNQFSLKLNSVTTADTAVYYCAR**ERNGIDGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGSGGSSSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 22 | CDH3 VH | QVQLQESGPGLVKPSETLSLTCTVSGGSIS**NYYWS**WIRQPPGKGLEWIG**YMYYSGITNYNPSLKS**RVTISVDTSKNQFSLKLNSVTTADTAVYYCAR**ERNGIDGMDV**WGQGTTVTVSS |
| 23 | HCDR1 | NYYWS |
| 24 | HCDR2 | YMYYSGITNYNPSLKS |
| 25 | HCDR3 | ERNGIDGMDV |
| 26 | CDH3 VL | DIVMTQSPLSLPVTPGEPASISC**RSSQSLLHSYGYNYLD**WYLQKPGQSPQLLIY**LGSNRAS**GVPDRFSGSGSGTDFTLKISRVEAEDFGIYYC**MQALQTPIT**FGQGTRLEIK |
| 27 | LCDR1 | RSSQSLLHSYGYNYLD |
| 28 | LCDR2 | LGSNRAS |
| 29 | LCDR3 | MQALQTPIT |

TABLE 5-continued

Amino acid sequences of the bispecific binding molecule CDH3/TRAILR2v2

| SEQ ID NO | Description | CDH3/TR2v2 |
|---|---|---|
| 85 | Light Chain Sequence | DIVMTQSPLSLPVTPGEPASISC**RSSQSLLHSYGYNYLD**WYLQKPGQSPQLLIY**LGSNRAS**GVPDRFSGSGSGTDFTLKISRVEAEDFGIYYC**MQALQTPIT**FGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 71 | TRAILR2 SCFV | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 6

Amino acid sequences of the bispecific binding molecule CDH3/TRAILR2v3

| SEQ ID NO | Description | CDH3/TR2v3 |
|---|---|---|
| 31 | Modified heavy chain incl. TRAILR2 SCFV | QVQLQESGPGLVKPSETLSLTCTVSGGSIS**GYYWS**WIRQSPGKGLEWIG**YIYYSANTNYNPSLKS**RVTISVDTSKNQFSLKLSSVTAADTAVYYCSR**GGSGSYWAFDI**WGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGSGGSSSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 32 | CDH3 VH | QVQLQESGPGLVKPSETLSLTCTVSGGSIS**GYYWS**WIRQSPGKGLEWIG**YIYYSANTNYNPSLKS**RVTISVDTSKNQFSLKLSSVTAADTAVYYCSR**GGSGSYWAFDI**WGQGTMVTVSS |
| 33 | HCDR1 | GYYWS |
| 34 | HCDR2 | YIYYSANTNYNPSLKS |
| 35 | HCDR3 | GGSGSYWAFDI |
| 36 | CDH3 VL | DIVMTQSPLSLPVTPGEPASISC**RSSQSLMYSYGYNYLD**WYLQKPGQSPQLLIY**LGSNRAS**GVPDRFSGSGSGTDFTLKISRVEAEDVGIYYC**MQALQTPPT**FGQGTKVEIK |
| 37 | LCDR1 | RSSQSLMYSYGYNYLD |
| 38 | LCDR2 | LGSNRAS |
| 39 | LCDR3 | MQALQTPPT |
| 87 | Light Chain Sequence | DIVMTQSPLSLPVTPGEPASISC**RSSQSLMYSYGYNYLD**WYLQKPGQSPQLLIY**LGSNRAS**GVPDRFSGSGSGTDFTLKISRVEAEDVGIYYC**MQALQTPPT**FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVIKSENRGEC |
| 71 | TrailR2 SCFv | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 7

Amino acid sequences of the bispecific binding molecule CDH3/TRAILR2v4

| SEQ ID NO | Description | CDH3/TR2v4 |
|---|---|---|
| 41 | Modified heavy chain incl. TRAILR2 SCFV | QVQLQESGPGLVKPSETLSLTCTVSGGSIS**GYYWS**WIRQPAGKGLEWIG**RIYTSGNTIYNPSLKS**RVTMSVDTSKNQFSLRLTSVTAADTAVYYCAR**GNPLATYFGY**WGQGTLVTVSSASTKGPSVEPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGSGGSSSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 42 | CDH3 VH | QVQLQESGPGLVKPSETLSLTCTVSGGSIS**GYYWS**WIRQPAGKGLEWIG**RIYTSGNTIYNPSLKS**RVTMSVDTSKNQFSLRLTSVTAADTAVYYCAR**GNPLATYFGY**WGQGTLVTVSS |
| 43 | HCDR1 | GYYWS |
| 44 | HCDR2 | RIYTSGNTIYNPSLKS |
| 45 | HCDR3 | GNPLATYFGY |
| 46 | CDH3 VL | DIEMTQSPDSLAVSLGERATINC**KSSQSVLYSSNNKNYLA**WYQQKPGQPPKLLIY**WASTRES**GVPDRFSGSGSGTDFTLTISSLQAEDVAVYYC**QQYYSTMYT**FGQGTKLEIK |
| 47 | LCDR1 | KSSQSVLYSSNNKNYLA |
| 48 | LCDR2 | WASTRES |
| 49 | LCDR3 | QQYYSTMYT |
| 89 | Light Chain sequence | DIEMTQSPDSLAVSLGERATINC**KSSQSVLYSSNNKNYLA**WYQQKPGQPPKLLIY**WASTRES**GVPDRFSGSGSGTDFTLTISSLQAEDVAVYYC**QQYYSTMYT**FGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 71 | TRAILR2 SCFV | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 8

Amino acid sequences of the bispecific binding molecule CDH3/TRAILR2v5

| SEQ ID NO | Description | CDH3/TR2v5 |
|---|---|---|
| 51 | Modified heavy chain incl. TRAILR2 SCFV | QVQLQESGPGLVKPSETLSLTCTVSGGSIS**SYYWS**WFRQPAGKGLEWIG**RIYSSGSTNYNPSLKS**RVTMSVDTSKNQFSLKLSSVTAADTAVYYCAR**GMGVTGLFDY**WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGSGGSSSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 8-continued

Amino acid sequences of the bispecific binding molecule CDH3/TRAILR2v5

| SEQ ID NO | Description | CDH3/TR2v5 |
|---|---|---|
| 52 | CDH3 VH | QVQLQESGPGLVKPSETLSLTCTVSGGSIS**SYYWS**WFRQPAGKGLEWIG**RIYSSGSTNYNPSLKS**RVTMSVDTSKNQFSLKLSSVTAADTAVYYCAR**GMGVTGLFDY**WGQGTLVTVSS |
| 53 | HCDR1 | SYYWS |
| 54 | HCDR2 | RIYSSGSTNYNPSLKS |
| 55 | HCDR3 | GMGVTGLFDY |
| 56 | CDH3 VL | DIVMTQSPDSLAVSLGERATINC**KSSQSVLYSSNNKNYLA**WYQQKPGQPPKLLIY**WASTRES**GVPDRFSGSGSGTDFTLTISSLQAEDVAVYYC**QQYYSTMYT**FGQGTKLEIK |
| 57 | LCDR1 | KSSQSVLYSSNNKNYLA |
| 58 | LCDR2 | WASTRES |
| 59 | LCDR3 | QQYYSTMYT |
| 91 | Light Chain sequence | DIVMTQSPDSLAVSLGERATINC**KSSQSVLYSSNNKNYLA**WYQQKPGQPPKLLIY**WASTRES**GVPDRFSGSGSGTDFTLTISSLQAEDVAVYYC**QQYYSTMYT**FGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 71 | TRAILR2 SCFV | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 9

Amino acid sequences of the bispecific binding molecule CDH3/TRAILR2v6

| SEQ ID NO | Description | CDH3/TR2v6 |
|---|---|---|
| 61 | Modified heavy chain incl. TRAILR2 SCFV | QVQLQESGPGLVKPSETLSLTCTVSGGSIN**NYYWT**WIRQPAGKGLEWIG**RIYSSGSTNYTPSLKS**RVTMSVDTSKNQFSLKLSSVTAADTAVYFCAR**EGYNDGYGYFDH**WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGSGGSSSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 62 | CDH3 VH | QVQLQESGPGLVKPSETLSLTCTVSGGSIN**NYYWT**WIRQPAGKGLEWIG**RIYSSGSTNYTPSLKS**RVTMSVDTSKNQFSLKLSSVTAADTAVYFCAR**EGYNDGYGYFDH**WGQGTLVTVSS |
| 63 | HCDR1 | NYYWT |
| 64 | HCDR2 | RIYSSGSTNYTPSLKS |
| 65 | HCDR3 | EGYNDGYGYFDH |
| 66 | CDH3 VL | DIVMTQSPDSLAVSLGERATINC**KSSQSVLYSSKNKNYLA**WYQQKPGQPPKLLIY**WASTRES**GVPDRFSGSGSGTDFTLTISSLQAEDVAVYYC**QQYYSTFRT**FGQGTKVEIK |
| 67 | LCDR1 | KSSQSVLYSSKNKNYLA |
| 68 | LCDR2 | WASTRES |

TABLE 9-continued

Amino acid sequences of the bispecific binding molecule CDH3/TRAILR2v6

| SEQ ID NO | Description | CDH3/TR2v6 |
|---|---|---|
| 69 | LCDR3 | QQYYSTFRT |
| 93 | Light Chain sequence | DIVMTQSPDSLAVSLGERATINC**KSSQSVLYSSKNKNYLA**WYQQKPGQPPKLLIY**WASTRES**GVPDRFSGSGSGTDFTLTISSLQAEDVAVYYC**QQYYSTFRT**FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 71 | TRAILR2 SCFV | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |

TABLE 10

Amino acid sequences of the TRAILR2 scFv used in the bispecific binding molecules generated in Example 2.

| SEQ ID NO | Description | |
|---|---|---|
| 71 | TRAILR2 SCFV | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVLGGGGSGGGGSGGGGSGGGGSEVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 72 | TRAILR2 SCFV VH | EVQLVQSGGGVERPGGSLRLSCAASGFTFD**DYGMS**WVRQAPGKGLEWVS**GINWNGGSTGYADSVKG**RVTISRDNAKNSLYLQMNSLRAEDTAVYYCAK**ILGAGRGWYFDL**WGKGTTVTVSS |
| 73 | SCFv HCDR1 | DYGMS |
| 74 | SCFV HCDR2 | GINWNGGSTGYADSVKG |
| 75 | SCFv HCDR3 | ILGAGRGWYFDL |
| 76 | TRAILR2 SCFv VL | SSELTQDPAVSVALGQTVRITC**QGDSLRSYYAS**WYQQKPGQAPVLVIY**GKNNRPS**GIPDRFSGSSSGNTASLTITGAQAEDEADYYC**NSRDSSGNHVV**FGGGTKLTVL |
| 77 | SCFv LCDR1 | QGDSLRSYYAS |
| 78 | SCFV LCDR2 | GKNNRPS |
| 79 | SCFv LCDR3 | NSRDSSGNHVV |

TABLE 11

Amino acid sequences of the anti-CDH3 antibody CDH3v7

| SEQ ID NO | Description | CDH3v7 |
|---|---|---|
| 80 | heavy chain sequence | QVQLQESGPGLVKPSETLSLTCTVSGGSIS**SYYWS**WIRQPPGKGLDWIG**YIYYSRTTNYNPSLKS**RVTISVDTSKNQFSLKLSSVTAADTAVYYCAR**ARNGIDAFDI**WGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |

TABLE 11-continued

| Amino acid sequences of the anti-CDH3 antibody CDH3v7 | | |
|---|---|---|
| SEQ ID NO | Description | CDH3v7 |
| 81 | light chain sequence | DIVMTQSPLSLPVTPGEPASISC**RSSQSLLHSYGYNYLD**WYLQKPGQSPQLLIY**LGSNRAS**GVPDRFSGSGSGTDFTLKISRVEAADVGVYYC**MQALQTPLT**FGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 2 | VH | QVQLQESGPGLVKPSETLSLTCTVSGGSIS**SYYWS**WIRQPPGKGLDWIG**YIYYSRTTNYNPSLKS**RVTISVDTSKNQFSLKLSSVTAADTAVYYCAR**ARNGIDAFDI**WGQGTMVTVSS |
| 3 | HCDR1 | SYYWS |
| 4 | HCDR2 | YIYYSRTTNYNPSLKS |
| 5 | HCDR3 | ARNGIDAFDI |
| 6 | VL | DIVMTQSPLSLPVTPGEPASISC**RSSQSLLHSYGYNYLD**WYLQKPGQSPQLLIY**LGSNRAS**GVPDRFSGSGSGTDFTLKISRVEAADVGVYYC**MQALQTPLT**FGGGTKVEIK |
| 7 | LCDR1 | RSSQSLLHSYGYNYLD |
| 8 | LCDR2 | LGSNRAS |
| 9 | LCDR3 | MQALQTPLT |

TABLE 12

| Amino acid sequences of the anti-CDH3 antibody CDH3v1 | | |
|---|---|---|
| SEQ ID NO | Description | CDH3v1 |
| 82 | Heavy Chain Sequence | EVQLVQSGAEVKKPGESLKISCKGSGYSFT**SYWIG**WVRQMPGKGLEWMG**IIYPGDSDTRYSPSFQG**QVTISADKSISTAYLQWSSLKASDTAMYYCAR**HSFFDY**WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 83 | Light Chain Sequence | EIVLTQSPGTLSLSPGERATLSC**RASQSVSSIYLA**WYQQKPGQAPRLLIY**GASSRAT**GIPDRFSGSGSGTDFTLTISRLEPEDFAVYYC**QQYSSSPRT**FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 12 | VH | EVQLVQSGAEVKKPGESLKISCKGSGYSFT**SYWIG**WVRQMPGKGLEWMG**IIYPGDSDTRYSPSFQG**QVTISADKSISTAYLQWSSLKASDTAMYYCAR**HSFFDY**WGQGTLVTVSS |
| 13 | HCDR1 | SYWIG |
| 14 | HCDR2 | IIYPGDSDTRYSPSFQG |
| 15 | HCDR3 | HSFFDY |
| 16 | VL | EIVLTQSPGTLSLSPGERATLSC**RASQSVSSIYLA**WYQQKPGQAPRLLIY**GASSRAT**GIPDRFSGSGSGTDFTLTISRLEPEDFAVYYC**QQYSSSPRT**FGQGTKVEIK |
| 17 | LCDR1 | RASQSVSSIYLA |
| 18 | LCDR2 | GASSRAT |
| 19 | LCDR3 | QQYSSSPRT |

TABLE 13

| Amino acid sequences of the anti-CDH3 antibody CDH3v2 | | |
|---|---|---|
| SEQ ID NO | Description | CDH3v2 |
| 84 | Heavy Chain Sequence | QVQLQESGPGLVKPSETLSLTCTVSGGSIS**NYYWS**WIRQPPGKGLEWIG**YMYYSGITNYNPSLKS**RVTISVDTSKNQFSLKLNSVTTADTAVYYCAR**ERNGIDGMDV**WGQGTTVTVSSASTKGPSVEPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 85 | Light Chain Sequence | DIVMTQSPLSLPVTPGEPASISC**RSSQSLLHSYGYNYLD**WYLQKPGQSPQLLIY**LGSNRAS**GVPDRFSGSGSGTDFTLKISRVEAEDFGIYYC**MQALQTPIT**FGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 22 | VH | QVQLQESGPGLVKPSETLSLTCTVSGGSIS**NYYWS**WIRQPPGKGLEWIG**YMYYSGITNYNPSLKS**RVTISVDTSKNQFSLKLNSVTTADTAVYYCAR**ERNGIDGMDV**WGQGTTVTVSS |
| 23 | HCDR1 | NYYWS |
| 24 | HCDR2 | YMYYSGITNYNPSLKS |
| 25 | HCDR3 | ERNGIDGMDV |
| 26 | VL | DIVMTQSPLSLPVTPGEPASISC**RSSQSLLHSYGYNYLD**WYLQKPGQSPQLLIY**LGSNRAS**GVPDRFSGSGSGTDFTLKISRVEAEDFGIYYCMQALQTPITFGQGTRLEIK |
| 27 | LCDR1 | RSSQSLLHSYGYNYLD |
| 28 | LCDR2 | LGSNRAS |
| 29 | LCDR3 | MQALQTPIT |

TABLE 14

| Amino acid sequences of the anti-CDH3 antibody CDH3v3 | | |
|---|---|---|
| SEQ ID NO | Description | CDH3v3 |
| 86 | Heavy Chain Sequence | QVQLQESGPGLVKPSETLSLTCTVSGGSIS**GYYWS**WIRQSPGKGLEWIG**YIYYSANTNYNPSLKS**RVTISVDTSKNQFSLKLSSVTAADTAVYYCSR**GGSGSYWAFDI**WGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 87 | Light Chain Sequence | DIVMTQSPLSLPVTPGEPASISC**RSSQSLMYSYGYNYLD**WYLQKPGQSPQLLIY**LGSNRAS**GVPDRFSGSGSGTDFTLKISRVEAEDVGIYYC**MQALQTPPT**FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 32 | VH | QVQLQESGPGLVKPSETLSLTCTVSGGSIS**GYYWS**WIRQSPGKGLEWIG**YIYYSANTNYNPSLKS**RVTISVDTSKNQFSLKLSSVTAADTAVYYCSR**GGSGSYWAFDI**WGQGTMVTVSS |
| 33 | HCDR1 | GYYWS |
| 34 | HCDR2 | YIYYSANTNYNPSLKS |
| 35 | HCDR3 | GGSGSYWAFDI |

TABLE 14-continued

| Amino acid sequences of the anti-CDH3 antibody CDH3v3 | | |
|---|---|---|
| SEQ ID NO | Description | CDH3v3 |
| 36 | VL | DIVMTQSPLSLPVTPGEPASISC**RSSQSLMYSYGYNYLD**WYLQKPGQSPQLLIY**LGSNRAS**GVPDRFSGSGSGTDFTLKISRVEAEDVGIYYC**MQALQTPPT**FGQGTKVEIK |
| 37 | LCDR1 | RSSQSLMYSYGYNYLD |
| 38 | LCDR2 | LGSNRAS |
| 39 | LCDR3 | MQALQTPPT |

TABLE 15

| Amino acid sequences of the anti-CDH3 antibody CDH3v4 | | |
|---|---|---|
| SEQ ID NO | Description | CDH3v4 |
| 88 | Heavy Chain sequence | QVQLQESGPGLVKPSETLSLTCTVSGGSIS**GYYWS**WIRQPAGKGLEWIG**RIYTSGNTIYNPSLKS**RVTMSVDTSKNQFSLRLTSVTAADTAVYYCAR**GNPLATYFGY**WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKENWYVDGVEVHNAKTKPREEQYNSTYRVVSVLIVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 89 | Light Chain sequence | DIEMTQSPDSLAVSLGERATINC**KSSQSVLYSSNNKNYLA**WYQQKPGQPPKLLIY**WASTRES**GVPDRFSGSGSGTDFTLTISSLQAEDVAVYYC**QQYYSTMYT**FGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |
| 42 | VH | QVQLQESGPGLVKPSETLSLTCTVSGGSIS**GYYWS**WIRQPAGKGLEWIG**RIYTSGNTIYNPSLKS**RVTMSVDTSKNQFSLRLTSVTAADTAVYYCAR**GNPLATYFGY**WGQGTLVTVSS |
| 43 | HCDR1 | GYYWS |
| 44 | HCDR2 | RIYTSGNTIYNPSLKS |
| 45 | HCDR3 | GNPLATYFGY |
| 46 | VL | DIEMTQSPDSLAVSLGERATINC**KSSQSVLYSSNNKNYLA**WYQQKPGQPPKLLIY**WASTRES**GVPDRFSGSGSGTDFTLTISSLQAEDVAVYYC**QQYYSTMYT**FGQGTKLEIK |
| 47 | LCDR1 | KSSQSVLYSSNNKNYLA |
| 48 | LCDR2 | WASTRES |
| 49 | LCDR3 | QQYYSTMYT |

TABLE 16

| Amino acid sequences of the anti-CDH3 antibody CDH3v5 | | |
|---|---|---|
| SEQ ID NO | Description | CDH3v5 |
| 90 | Heavy Chain sequence | QVQLQESGPGLVKPSETLSLTCTVSGGSIS**SYYWS**WFRQPAGKGLEWIG**RIYSSGSTNYNPSLKS**RVTMSVDTSKNQFSLKLSSVTAADTAVYYCAR**GMGVTGLFDY**WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKENWYVDGVEVHNAKTKPREEQYNSTYRVVSVLTVLHQDWLNGKEYKC |

TABLE 16-continued

| Amino acid sequences of the anti-CDH3 antibody CDH3v5 | | |
|---|---|---|
| SEQ ID NO | Description | CDH3v5 |
| | | KVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPG |
| 91 | Light Chain sequence | DIVMTQSPDSLAVSLGERATINCKSSQSVLYSSNNKNYLAWYQQKP GQPPKLLIYWASTRESGVPDRFSGSGSGTDFTLTISSLQAEDVAVY YCQQYYSTMYTFGQGTKLEIKRTVAAPSVFIFPPSDEQLKSGTASV VCLLNNFYPREAKVQWKVDNALQSGNSQESVTEQDSKDSTYSLSST LTLSKADYEKHKVYACEVTHQGLSSPVTKSENRGEC |
| 52 | VH | QVQLQESGPGLVKPSETLSLTCTVSGGSIS**SYYWS**WFRQPAGKGLE WIG**RIYSSGSTNYNPSLKS**RVTMSVDTSKNQFSLKLSSVTAADTAV YYCAR**GMGVTGLFDY**WGQGTLVTVSS |
| 53 | HCDR1 | SYYWS |
| 54 | HCDR2 | RIYSSGSTNYNPSLKS |
| 55 | HCDR3 | GMGVTGLFDY |
| 56 | VL | DIVMTQSPDSLAVSLGERATINC**KSSQSVLYSSNNKNYLA**WYQQKP GQPPKLLIY**WASTRES**GVPDRFSGSGSGTDFTLTISSLQAEDVAVY YC**QQYYSTMYT**FGQGTKLEIK |
| 57 | LCDR1 | KSSQSVLYSSNNKNYLA |
| 58 | LCDR2 | WASTRES |
| 59 | LCDR3 | QQYYSTMYT |

TABLE 17

| Amino acid sequences of the anti-CDH3 antibody CDH3v6 | | |
|---|---|---|
| SEQ ID NO | Description | CDH3v6 |
| 92 | Heavy Chain sequence | QVQLQESGPGLVKPSETLSLTCTVSGGSIN**NYYWT**WIRQPAGKGLE WIG**RIYSSGSTNYTPSLKS**RVTMSVDTSKNQFSLKLSSVTAADTAV YFCAR**EGYNDGYGYFDH**WGQGTLVTVSSASTKGPSVEPLAPSSKST SGGTAALGCLVKDYFPEPVTVSWNSGALTSGVHTFPAVLQSSGLYS LSSVVTVPSSSLGTQTYICNVNHKPSNTKVDKRVEPKSCDKTHTCP PCPAPEAAGGPSVFLFPPKPKDTLMISRTPEVTCVVVDVSHEDPEV KFNWYVDGVEVHNAKTKPREEQYNSTYRVVSVLIVLHQDWLNGKEY KCKVSNKALPAPIEKTISKAKGQPREPQVYTLPPSREEMTKNQVSL TCLVKGFYPSDIAVEWESNGQPENNYKTTPPVLDSDGSFFLYSKLT VDKSRWQQGNVFSCSVMHEALHNHYTQKSLSLSPG |
| 93 | Light Chain sequence | DIVMTQSPDSLAVSLGERATINC**KSSQSVLYSSKNKNYLA**WYQQKP GQPPKLLIY**WASTRES**GVPDRFSGSGSGTDFTLTISSLQAEDVAVY YC**QQYYSTFRT**FGQGTKVEIKRTVAAPSVFIFPPSDEQLKSGTASV VCLLNNFYPREAKVQWKVDNALQSGNSQESVTEQDSKDSTYSLSST LTLSKADYEKHKVYACEVTHQGLSSPVTKSENRGEC |
| 62 | VH | QVQLQESGPGLVKPSETLSLTCTVSGGSIN**NYYWT**WIRQPAGKGLE WIG**RIYSSGSTNYTPSLKS**RVTMSVDTSKNQFSLKLSSVTAADTAV YFCAR**EGYNDGYGYFDH**WGQGTLVTVSS |
| 63 | HCDR1 | NYYWT |
| 64 | HCDR2 | RIYSSGSTNYTPSLKS |
| 65 | HCDR3 | EGYNDGYGYFDH |
| 66 | VL | DIVMTQSPDSLAVSLGERATINC**KSSQSVLYSSKNKNYLA**WYQQKP GQPPKLLIY**WASTRES**GVPDRFSGSGSGTDFTLTISSLQAEDVAVY YC**QQYYSTFRT**FGQGTKVEIK |

TABLE 17-continued

| Amino acid sequences of the anti-CDH3 antibody CDH3v6 | | |
|---|---|---|
| SEQ ID NO | Description | CDH3v6 |
| 67 | LCDR1 | KSSQSVLYSSKNKNYLA |
| 68 | LCDR2 | WASTRES |
| 69 | LCDR3 | QQYYSTFRT |

2.5: SPR Based Determination of Binding Affinities of Bispecific Molecules to Recombinant CDH3

The binding affinity of purified CDH3/TRAILR2 bispecific constructs for recombinant human CDH3 (either full-length, EC1-EC2 or EC2-EC3) was determined by Surface Plasmon Resonance (SPR), using a ProteOn XPR36 instrument (Bio-Rad). The running buffer and all dilutions (except where stated) were done in PBS-TEDTA. The GLM sensor chip (Bio-Rad) was normalized and pre-conditioned as per the manufacturers recommendations. The sensor chip was activated with equal mixture of EDC/s-NHS in the horizontal direction for 300 sec at a flow rate of 30 μl/min and immobilized with protein A/G (60 μg/ml in 10 mM acetate pH 4.5) in the horizontal direction for 300 sec at a flowrate of 30 μl/min resulting in 5000 RU of protein A/G on the surface. The sensor chip was deactivated with 1 M ethanolamine HCl in the horizontal direction for 300 sec at a flowrate of 30 μl/min. The sensor chip was stabilized with 18 sec of 0.85% phosphoric acid at a flowrate of 100 μl/min 3 times horizontally and 3 times vertically.

For binding kinetic determination to CDH3, bispecific molecules were captured individually on the protein A/G surface vertically for 150 sec at a flowrate of 30 μl/min. The baseline was stabilized by injecting PBS-T-EDTA for 60 sec at a flowrate of 100 μl/min horizontally. The analyte (human full-length CDH3, CDH3 [EC1-EC2] or CDH3 [EC2-EC3]) was injected horizontally over the captured antibody for 300 sec at a flowrate of 30 μl/min and a dissociation for 1200 sec. The concentration of the analytes injected was 200 nM for the full-length CDH3 and 500 nM for EC1-EC2 and EC2-EC3. The surface was regenerated by injecting 0.85% phosphoric acid solution for 18 sec at a flowrate of 100 μl/min one time horizontally and one time vertically. Data was processed by subtracting the interspot (interactions with sensor surface) and then fit to 1:1 Langmuir kinetic model to obtain rate constants and affinities.

Affinities to CDH3 (full-length or EC1-EC2) were in the low nM range. Binding affinities to EC2-EC3 peptide was either in the low nM range (mapping the epitope to EC2) or below detection level (mapping the epitope to EC1).

Results are shown in Table 18 below, classifying the produced binding molecules comprising CDH3v1, CDH3v2, CDH3v3 or CDH3v7 as EC1 binders and those comprising CDH3v4, CDHv5 or CDHv6 as EC2 binders.

TABLE 18

| Affinities (KD) of CDH3/TRAILR2 binding proteins to human CDH3 as determined by SPR analysis | | | | |
|---|---|---|---|---|
| CDH3/TRAILR2 Bispecific molecule | Epitope mapping (EC1 or EC2 binder) | HuCDH3 full-length kD (nM) | HuCDH3 EC1-EC2 kD (nM) | HuCDH3_EC2-EC3 kD (nM) |
| CDH3/TR2v1 | EC1 | 8.52 | 6.7 | BDL |
| CDH3/TR2v2 | EC1 | 9.93 | 11.40 | BDL |
| CDH3/TR2v3 | EC1 | 1.08 | 0.85 | BDL |
| CDH3/TR2v4 | EC2 | 5.36 | 1.62 | 1.06 |
| CDH3/TR2v5 | EC2 | 2.43 | 2.76 | 29.80 |
| CDH3/TR2v6 | EC2 | 3.19 | 2.79 | 35.10 |
| CDH3/TR2v7 | EC1 | 3.29 | 4.00 | BDL |

BDL: Below detection limit

Example 3: In Vitro Cell Killing Assay

The Examples set out above show the preparation of bispecific molecules recognizing TRAILR2 and human CDH3. A number of different bispecific molecules based on the format depicted in FIG. 3 were prepared in order to examine whether these molecules could cause a reduction in cell viability and whether any such reduction was caused by apoptosis.

3.1 Characterizing Target Expression in the GP2d Cell Line Model.

Figure 4:
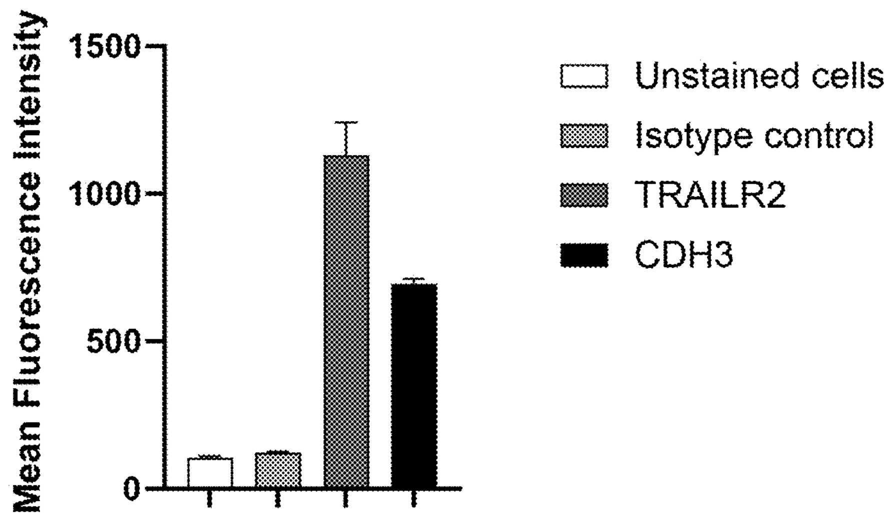
FIG. 4: Flow-cytometry analysis of the protein surface expression of TRAILR2 and CDH3 in GP2d cells. Results are shown as the mean fluorescence intensity.

The cell line GP2d, which is derived from a human colon adenocarcinoma, was chosen to conduct cell killing assays. TRAILR2 and CDH3 protein surface expression on GP2d cells was confirmed by Flow-Cytometry as follows. Cells were detached using Versene solution (Gibco 15040066) and washed twice with FACS buffer (PBS, Gibco 14190; 3% FCS, Gibco 26140; and 0.09% $NaN_3$, Sigma Aldrich S2002). Cells were counted using the ViCell (Beckman Coulter Life Sciences) and the cell number adjusted to $2\times10^6$ cells/ml. After seeding 100 μl/well cell suspension in a 96-well round bottom plate, the plate was centrifuged at 1200 rpm for 5 minutes and the supernatant were discarded. Cells were then resuspended in the primary antibody dilution (1 μg/ml) and incubated for 60 min at 4° C. Cells were washed twice with FACS buffer and 100 μl/well of the appropriated dilution of secondary/conjugated antibodies was added and incubated for 45 min at 4° C. in the dark. After two washes with FACS buffer, cells were resuspended in 100 μl FACS buffer per well and analysed on a FACS Canto (BD Biosciences). For TRAILR2 detection, conjugated anti-human CD262 (DR5) PE (eBioscience, 12-9908-42) was used. For CDH3 detection, the anti-P-cadherin antibody (GeneTex GTX52961) followed by a secondary anti-mouse IgG FITC was used. As control, a mouse IgG isotype control was used. In FIG. 4 the protein surface expression of TRAILR2 and CDH3 in GP2d cells is shown, with both proteins proving significant expression.

3.2 Effect of the Bispecific CDH3/TRAILR2 Molecules on the GP2d Cells (In Vitro 2D)

Having identified GP2d cells as a suitable cancer cell line to assess the function of the bispecific CDH3/TRAILR2 binding molecules, the following assay was devised. GP2d cells were plated in culture medium (RPM11640/Glutamax, Gibco 61870-010; plus 10% FCS, Gibco 26140). After resting overnight at 3TC and 5% $CO_2$, cells were incubated during 24 hours with 50 μl of different antibody or binding molecule dilutions at the desired concentrations. Cell viability was then assessed by using the CellTiter-Glo Luminescent Cell Viability Assay (Promega G7571) according to the instructions provided by the manufacturer. Finally, luminescence was recorded using the VICTOR X4 2030 Multilabel Plate Reader from Perkin Elmer. Two TRAILR2 binders, an anti-TRAILR2 IgG, typically referred to as Lexatumumab (HGS-ETR2, WO2003054216A3), and an anti-TRAILR2 nanobody (WO2011098520A1), were used as controls (both synthesized in-house). The sequence source for Lexatumumab was obtained from the World Health Organization, as listed in the Recommended international nonproprietary names (World Health Organization. Recommended international nonproprietary names, list 57. *WHO Drug Information* 2007; 21:53-83.). The expression vector of the anti-TRAILR2 nanobody was produced as described in WO 2011/098520, SEQ ID No: 032.

GP2d cells were incubated for 24 hours with (i) the bispecific molecule (CDH3/TR2v1), (ii) anti-TRAILR2 antibody alone (Lexatumumab), (iii) anti-CDH3 antibody alone (anti-CDH3v1 or anti-CDH3v2), or (iv) the equivalent combination of anti-TRAILR2 and CDH3 (CDH3v1 or CDH3v2) antibodies.

Figure 5:
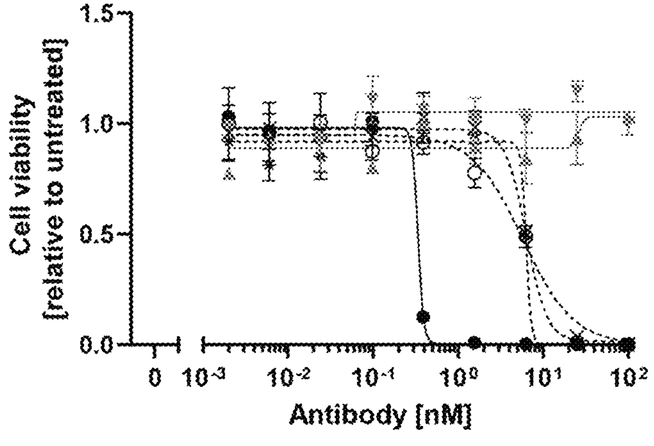
FIG. 5: Effect of antibodies incubation on cell viability. GP2d cells were treated for 24 h with different concentrations of (i) CDH3/TRAILR2 bispecific molecule (CDH3/TR2v1), (ii) anti-TRAILR2 alone (Lexatumumab), (iii) anti-CDH3v1 (or anti-CDH3v2) alone, or (iv) the equivalent combination of separate anti-TRAILR2 (Lexatumumab) and anti-CDH3v1 (or anti-CDH3v2) antibodies. The data is expressed as mean relative values compared to untreated control.

FIG. 5 shows the effect of these molecules on cell viability. The two CDH3 molecules (anti-CDH3v1 or anti-CDH3v2) alone had no effect on cell viability. The TRAILR2 antibody (Lexatumumab) alone was able to significantly decrease cell viability (EC50: 5.802 nM), and the addition of anti-CDH3 in free-combination (either anti-CDH3v1 or anti-CDH3v2) did not change the effect observed with anti-TRAILR2 antibody alone. The bispecific CDH3/TRAILR2 binding molecule CDH3/TRAILR2v1 described above lead to potent killing of GP2d cells (EC50: 0.337 nM) with a 17-fold improved potency compared to anti-TRAILR2 antibody alone (Lexatumumab) or anti-TRAILR2 antibody in combination with anti-CDH3 antibody (either anti-CDH3v1 or anti-CDH3v2).

A number of different bispecific molecules were compared to the tetravalent anti-TRAILR2 nanobody in the same assay using GP2d cells.

Figure 6:
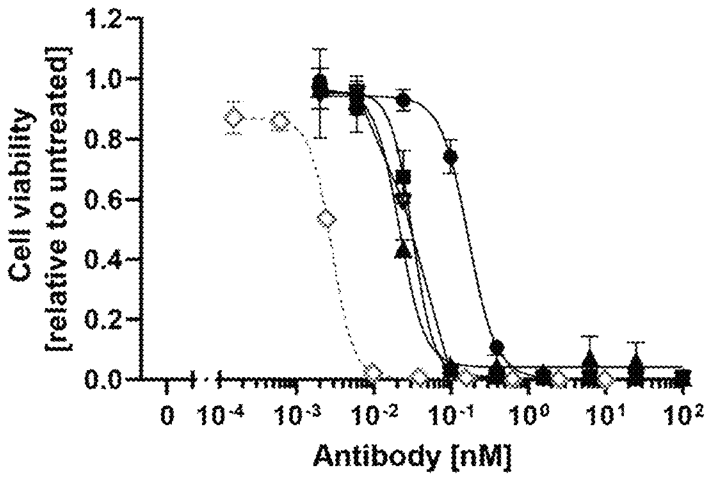
FIG. 6: Effect of antibodies incubation on cell viability. GP2d cells were treated for 24 h with different concentrations of (i) bispecific CDH3/TRAILR2 molecules binding in EC1 of CDH3 (CDH3/TRAILR2v1, CDH3/TRAILR2v2, CDH3/TRAILR2v3, CDH3/TRAILR2v7) or (ii) anti-TRAILR2 alone (anti-TRAILR2 nanobody). The data is expressed as mean relative values compared to untreated control.

FIG. 6 shows the potency of 4 bispecific molecules binding TRAILR2 and the EC1 domain of CDH3 (CDH3/TRAILR2v1, CDH3/TRAILR2v2, CDH3/TRAILR2v3, CDH3/TRAILR2v7), which were approximately 55-fold, 11-fold, or 7-fold less potent than the anti-TRAILR2 nanobody.

Figure 7:
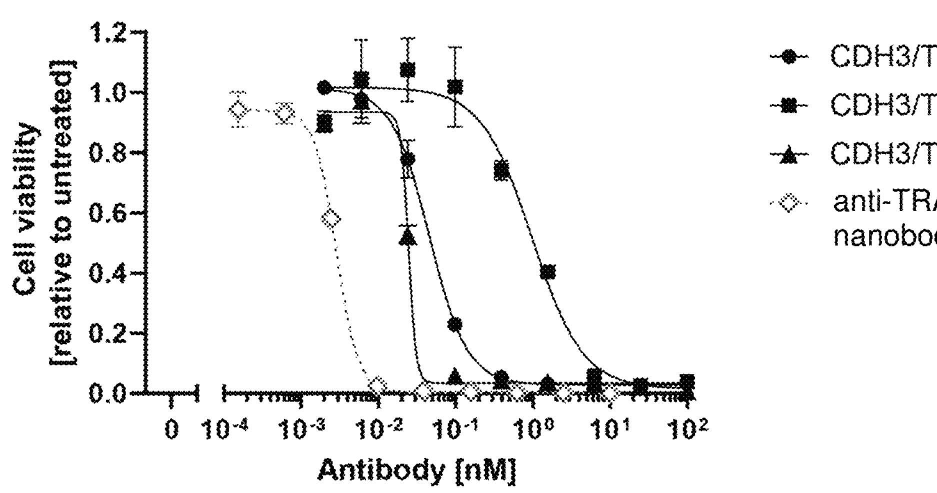
FIG. 7: Effect of antibodies incubation on cell viability. GP2d cells were treated for 24 h with different concentrations of (i) bispecific CDH3/TRAILR2 molecules binding in EC2 of CDH3 (CDH3/TRAILR2v4, CDH3/TRAILR22v5, CDH3/TRAILR2v6) or (ii) anti-TRAILR2 alone (anti-TRAILR2 nanobody). The data is expressed as mean relative values compared to untreated control.

FIG. 7 shows the potency of 3 bispecific molecules binding TRAILR2 and the EC2 domain of CDH3 (CDH3/TRAILR2v4, CDH3/TRAILR2v5, CDH3/TRAILR2v6), which were approximately 15-fold, 327-fold, or 8-fold less potent than the anti-TRAILR2 nanobody.

3.3 Effect of the Bispecific CDH3/TRAILR2 Molecules on GP2d Cells Lacking CDH3 (in Vitro 2D)

Figure 8:
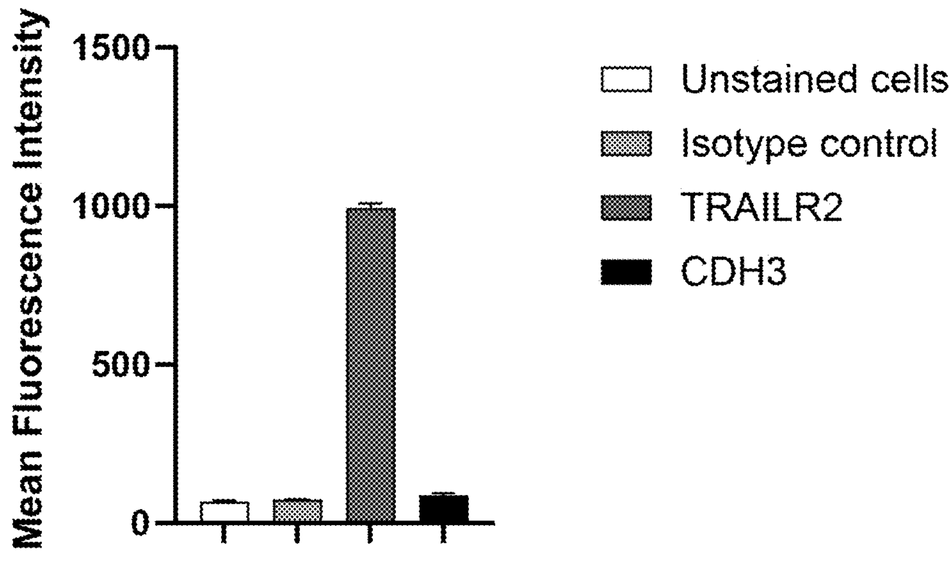
FIG. 8: Flow-cytometry analysis of the protein surface expression of TRAILR2 and CDH3 in GP2d CDH3 knock-out cells generated by CRISPR/Cas9. Results are shown as the mean fluorescence intensity.

Next it was confirmed that the increase in apoptosis modulated by the bispecific CDH3/TRAILR2 binding molecules of the invention is specifically mediated by CDH3 present on the surface of the GP2d cells. To demonstrate this, GP2d cells were generated that lack CDH3 on the cell surface (CDH3 knock-out cells) by gene editing using the CRISPR/Cas9 system. As shown in FIG. 8, Flow-cytometry confirmed the absence of CDH3 protein on GP2d-CDH3 knock-out (CDH3-KO) cells, which retained similar TRAILR2 protein on the surface as the isogenic GP2d (CDH3 wildtype) cells. The same bispecific molecules tested previously on GP2d cells were tested on GP2d CDH3 KO cells.

Figure 9:
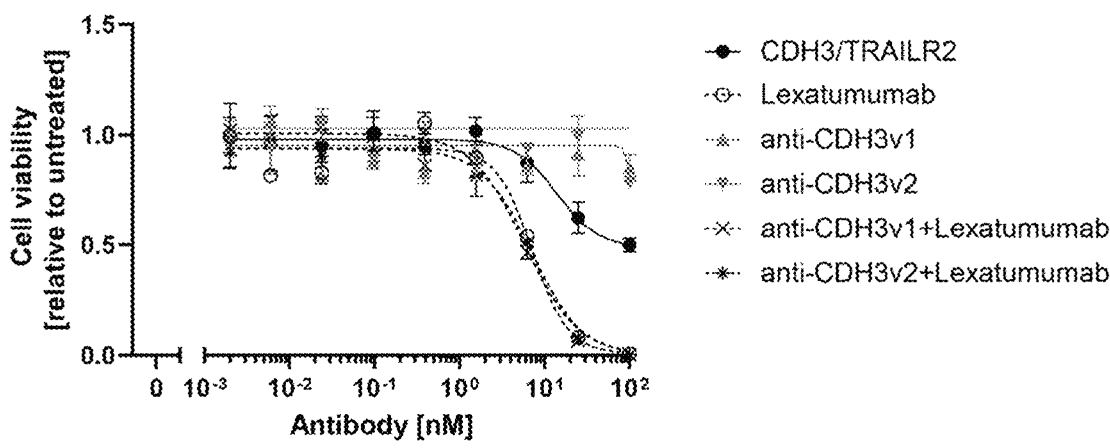
FIG. 9: Effect of antibodies incubation on cell viability in absence of CDH3 target. GP2d (CDH3 knock-out) cells were treated for 24 h with different concentrations of (i) an exemplary CDH3/TRAILR2 bispecific molecule of the invention, (ii) anti-TRAILR2 alone (Lexatumumab), (iii) anti-CDH3v1 alone, (iv) anti-CDH3v2 alone, or (iv) the equivalent combination of separate anti-TRAILR2 (Lexatumumab) and anti-CDH3v1 (or anti-CDH3v2) antibodies. The data is expressed as mean relative values compared to untreated control.

FIG. 9 shows that the TRAILR2 antibody (Lexatumumab) alone significantly decrease cell viability (EC50: 7.192 nM) of GP2d CDH3 knock-out cells, similar to the effect observed on GP2d wild type cells (EC50: 5.802 nM; FIG. 5), and the addition of anti-CDH3 in free-combination (either anti-CDH3v1 or anti-CDH3v2) did not change the effect observed with anti-TRAILR2 antibody alone. In contrast, the bispecific CDH3/TRAILR2 binding molecule CDH3/TRAILR2v1 had only a minor impact on cell viability of GP2d CDH3 knock-out cells and did not reach 50% cell killing at the highest tested concentration (200 nM).

Figure 10:
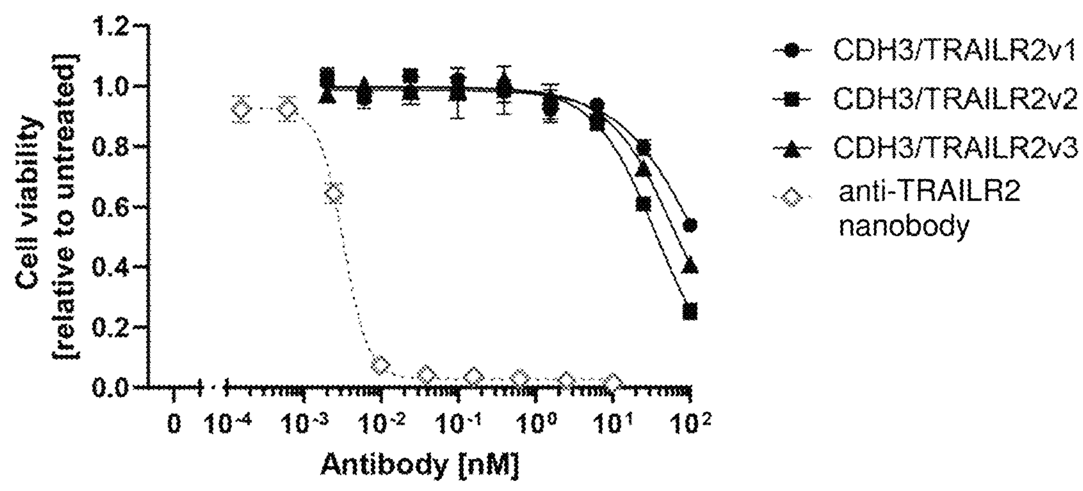
FIG. 10: Effect of antibodies incubation on cell viability in absence of CDH3. GP2d (CDH3 knock-out) cells were treated for 24 h with different concentrations of (i) EC1-binding CDH3/TRAILR2 bispecific molecules (CDH3/TR2v1, CDH3/TR2v2, CDH3/TR2v3) or (ii) anti-TRAILR2 alone (anti-TRAILR2 nanobody). The data is expressed as mean relative values compared to untreated control.

FIG. 10 shows the potency of the anti-TRAILR2 nanobody on GP2d CDH3 KO cells, which was similar as previously detected on GP2d WT cells. In contrast, the 4 bispecific molecules binding TRAILR2 and the EC1 domain of CDH3 (CDH3/TRAILR2v1, CDH3/TRAILR2v2, CDH3/TRAILR2v3, CDH3/TRAILR2v7) showed significant lack of potency and were approximately 41666-fold, 12602-fold, or 21504-fold less potent than the anti-TRAILR2 nanobody.

Figure 11:
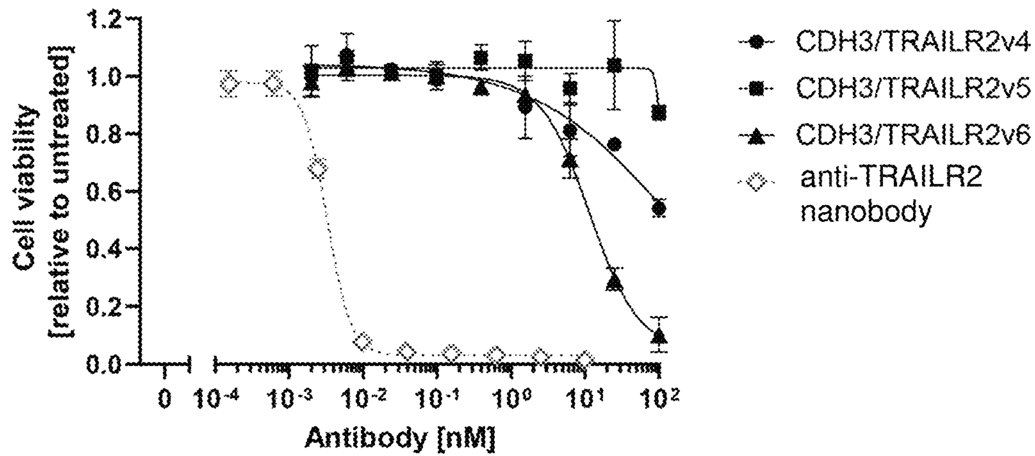
FIG. 11: Effect of antibodies incubation on cell viability in absence of CDH3. GP2d (CDH3 knock-out) cells were treated for 24 h with different concentrations of (i) EC2-binding CDH3/TRAILR2 bispecific molecules (CDH3/TR2v4, CDH3/TR2v5, CDH3/TR2v6) or (ii) anti-TRAILR2 alone (anti-TRAILR2 nanobody). The data is expressed as mean relative values compared to untreated control.

FIG. 11 shows the potency of 3 bispecific molecules binding TRAILR2 and the EC2 domain of CDH3 (CDH3/TRAILR2v4, CDH3/TRAILR2v5, CDH3/TRAILR2v6), which were all over 30000-fold less potent than the anti-TRAILR2 nanobody.

This confirms that the bispecific molecules generated in the present study only induce apoptosis in the presence of CDH3, while both anti-TRAILR2 antibodies, Lexatumumab and the anti-TRAILR2 nanobody, induce apoptosis regardless of whether CDH3 is present or not.

Example 4: Effect of the Bispecific CDH3/TRAILR2 Molecules on the NCI-H358 Cells (In Vitro 3D)

In order to extend the in vitro analysis, the bispecific CDH3/TRAILR2 molecules were tested on a cell line grown as spheroids (3D culture model) in order to mimic the growth conditions of a tumor in vivo. NCI-H358 cells, which are derived from a Lung adenocarcinoma, were plated in 2% Cultrex 3D RGF BME (R+D Systems 3445-005-01) in 96-well Clear Round Bottom Ultra-Low Attachment Microplate (Corning, 7007) at 2,000 cells per well. The cells were treated for 48 h with serial dilutions of the same molecules that were tested in example 3 on GP2d cells. NCI-H358 cells were incubated with (i) the bispecific molecule (CDH3/TRAILR2v1), (ii) anti-TRAILR2 antibody alone (Lexatumumab or the anti-TRAILR2 nanobody), (iii) anti-CDH3 antibody alone (anti-CDH3v1 or anti-CDH3v2), or (iv) a combination of anti-TRAILR2 (Lexatumumab) and anti-CDH3 (CDH3v1 or CDH3v2) antibodies.

Figure 12:
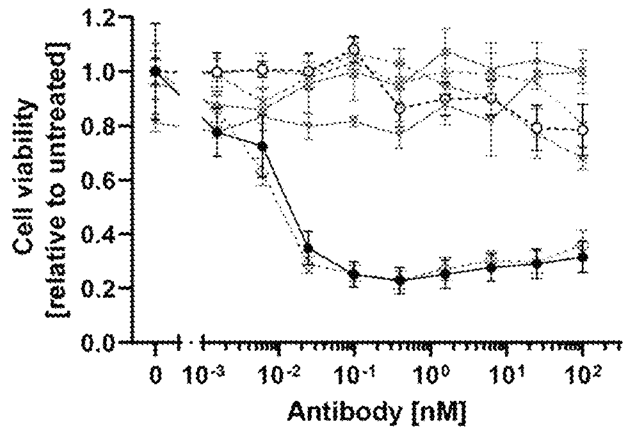
FIG. 12: Effect of antibodies incubation on cell viability in a 3D cell culture model. NCI-H358 cells were treated for 48 h with different concentrations of (i) CDH3/TRAILR2 bispecific molecule (CDH3/TR2v1), (ii) anti-TRAILR2 alone (Lexatumumab), (iii) anti-CDH3v1 (or anti-CDH3v2) alone, or (iv) the equivalent combination of separate anti-TRAILR2 (Lexatumumab) and anti-CDH3v1 (or anti-CDH3v2) antibodies. The data is expressed as mean relative values compared to untreated control.
Figure 13:
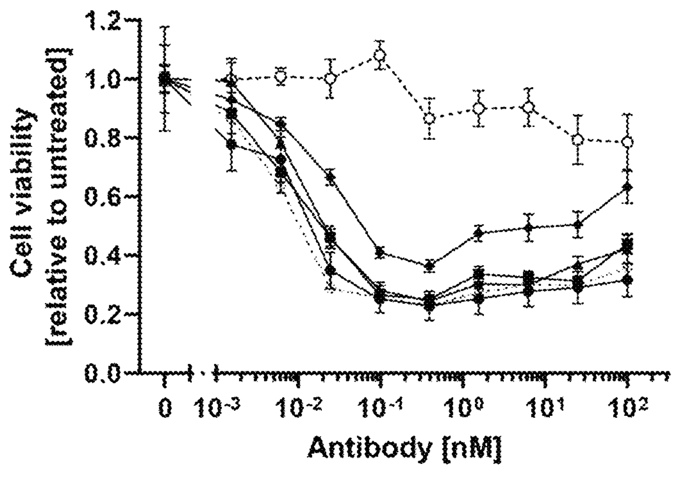
FIG. 13: Effect of antibodies incubation on cell viability in a 3D cell culture model. NCI-H358 cells were treated for 48 h with different concentrations of (i) EC1-binding TRAILR2/CDH3 bispecific molecules (CDH3/TR2v1, CDH3/TR2v2, CDH3/TR2v3) or (ii) anti-TRAILR2 alone (anti-TRAILR2 nanobody). The data is expressed as mean relative values compared to untreated control.
Figure 14:
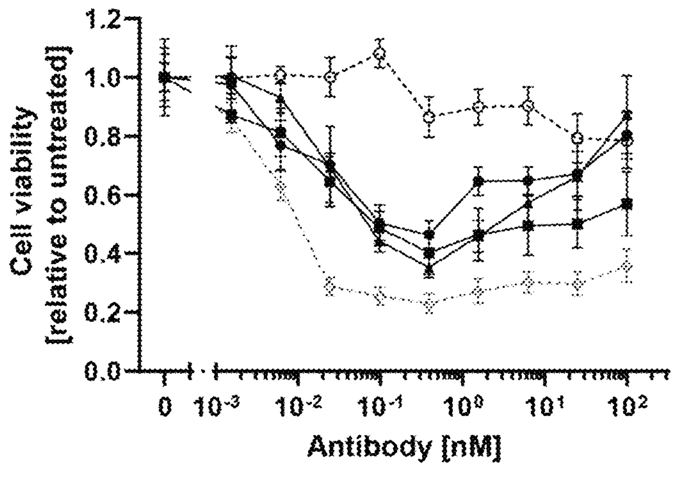
FIG. 14: Effect of antibodies incubation on cell viability in a 3D cell culture model. NCI-H358 cells were treated for 48 h with different concentrations of (i) EC2-binding CDH3/TRAILR2 bispecific molecules (CDH3/TR2v4, CDH3/TR2v5, CDH3/TR2v6) or (ii) anti-TRAILR2 alone (anti-TRAILR2 nanobody). The data is expressed as mean relative values compared to untreated control.

FIG. 12 shows the effect of these molecules on cell viability in the NCI-H358 3D model. No effect on cell viability was detected with the anti-CDH3 molecules alone (anti-CDH3v1 or anti-CDH3v2), Lexatumumab alone, or the combination of anti-CDH3 with Lexatumumab. A similar efficacy was only detected with CDH3/TRAILR2v1 and the anti-TRAILR2 nanobody. Shown in FIG. 13 is the testing of the EC1-binding CDH3/TRAILR2 molecules (CDH3/TRAILR2v1, CDH3/TRAILR2v2, CDH3/TRAILR2v3 and CDH3/TRAILR2v7) that all showed similar efficacy as TAS266. In contrast, the EC2 binding CDH3/TRAILR2 molecules (CDH3/TRAILR2v4, CDH3/TRAILR2v5, CDH3/TRAILR2v6) showed reduced efficacy compared to the EC1 binders and TAS266 (FIG. 14).

This shows that, surprisingly, only the EC1-binding bispecific molecules can induce apoptosis at a similar efficacy as the anti-TRAILR2 nanobody, albeit with significantly increased accuracy since only CDH3-expressing cells are targeted. In contrast, the EC2-binding bispecific molecules CDH3/TRAILR2v4, CDH3/TRAILR2v5 and CDH3/TRAILR2v6 did not reach the efficacy level of the anti-TRAILR2 nanobody.

Example 5: CDH3/TRAILR2 Molecules Induce Caspase-8 Activation in GP2d Cells

It was next investigated whether the reduction in cell viability was caused by the induction of TRAIL-induced apoptosis, which is mediated by the recruitment and activation of caspase-8. To determine if the antibodies and binding molecules prepared herein are able to specifically activate the apoptotic pathway, the inventors measured caspase-8 activities in the GP2d cell line. To set up the experiment, the GP2d cells were rested overnight at 37° C. and 5% $CO_2$ and incubated the following day with different antibody or binding molecule dilutions ranging from 0,001 to 10 nM. Caspase-8 activities were measured 7 h after treatment from harvested cell extracts using Promega Caspase-Glo 8 Assay (Cat. #G8201) respectively. The luminescence of each sample was then measured using the VICTOR X4 2030 Multilabel Plate Reader from Perkin Elmer.

Figure 15:
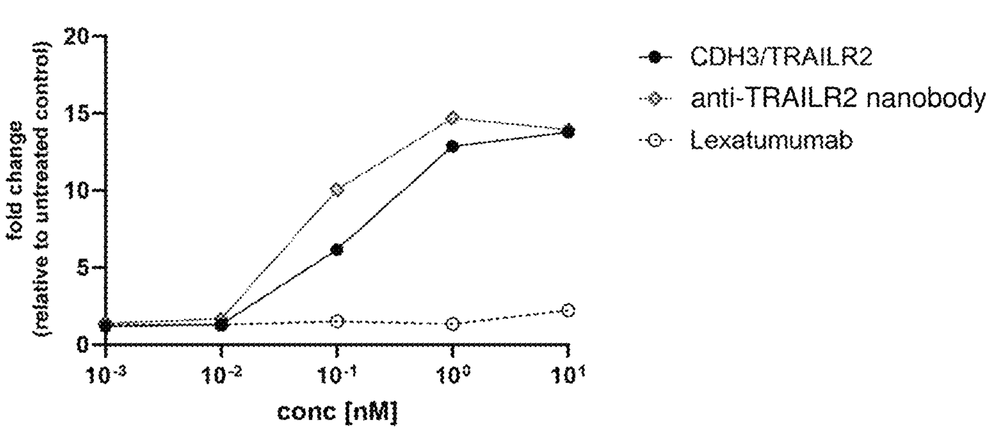
FIG. 15: Analysis of apoptosis induction (caspase 8 activation assay) after antibody incubation. GP2d cells were treated for 7 h with different concentrations of (i) an exemplary bispecific CDH3/TRAILR2 binding molecule of the invention, or anti-TRAILR2 molecules (ii) anti-TRAILR2 nanobody or (iii) Lexatumumab and Caspase-8 activation was measured. The data is expressed as mean relative values of the fold change compared to untreated control.

FIG. 15 shows the caspase activity 7 h after treatment with either a bispecific CDH3/TRAILR2 binding molecule of the invention, the anti-TRAILR2 nanobody or Lexatumumab relative to untreated controls. Lexatumumab increased activated caspase 8 only approximately 2-fold at the highest concentration (10 nM). In contrast, increases of activated Caspase 8 were detected with 0.1 nM (or higher) concentrations of CDH3/TRAILR2v1 and the anti-TRAILR2 nanobody. Levels of activated Caspase 8 increased similarly with higher concentrations of the bispecific CDH3/TRAILR2 binding molecule and the anti-TRAILR2 nanobody and were approximately 15-fold over background at 10 nM treatment. This data demonstrates that the decrease in cell viability observed in the cell killing assays is not due to unspecific mechanisms, and that the bispecific CDH3/TRAILR2 molecule is able to efficiently and specifically induce apoptosis in the target cells. In agreement with the cell viability data, it was observed that the incubation of GP2d cells with the bispecific CDH3/TRAILR2 binding molecule resulted in superior caspase-8 activation compared to the anti-TRAILR2 antibody Lexatumumab.

Example 6: In Vivo Anti-Tumor Activity of CDH3/TRAILR2 Molecules in the GP2d Xenograft Model The in vivo efficacy of three EC1 domain binding and three EC2 domain binding CDH3/TRAILR2 molecules was investigated. For this purpose, GP2d cancer cells were engrafted into immunodeficient mice and the effect of the administration of a molecule of the invention on the tumor volume was measured. Female BomTac:NMRI-Foxn1nu mice were subcutaneously engrafted with $5.0\times10^6$ Gp2d cells (in 0.1 mL 5% FBS in PBS:Matrigel ratio of 1:1 (v/v)) and the tumor growth was monitored until it reached about 200 $mm^3$. Mice were randomized in seven groups and a single injection of either vehicle control, EC1 binder (CDH3/TRAILR2v1, CDH3/TRAILR2v2, or CDH3/TRAILR2v3), or EC2 binder (CDH3/TRAILR2v4, CDH3/TRAILR2v5, or CDH3/TRAILR2v6) was administered at 1 mg/kg intravenously (i.v.). Tumor growth was subsequently monitored for 34 days, except for the vehicle treated cohort that was euthanized after 24 days when the upper tumor volume limit of 1000 mm3 was reached.

Figure 16:
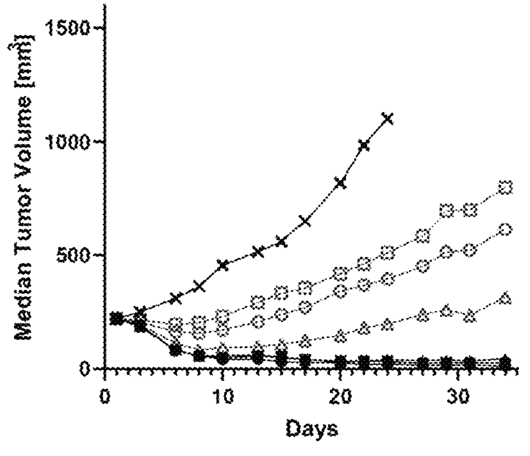
FIG. 16: In vivo data on GP2d xenograft model. In vivo efficacy of bispecific molecules recognizing human TRAILR2 and human CDH3: The EC1-binding CDH3/TRAILR2 molecules CDH3/TRAILR2v1 (black circles), CDH3/TRAILR2v2 (black squares), CDH3/TRAILR2v3 (black triangles) or the EC2-binding CDH3/TRAILR2 molecules CDH3/TRAILR2v4 (white circles), CDH3/TRAILR2v5 (white squares), and CDH3/TRAILR2v6 (white triangles) or vehicle control (grey crosses) was administered to mice bearing GP2d tumor cells. Tumor volume (mm3) was measured after administration on the indicated days. The data is expressed as the median of the tumor volumes. At least 8 animals were included on each group.

The data presented in FIG. 16 demonstrates that binding molecules of the invention are able to induce significant and extended reductions of the tumor volume when compared with the control group. Unexpectedly, the EC1-binding molecules showed superior efficacy compared to the EC2 binding molecules. The EC1 binders lead to long-lasting regressions with 132%, 125% and 125% tumor growth inhibition, respectively. In contrast while single treatment with the EC2 binding molecules lead to initial regressions, tumor regrowth was observed from day 10 leading to only 70%, 61% and 102% tumor growth inhibition, respectively.

Example 7: Internalization Capacity of EC1-Binding Bispecific CDH3/TRAILR2 Molecules The rate of endocytosis-mediated internalization and lysosomal degradation of surface-receptor binding biologics affects their stability and hence their plasma half-life and duration of response. CDH3 EC1-binding compounds developed previously by others show a high internalization capacity (WO12057328A1) and therefore might be less capable to support a durable and efficacious activation of TRAILR2 at the cell surface if used in a bispecific compound setting.

The capability of an exemplary EC1-binding bispecific CDH3/TRAILR2 compound, the TRAILR2-binding antibody Lexatumumab, or an anti-CDH3 EC1-specific antibody to internalize was analysed in comparison to a commercially available, internalization-proficient anti-CDH3 antibody (#MAB861, Bio-Techne®, R&D systems). To achieve this, GP2d colorectal cancer cells were seeded in 96 well plates (#3340, Corning, NY, USA) one day before compound exposure. Prior to addition of compounds, antibodies were incubated with Incucyte® Fabfluor-pH Antibody Labeling Reagent (#4722, Sartorius, Goettingen, Germany) according to manufacturer's protocol. Next, Fabfluor-labelled antibody was added to cells at 1 nM concentration in a total volume of 100 μl, and cells were analysed for red Fabfluor signal as a surrogate for internalization in the Incucyte® S3 Live-Cell Analysis Instrument (Sartorius) with 10× magnification, four pictures/well every 1 h for 24 h.

Figure 17:
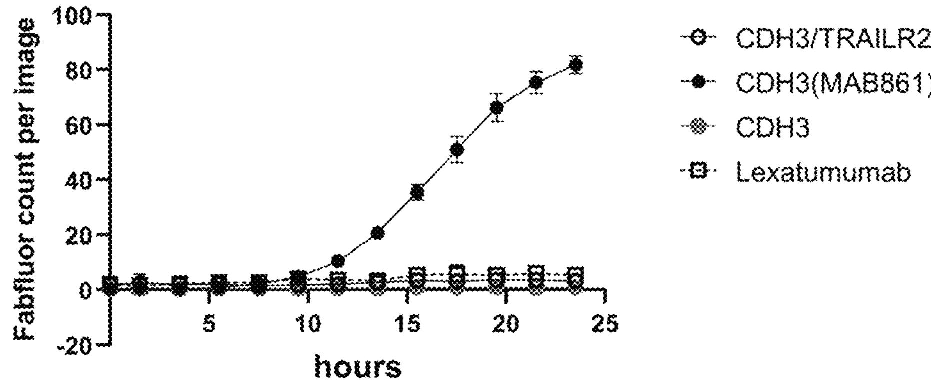
FIG. 17: Internalization of EC1-binding CDH3/TRAILR2 and single antigen-binding antibodies. GP2d caspase 8-knockout cells were exposed to 1 nM Fabfluor-labelled antibodies: An exemplary EC1-binding CDH3/TRAILR2 molecule (white circles), an exemplary EC1-binding CDH3 molecule (crossed white circles), the TRAILR2-binding molecule Lexatumumab (white squares), or, as an in-house positive control for moderate internalization, the commercially available CDH3-binding molecule CDH3 (MAB861, Bio-Techne®, R&D systems) (black circles). Fabfluor counts per image as a quantitative measure for internalization were analysed after antibody administration at the indicated hours. Shown is the mean of measurements. Error bars indicate standard deviation.

The data presented in FIG. 17 demonstrates lack of measurable internalization (no detectable Fabfluor red signal) for a bispecific CDH3/TRAILR2 compound, the anti-TRAILR2 antibody Lexatumumab, and an EC1-binding CDH3 compound at the applied concentration in comparison to the moderately internalizing anti-CDH3 antibody MAB861. The absence of measureable internalization of an exemplary bispecific EC1-binding CDH3/TRAILR2 antibody prepared herein is in accordance with the long-lasting tumor regressions observed in the GP2d xenograft model, as demonstrated in FIG. 16.

Example 8: Stability of the Bispecific CDH3/TRAILR2 Binding Molecules at Low pH Conditions The stability of the bispecific CDH3/TRAILR2 molecules was tested at low pH conditions. During production, biological products are exposed to low pH conditions in order to achieve elution from the affinity column ("capture step"). The low pH conditions are also required in order to inactivate potential contaminants such as bacteria, fungi and viruses. Effective clearance of potential contaminants is an important step during the manufacture of biological products using mammalian cell lines to ensure drug safety. For many recombinant proteins, however, incubation at low pH induces aggregation and reduces the recovered protein yield. Thus, stability of the protein at low pH is an important factor for the successful and efficient production of therapeutic proteins.

To test the stability of the bispecific CDH3/TRAILR2 binding molecules at low pH, the pH was adjusted to pH 3.5 with 1M acetic acid, followed by incubation for 90 minutes at room temperature, followed by neutralization to pH 5.0 with 1M Tris buffer (pH 9.0). The sample concentration was measured and the potential formation of aggregates (high molecular weight species, HMWS) or fragments (low molecular weight species, LMWS) was determined by analytical size exclusion chromatography (aSEC).

Results are summarized in Table 19 below, demonstrating that none of the binding molecules CDH3/TRAILR2v1, CDH3/TRAILR2v2, CDH3/TRAILR2v3, CDH3/TRAILR2v4, CDH3/TRAILR2v5, CDH3/TRAILR2v6 or CDH3/TRAILR2v7 showed any significant increase of HMWS (<1.06%) or LMWS (0%), or any significant decrease of the main peak (<1.06%) compared to the starting material, which demonstrates good stability after incubation for 90 minutes at pH 3.5.

TABLE 19

Affinities (KD) of CDH3/TRAILR2 binding proteins to human CDH3 as determined by SPR analysis

| CDH3/TRAILR2 | aSEC Stability - 90 min, RT | | |
|---|---|---|---|
| Bispecific molecule | Δ % HMWS | Δ % Main | Δ % LMWS |
| CDH3/TRAILR2v1 | −0.68 | −0.70 | 0.00 |
| CDH3/TRAILR2v2 | −0.17 | 0.17 | 0.00 |
| CDH3/TRAILR2v3 | −0.04 | 0.04 | 0.00 |
| CDH3/TRAILR2v4 | 0.54 | −0.54 | 0.00 |
| CDH3/TRAILR2v5 | −0.29 | 0.37 | −0.08 |
| CDH3/TRAILR2v6 | 1.06 | −1.06 | 0.00 |
| CDH3/TRAILR2v7 | 0.02 | −0.02 | 0.00 |

The invention claimed is:

1. A binding molecule comprising:

(a) at least one antigen binding site that binds specifically to TNF-related apoptosis-inducing ligand receptor 2 (TRAILR2), wherein the at least one antigen binding site that binds specifically to TRAILR2 comprises heavy chain CDRs comprising the amino acid sequences of SEQ ID NO:73 (CDR1), SEQ ID NO:74 (CDR2) and SEQ ID NO:75 (CDR3) and light chain CDRs comprising the amino acid sequences of SEQ ID NO:77 (CDR1), SEQ ID NO:78 (CDR2) and SEQ ID NO:79 (CDR3); and (b) at least one antigen binding site that binds specifically to cadherin-3 (CDH3), wherein said at least one antigen binding site that binds specifically to CDH3 is selected from the group consisting of:

i. an antigen binding site comprising heavy chain CDRs comprising the amino acid sequences of SEQ ID NO:3 (CDR1), SEQ ID NO:4 (CDR2) and SEQ ID NO:5 (CDR3) and light chain CDRs comprising the amino acid sequences of SEQ ID NO:7 (CDR1), SEQ ID NO:8 (CDR2) and SEQ ID NO:9 (CDR3);

ii. an antigen binding site comprising heavy chain CDRs comprising the amino acid sequences of SEQ ID NO:13 (CDR1), SEQ ID NO:14 (CDR2) and SEQ ID NO:15 (CDR3) and light chain CDRs comprising the amino acid sequences of SEQ ID NO:17 (CDR1), SEQ ID NO:18 (CDR2) and SEQ ID NO:19 (CDR3);

iii. an antigen binding site comprising heavy chain CDRs comprising the amino acid sequences of SEQ ID NO:23 (CDR1), SEQ ID NO:24 (CDR2) and SEQ ID NO:25 (CDR3) and light chain CDRs comprising the amino acid sequences of SEQ ID NO:27 (CDR1), SEQ ID NO:28 (CDR2) and SEQ ID NO:29 (CDR3); and iv. an antigen binding site comprising heavy chain CDRs comprising the amino acid sequences of SEQ ID NO:33 (CDR1), SEQ ID NO:34 (CDR2) and SEQ ID NO:35 (CDR3) and light chain CDRs comprising the amino acid sequences of SEQ ID NO:37 (CDR1), SEQ ID NO:38 (CDR2) and SEQ ID NO:39 (CDR3).

2. The binding molecule of claim 1, wherein the at least one antigen binding site that binds specifically to CDH3 is an immunoglobulin (Ig) molecule and the at least one antigen binding site that binds specifically to TRAILR2 comprises one or more scFv(s).

3. The binding molecule of claim 2, wherein the one or more scFv(s) are fused to the C-terminus of the Ig molecule, optionally wherein a first scFv is fused to a first heavy chain and a second scFv is fused the second heavy chain of the Ig molecule, respectively.

4. The binding molecule of claim 1, wherein the at least one antigen binding site that binds specifically to CDH3 is selected from the group consisting of:

i. a heavy chain variable domain (VH) comprising the amino acid sequence of SEQ ID NO:2 and a light chain variable domain (VL) comprising the amino acid sequence of SEQ ID NO:6;

ii. a VH comprising the amino acid sequence of SEQ ID NO:12 and a VL comprising the amino acid sequence of SEQ ID NO:16;

iii. a VH comprising the amino acid sequence of SEQ ID NO:22 and a VL comprising the amino acid sequence of SEQ ID NO:26; and iv. a VH comprising the amino acid sequence of SEQ ID NO:32 and a VL comprising the amino acid sequence of SEQ ID NO:36.

5. The binding molecule of claim 1, wherein the at least one antigen binding site that binds specifically to TRAILR2 is an antigen binding site comprising a heavy chain variable domain (VH) comprising the amino acid sequence of SEQ ID NO:72 and a light chain variable domain (VL) comprising the amino acid sequence of SEQ ID NO:76.

6. The binding molecule of claim 1, wherein the at least one antigen binding site that binds to CDH3 comprises:

i. a heavy chain comprising the amino acid sequence of SEQ ID NO:80 and a light chain comprising the amino acid sequence of SEQ ID NO:81;

ii. a heavy chain comprising the amino acid sequence of SEQ ID NO:82 and a light chain comprising the amino acid sequence of SEQ ID NO:83;

iii. a heavy chain comprising the amino acid sequence of SEQ ID NO:84 and a light chain comprising the amino acid sequence of SEQ ID NO:85; or iv. a heavy chain comprising the amino acid sequence of SEQ ID NO:86 and a light chain comprising the amino acid sequence of SEQ ID NO:87.

7. The binding molecule of claim 1, wherein the at least one antigen binding site that binds to TRAILR2 comprises the amino acid sequence of SEQ ID NO:71.

8. The binding molecule of claim 1, comprising i. a modified heavy chain comprising the amino acid sequence of SEQ ID NO: 1 and a light chain comprising the amino acid sequence of SEQ ID NO:81;

ii. a modified heavy chain comprising the amino acid sequence of SEQ ID NO: 11 and a light chain comprising the amino acid sequence of SEQ ID NO:83;

iii. a modified heavy chain comprising the amino acid sequence of SEQ ID NO: 21 and a light chain comprising the amino acid sequence of SEQ ID NO:85; or iv. a modified heavy chain comprising the amino acid sequence of SEQ ID NO: 31 and a light chain comprising the amino acid sequence of SEQ ID NO:87.

9. An isolated nucleic acid encoding the binding molecule of claim 1.

10. An expression vector comprising the nucleic acid of claim 9.

11. An isolated host cell comprising the expression vector of claim 10.

12. A method of manufacturing the binding molecule of claim 1, comprising i. cultivating a host cell comprising an expression vector comprising a nucleic acid encoding the binding molecule of claim 1 under conditions allowing expression of the molecule, and ii. recovering the molecule, and optionally iii. further purifying and/or modifying and/or formulating the molecule.

13. A method for treatment of cancer comprising administering an effective amount of the binding molecule of claim 1 to a patient in need thereof, wherein the cancer is pancreatic cancer.

14. A pharmaceutical composition comprising the binding molecule of claim 1 and a pharmaceutically acceptable carrier.

* * * * *